US011344619B2

(12) United States Patent
Fox

(10) Patent No.: US 11,344,619 B2
(45) Date of Patent: May 31, 2022

(54) FORMULATION CONTAINING TLR AGONIST AND METHODS OF USE

(71) Applicant: ACCESS TO ADVANCED HEALTH INSTITUTE, Seattle, WA (US)

(72) Inventor: Christopher B. Fox, Sumner, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 468 days.

(21) Appl. No.: 16/098,615

(22) PCT Filed: May 11, 2017

(86) PCT No.: PCT/US2017/032287
§ 371 (c)(1),
(2) Date: Nov. 2, 2018

(87) PCT Pub. No.: WO2017/200852
PCT Pub. Date: Nov. 23, 2017

(65) Prior Publication Data
US 2019/0142935 A1 May 16, 2019

Related U.S. Application Data

(60) Provisional application No. 62/337,322, filed on May 16, 2016.

(51) Int. Cl.
A61K 39/395 (2006.01)
A61K 39/39 (2006.01)
A61K 39/04 (2006.01)
A61K 39/12 (2006.01)
C07K 14/705 (2006.01)
A61K 35/76 (2015.01)
A61K 45/06 (2006.01)
A61P 31/12 (2006.01)
A61P 33/04 (2006.01)
A61P 31/06 (2006.01)
A61P 35/00 (2006.01)
A61K 39/00 (2006.01)

(52) U.S. Cl.
CPC ............ A61K 39/39 (2013.01); A61K 35/76 (2013.01); A61K 39/04 (2013.01); A61K 39/12 (2013.01); A61K 45/06 (2013.01); A61P 31/06 (2018.01); A61P 31/12 (2018.01); A61P 33/04 (2018.01); A61P 35/00 (2018.01); C07K 14/705 (2013.01); C07K 14/70596 (2013.01); A61K 2039/552 (2013.01); A61K 2039/55505 (2013.01); A61K 2039/55511 (2013.01); A61K 2039/55572 (2013.01); A61K 2039/57 (2013.01); A61K 2039/572 (2013.01); C12N 2740/16134 (2013.01)

(58) Field of Classification Search
None
See application file for complete search history.

(56) References Cited

U.S. PATENT DOCUMENTS

| 2007/0014841 A1* | 1/2007 | Martin ..................... A61P 31/04 424/450 |
| 2009/0181078 A1* | 7/2009 | Reed ..................... A61K 39/008 424/450 |
| 2013/0230578 A1* | 9/2013 | Wightman .............. A61P 37/00 424/450 |
| 2014/0112950 A1* | 4/2014 | Singh ................... A61K 39/295 424/196.11 |

FOREIGN PATENT DOCUMENTS

| WO | 2006086330 A2 | 8/2006 |
| WO | 2012024284 A1 | 2/2012 |
| WO | 2012117377 A1 | 9/2012 |
| WO | 2013132041 A2 | 9/2013 |
| WO | 2013139744 A1 | 9/2013 |
| WO | 2015144653 A1 | 10/2015 |
| WO | 2015161218 A1 | 10/2015 |

OTHER PUBLICATIONS

Chinese Office Action dated Dec. 18, 2020 for Application No. CN 201780035091.4 pp. 1-10.
Hem et al., "Aluminum-Containing Adjuvants: Properties, Formulation, and Use", Vaccine Adjuvants and Delivery Systems, Chapter 4, 2007, pp. 81-114.
Mullen et al., "Enhanced antibody production in mice to the malaria antigen AMA1 by CPG 7909 requires physical association of CpG and antigen", Vaccine, vol. 25, Issue 29, May 25, 2007, pp. 5343-5347.
Iyer et al., "Mechanism of adsorption of hepatitis B surface antigen by aluminum hydroxide adjuvant", Vaccine, vol. 22, Issues 11-12, Oct. 17, 2003, pp. 1475-1479.
Kaisho et al., "Pleiotropic function of Toll-like receptors", Microbes and Infection, vol. 6, Issue 15, Nov. 5, 2004, pp. 1388-1394.
Kasturi et al., "Programming the magnitude and persistence of antibody responses with innate immunity", Nature, vol. 470, 2011, pp. 543-547.
Andrew D Luster, "The role of chemokines in linking innate and adaptive immunity", Current Opinion in Immunology, vol. 14, Issue 1, Feb. 1, 2002, pp. 129-135.
Ruslan Medzhitov, "Toll-Like Receptors and Innate Immunity", Nature Reviews Immunology, vol. 1, Nov. 2001, pp. 135-145.
Takeda et al., "Toll-Like Receptors", Annual Review of Immunology, vol. 21, 2003, pp. 335-376.

(Continued)

Primary Examiner — Yunsoo Kim
(74) Attorney, Agent, or Firm — Newport IP, LLC; Benjamin A. Keim

(57) ABSTRACT

Stable aqueous formulations of adjuvant comprising a TLR7/8 agonist or a TLR4 agonist with a helper lipid that are adsorbed to alum are provided. Compositions and methods of using the formulations for stimulating an immune response are also provided.

17 Claims, 15 Drawing Sheets

(56) References Cited

OTHER PUBLICATIONS

Dowling et al., "Modulating Potency: Physicochemical Characteristics are a Determining Factor of TLR4-Agonist Nanosuspension Activity", Journal of Pharmaceutical Sciences, vol. 103, No. 3, Mar. 1, 2014, pp. 879-889.
Fox et al., "Adsorption of a synthetic TLR7/8 ligand to aluminum oxyhydroxide for enhanced vaccine adjuvant activity: A formulation approach," Journal of Controlled Release, vol. 244, Nov. 12, 2016, pp. 98-107.
International Search Report and Written Opinion issued in International Application No. PCT/US2017/032287, dated Jul. 21, 2014, 15 pages.
Kaczanowska et al., "TLR agonists: our best frenemy in cancer immunotherapy," Journal of Leukocyte Biology, vol. 93, No. 6, Mar. 8, 2013, pp. 847-863.
Smirnov et al., "Vaccine adjuvant activity of 3M-052: An imidazoquinoline designed for local activity without systemic cytokine induction," Vaccine, vol. 29, No. 33, May 19, 2011 (May 19, 2011), pp. 5434-5442.
Japanese Patent Application No. 2018-560185, First Office Action dated Feb. 18, 2021, 15 pages. (with English translation).
Dowling, et. al., "Modulating Potency: Physicochemical Characteristics Are A Determining Factor of TLR4-Agonist Nanosuspension Activity", Infectious Disease Research Institute, Seattle, WA, 2013, 12 pages.
Korean Patent Application No. 10-2018-7035495, Office Action dated Sep. 28, 2021, 9 pages. (with English translation).
Israel Patent Application No. 263028, Office Action dated Oct. 26, 2021, 10 pages. (English translation).
Brazil Patent Application No. BR112018073690-2, Office Action dated Oct. 18, 2021, 18 pages. (with English translation).
Yakugaku Zasshi, et al., "Influenza Vaccine and Adjuvant", Aug. 26, 2011, vol. 131, No. 12, 10 pages. (English Abstract).
Drug Delivery System, 2012, vol. 27, No. 1, 10 pages.
Drug Delivery System, 2010, vol. 25, No. 1, 9 pages.
JP 2018-560185, Second Office Action, dated Jan. 18, 2022, 15 pages. (with English translation).

* cited by examiner

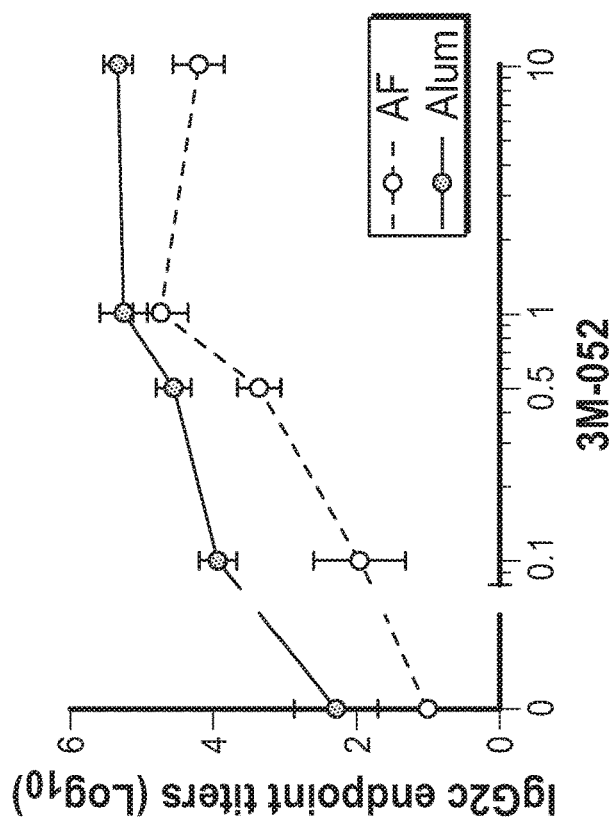
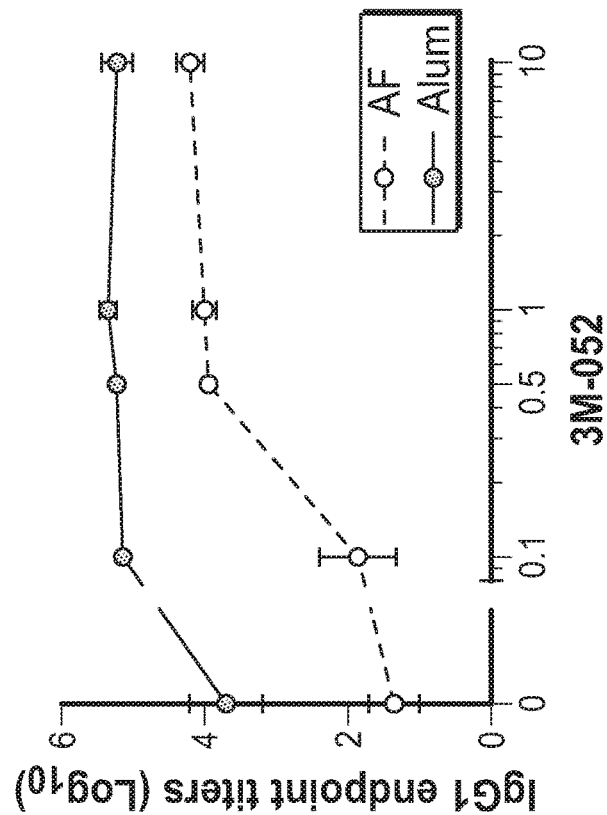
FIG. 6A
FIG. 6B

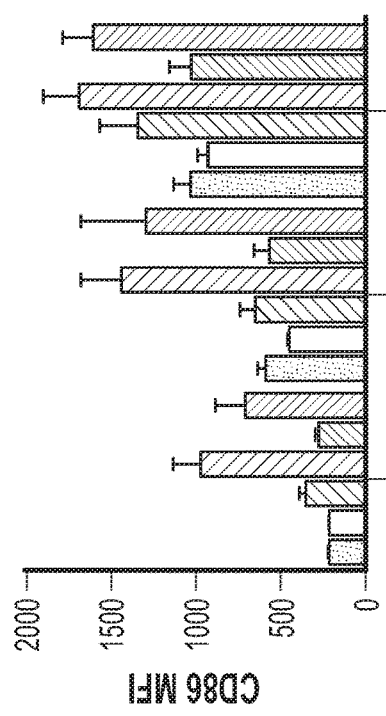
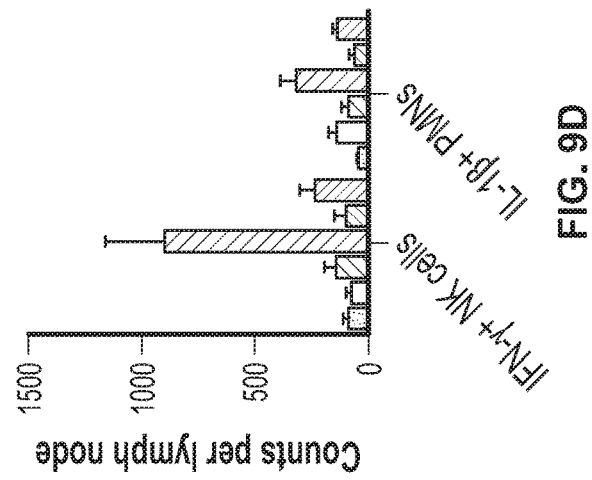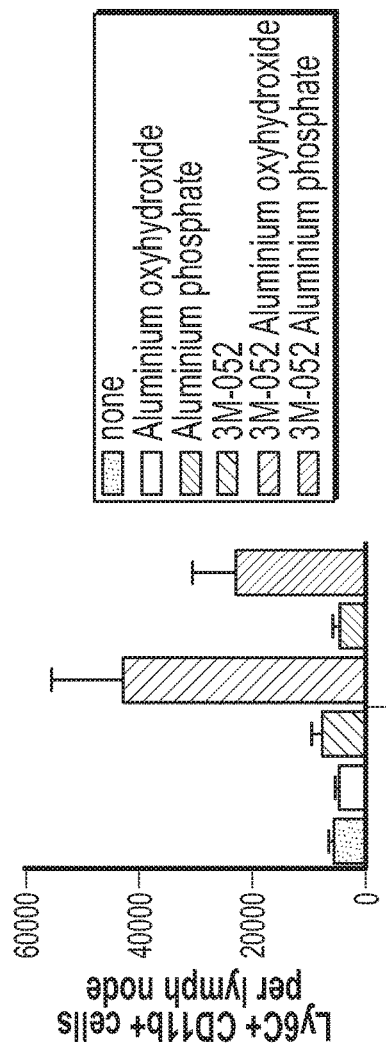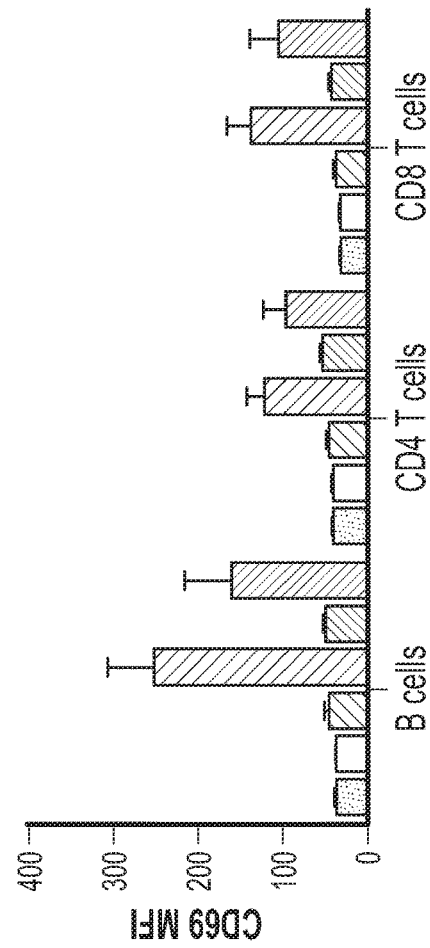
FIG. 9A
FIG. 9B
FIG. 9C
FIG. 9D

FORMULATION CONTAINING TLR AGONIST AND METHODS OF USE

CROSS-REFERENCE TO RELATED APPLICATIONS

This application is a national phase entry pursuant to 35 U.S.C. § 371 of International Application No. PCT/US2017/032287 filed May 11, 2017, which claims the benefit of priority of U.S. Provisional Application No. 62/337,322, filed May 16, 2016, each of which is hereby incorporated by reference in its entirety for any purpose.

STATEMENT REGARDING FEDERALLY SPONSORED RESEARCH OR DEVELOPMENT

This invention was made with government support under contract no. HHSO100201000039C awarded by the Biomedical Advanced Research and Development Authority (BARDA) within the Office of the Assistant Secretary for Preparedness and Response (ASPR) in the U.S. Department of Health and Human Services. The government has certain rights in the invention.

BACKGROUND OF THE INVENTION

Field of the Invention

The present invention relates to the field of pharmaceutical and vaccine formulations. More specifically, embodiments described herein relate to stable aqueous formulations of adjuvant comprising a TLR7/8 agonist or a TLR4 agonist and a helper lipid, which can optionally be adsorbed to an aluminum salt.

Description of the Related Art

Since Glenny's pioneering work in the early 20th century (1), aluminum salts have become the most widely used adjuvants in human vaccines, generating an unrivalled history of safety and suitability with various vaccine antigens. Aluminum salts generally comprise semi-crystalline nano- and micro-particles with a large surface area and a high charge density. They may be most effective as adjuvants when vaccine antigens are optimally adsorbed to the surface of the aluminum salt particles (2). Aluminum salts are effective in boosting antibody responses to vaccine antigens, but there is little indication that they substantially augment cellular immunity to vaccine antigens. Induction of effective cellular immunity is likely essential for developing effective vaccines for several diseases including tuberculosis, HIV, and malaria. Therefore, the adsorption of additional immunostimulants to aluminum salts should also be a paramount consideration in vaccine formulation development. Thus, an advancement in the clinical use of adjuvants occurred in 2009 when the US FDA approved GlaxoSmithKline's human papilloma virus vaccine Cervarix® for human use in 2009; Cervarix® contains AS04, an adjuvant system consisting of the Toll-like receptor 4 (TLR4) ligand monophosphoryl lipid A (MPL®) adsorbed to aluminum oxyhydroxide (3). Besides TLR4 agonists, other pattern recognition receptor (PRR) ligands in preclinical and clinical development may benefit from adsorption to aluminum salts (4). Some PRR ligands, such as the TLR4 ligand MPL®, adsorb to some aluminum salts due to physicochemical structure compatibility. Thus, aluminum oxyhydroxide adsorbs such molecules due to phosphate ligand exchange and/or electrostatic interactions (2). However, other PRR ligands of interest, such as the TLR7/8 agonist imidazoquinolines, do not contain structural moieties that would promote adsorption to aluminum oxyhydroxide.

All references cited herein, including patent applications and patent publications are herein incorporated by reference in their entirety, as if each individual reference is specifically and individually indicated to be incorporated by reference.

BRIEF SUMMARY OF THE INVENTION

The present disclosure provides a TLR aqueous formulation comprising: (a) a TLR agonist; and (b) a helper lipid. In certain embodiments, the TLR agonist comprises a TLR2 agonist, a TLR3 agonist, a TLR4 agonist, a TLR5 agonist, a TLR6 agonist, a TLR7 agonist, a TLR8 agonist, a TLR7/8 agonist, or a TLR9 agonist. In certain embodiments, the aqueous formulation further comprises an aluminum salt.

The present disclosure provides a TLR 7/8 aqueous formulation comprising: (a) a TLR7/8 agonist; and (b) a helper lipid. In certain embodiments, the aqueous formulation is a stable nanosuspension having a particle size of 400 nm or less.

The present disclosure provides a composition comprising: (a) a TLR7/8 agonist; (b) a helper lipid; and (c) an aluminum salt. In certain embodiments, the TLR7/8 agonist is adsorbed to the aluminum salt. In certain embodiments, the TLR7/8 agonist is adsorbed to the aluminum salt at 25 percent of the aluminum salt. In certain embodiments, the aluminum salt is selected from the group consisting of aluminum hydroxide, aluminum trihydrate, aluminum oxyhydroxide, aluminum phosphate, aluminum hydroxyphosphate, aluminum hydroxyphosphate sulfate, and potassium aluminum sulfate. In certain embodiments, the aluminum salt comprises Alhydrogel®. In certain embodiments, the aluminum salt comprises AdjuPhos®. In certain embodiments, the TLR7/8 agonist comprises 3M-052. In certain embodiments, the helper lipid is a phospholipid or a quaternary ammonium salt lipid. In certain embodiments, the helper lipid comprises a $C_{10\text{-}20}$ alkyl chain. In certain embodiments, the helper lipid is selected from DOPC, DSPG, DSTAP, and Polysorbate 80. In certain embodiments, the helper lipid is selected from DSPG and DSTAP. In certain embodiments, the composition comprises 3M-052, Alhydrogel®, and DSPG. In certain embodiments, the composition comprises 3M-052, AdjuPhos®, and DSTAP. In certain embodiments, the composition further comprises an antigen. In certain embodiments, the antigen is selected from a tuberculosis-related antigen, influenza-related antigen, hemagglutinin-related antigen, cancer-related antigen, viral-related antigen and amebiasis-related antigen. In certain embodiments, the tuberculosis-related antigen is selected from the group consisting of ID93, ID91, and BCG. In certain embodiments, the influenza-related antigen is selected from the group consisting of H5N1, influenza A, influenza B, and influenza C. In certain embodiments, the amebiasis-related antigen is LecA. In certain embodiments, the viral antigen is selected from the group consisting of hepatitis B and hepatitis C. In certain embodiments, the composition is stable. In certain embodiments, the composition is stable for at least about six months. In certain embodiments, the composition is stable for at least about one year. In certain embodiments, the composition is stable at 2-8° C. for at least six months. In certain embodiments, the composition is stable at 2-8° C. for at least one year.

The present disclosure provides a TLR4 aqueous formulation comprising: (a) a TLR4 agonist; and (b) a helper lipid, which is DPTAP. In certain embodiments, the aqueous formulation is a stable nanosuspension having a particle size of 400 nm or less.

The present disclosure provides a composition comprising: (a) a TLR4 agonist; (b) a helper lipid, which is DPTAP; and (c) an aluminum salt, which is AdjuPhos®. In certain embodiments, the TLR4 agonist is adsorbed to the aluminum salt. In certain embodiments, the TLR7/8 agonist is adsorbed to the aluminum salt at 25 percent of the aluminum salt. In certain embodiments, the TLR4 agonist is adsorbed to the aluminum phosphate. In certain embodiments, the TLR4 agonist comprises 3D-monophosphoryl lipid A (MPL). In certain embodiments, the TLR4 agonist comprises GLA. In certain embodiments, the TLR4 agonist comprises a synthetic GLA of Formula (IV):

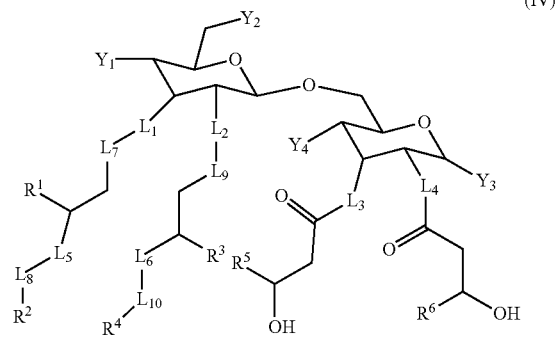

(IV)

or a pharmaceutically acceptable salt thereof, wherein:
$L_1, L_2, L_3, L_3, L_4, L_5$ and $L_6$ are the same or different and independently —O—, —NH— or —(CH$_2$)—;
$L_7, L_8, L_9,$ and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1, R_3, R_5$ and $R_6$ are the same or different and independently $C_{8-13}$ alkyl; and
$R_2$ and $R_4$ are the same or different and independently $C_{6-11}$ alkyl.

In certain embodiments, the TLR4 agonist comprises a synthetic GLA of Formula (V):

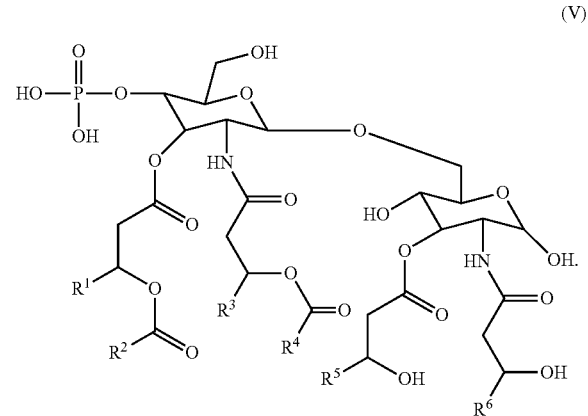

(V)

or a pharmaceutically acceptable salt thereof, wherein $R^1, R^3, R^5$ and $R^6$ are $C_{11}$-$C_{20}$ alkyl; and $R^2$ and $R^4$ are $C_{12}$-$C_{20}$ alkyl.

In certain embodiments, the TLR4 agonist comprises a synthetic GLA of formula:

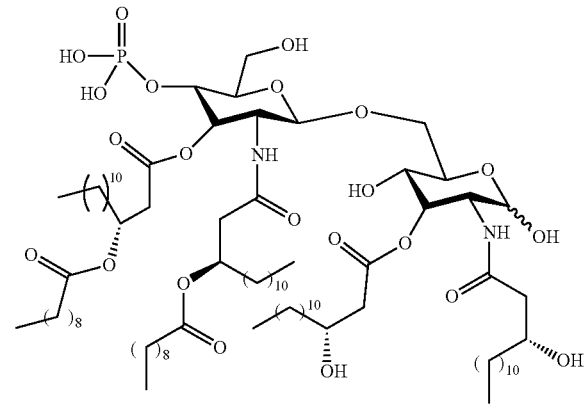

or a pharmaceutically acceptable salt thereof.

In certain embodiments, the composition further comprises an antigen. In certain embodiments, the antigen is selected from a tuberculosis-related antigen, influenza-related antigen, hemagglutinin-related antigen, cancer-related antigen, viral-related antigen and amebiasis-related antigen. In certain embodiments, the tuberculosis-related antigen is selected from the group consisting of ID93, ID91, and BCG. In certain embodiments, the influenza-related antigen is selected from the group consisting of H5N1, influenza A, influenza B, and influenza C. In certain embodiments, the amebiasis-related antigen is LecA. In certain embodiments, the viral-related antigen is selected from the group consisting of hepatitis B and hepatitis C. In certain embodiments, the composition is stable. In certain embodiments, the composition is stable for at least about six months. In certain embodiments, the composition is stable for at least about one year. In certain embodiments, the composition is stable at 2-8° C. for at least six months. In certain embodiments, the composition is stable at 2-8° C. for at least one year.

The present disclosure provides a pharmaceutical composition comprising the formulation or composition disclosed herein. In certain embodiments, the pharmaceutical composition is a vaccine. In certain embodiments, the pharmaceutical composition further comprises an antigen. In certain embodiments, the antigen is selected from a tuberculosis-related antigen, influenza-related antigen, hemagglutinin-related antigen, cancer-related antigen, viral-related antigen and amebiasis-related antigen. In certain embodiments, the tuberculosis-related antigen is selected from the group consisting of ID93, ID91, and BCG. In certain embodiments, the influenza-related antigen is selected from the group consisting of H5N1, influenza A, influenza B, and influenza C. In certain embodiments, the amebiasis-related antigen is LecA. In certain embodiments, the viral-related antigen is selected from the group consisting of hepatitis B and hepatitis C. In certain embodiments, the composition of the pharmaceutical composition is stable. In certain embodiments, the composition is stable for at least about six months. In certain embodiments, the composition is stable for at least about one year. In certain embodiments, the composition is stable at 2-8° C. for at least six months. In certain embodiments, the composition is stable at 2-8° C. for at least one year.

The present disclosure provides a method of stimulating an immune response in a subject comprising administering the formulation or composition disclosed herein to the subject and thereby stimulating an immune response in the subject. In certain embodiments, the immune response is a non-specific immune response. In certain embodiments, the immune response is an antigen-specific immune response. In certain embodiments, the immune response involves the activation of B-cells, activation of T cells, production of antibodies, or release of cytokines. In certain embodiments, the composition is used for monotherapy. In certain embodiments, the composition is used for the treatment of allergy, addiction, cancer, or autoimmunity. In certain embodiments, the composition is used for a vaccine. In certain embodiments, the route of administration of the composition is oral, intravenous, intradermal, transdermal, nasal, subcutaneous, or anal. In certain embodiments, the subject is a human. In certain embodiments, the subject is a non-human mammal. In certain embodiments, the non-human mammal is a dog, cow, or horse.

The present disclosure provides a method for preparing an aqueous formulation comprising a TLR7/8 agonist or a TLR4 agonist and a helper lipid, wherein the composition comprising the TLR7/8 agonist or a TLR4 agonist and the helper lipid comprises particles that are in a range of 1 nm to about 450 nm; wherein the method comprises (a) mixing a TLR7/8 agonist or a TLR4 agonist and a helper lipid in solvent to make solution; (b) removing the solvent from the solution of step (a) to make a film composition; and (c) rehydrating the film composition from step (c) to make a rehydrated composition; and (d) subjecting the rehydrated composition to a high energy source to make a nanosuspension composition. In certain embodiments, the high energy source is generated from a microfluidizer, an extruder, a sonicator, silverson mixer, or a homogenizer. In certain embodiments, the method further comprises mixing an antigen with the nanosuspension composition. In certain embodiments, the method further comprises mixing an aluminum salt with the nanosuspension composition. In certain embodiments, the method further comprises mixing an aluminum salt and an antigen with nanosuspension composition.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIG. 2A shows particle size and polydispersity index of 3M-052 aqueous suspensions at time of manufacture (shown is average+/−s.d. of three measurements from same sample). FIG. 2B shows particle size stability over 2 weeks for selected 3M-052 suspensions (shown is average+/−s.d. of three measurements from same sample). FIG. 2C shows zeta potential of selected 3M-052 suspensions (shown is average+/−s.d. of nine measurements from the same sample for zeta potential). FIG. 2D shows adsorption of aqueous suspensions of 3M-052 to Alhydrogel® or AdjuPhos® that were assessed by monitoring concentration of 3M-052 in centrifuged supernatant of samples containing aluminum salt compared to samples not containing aluminum salt. Samples were centrifuged for 2-3 min at 2000×g. Error bars represent standard deviation from two separate experiments using separate batches of 3M-052, where each sample from each experiment was performed in duplicate.

FIG. 3A shows intensity-based light scattering size distribution. FIG. 3B shows volume-based light scattering size distribution.

In FIG. 5A, three weeks after the first immunization, ID93-specific IgG1, IgG2c, and total IgG (IgGT) serum endpoint titers were determined by ELISA. N=4-5 mice/group. In FIG. 5B, four weeks after the final immunization, splenocytes were restimulated with media or ID93 in the presence of Brefeldin A for eight hours and the frequency of cytokine producing CD4 T cells was determined by subtracting the media response from the ID93-specific response. Data are representative of two experiments with similar results with 4-5 animals per group. Mean+/−s.e.m is shown. *p<0.05 vs. ID93, #p<0.05 vs. ID93+3M-052-AF, †p<0.05 vs. ID93+3M-052-Alum.

FIG. 6A-6D show 3M-052 dose titration. C57BL/6 mice were immunized twice three weeks apart via intramuscular injection with ID93 (0.5 ug) alone or adjuvanted with 3M-052-AF (0.1, 0.5, 1, or 10 µg), Alhydrogel®, or 3M-052-AF (0.1, 0.5, 1, or 10 µg) bound to Alhydrogel®. In FIGS. 6A and 6B, three weeks after the first immunization, ID93-specific IgG, IgG2c, and total IgG serum endpoint titers were determined by ELISA. N=5 mice/group. In FIGS. 6C and 6D, one week after the final immunization, splenocytes were restimulated with media or ID93 in the presence of Brefeldin A for eight hours and the frequency of cytokine producing CD4 T cells was determined by subtracting the media response from the ID93-specific response. Data are representative of two experiments with similar results with 5 animals per group. Mean+/−s.e.m. is shown.

In FIG. 7A. ID93-specific IgG1 and IgG2c serum antibody titers were determined three weeks after the first immunization. FIG. 7B shows ID93-specific CD4 T cells that were quantified following ex-vivo stimulation of splenocytes with ID93 one week after the second immunization. N=5 mice/group. Data are representative of two experiments with similar results with 5 animals per group. Bars indicate mean+/−s.e.m. *p<0.05.

FIG. 8A shows a protocol of an experiment. FIG. 8B shows results of three weeks after the first immunization HIV gp120 antigen-specific IgG1, IgG2c, and total IgG (IgG) serum endpoint titers that were determined by ELISA. N=5 mice/group, bars indicate mean+s.d. In FIG. 8C, one week after the second immunization, splenocytes were restimulated with HIV gp120 antigen and the frequency of cytokine producing CD4 T cells was determined by flow cytometry. N=5 mice/group, bars indicate mean+/−s.d. In FIG. 8D, three weeks after the second and third immunizations, HIV gp120 antigen-specific bone marrow antibody-secreting cells were measured by ELISPOT. N=5 mice/group, bars indicate mean+/−s.e.m. *$p<0.05$ vs. HIV gp120 antigen, #$p<0.05$ vs. 3M-052-AF, †$p<0.05$ vs. corresponding Alum (Alhydrogel® or AdjuPhos®). *$p<0.05$ vs. 3M-052-AdjuPhos®.

FIG. 9A-9D show that 3M-052 and alum synergize to augment innate responses upon immunization. Wildtype C57BL/6 mice were immunized intramuscularly with 3M-052-AF (1 µg), Alhydrogel®, AdjuPhos®, 3M-052-Alhydrogel®, or 3M-052-AdjuPhos®. Eighteen hours later the draining inguinal lymph nodes were harvested and analyzed for (FIG. 9A) influx of CD11b+Ly6C+ inflammatory monocytes, (FIG. 9B) expression of the costimulatory molecule CD86 on B cells, inflammatory monocytes or DCs (FIG. 9C) expression of CD69 on lymphocytes, and (FIG. 9D) expression of IFN-γ or IL-1b by NK cells and neutrophils, respectively. N=5 mice/group. Data are representative of two experiments with similar results with 5 animals per group. Bars indicate mean+s.e.m. *$p<0.05$ vs. none, #$p<0.05$ vs. 3M-052-AF, †$p<0.05$ vs. corresponding Alum (Alhydrogel® or AdjuPhos®), ‡$p<0.05$ vs. 3M-052-AdjuPhos®.

FIG. 11A shows a protocol of an experiment. In FIG. 11B, three weeks after the third immunization, HIV gp120 antigen-specific IgG1, IgG2c, and total IgG vaginal lavage endpoint titers were determined by ELISA. N=9-10 mice/group, bars indicate mean+/−s.d. In FIG. 11C, one week following each immunization, splenocytes were restimulated with HIV gp120 antigen and the frequency of cytokine producing CD4 T cells was determined by flow cytometry. N=5 mice/group, bars indicate mean+/−s.e.m. *$p<0.05$ vs. HIV gp120 antigen, #$p<0.05$ vs. 3M-052-AF, †$p<0.05$ vs. corresponding Alum (Alhydrogel® or AdjuPhos®), ‡$p<0.05$ vs. 3M-052-AdjuPhos®.

DETAILED DESCRIPTION OF THE INVENTION

Figure 1:
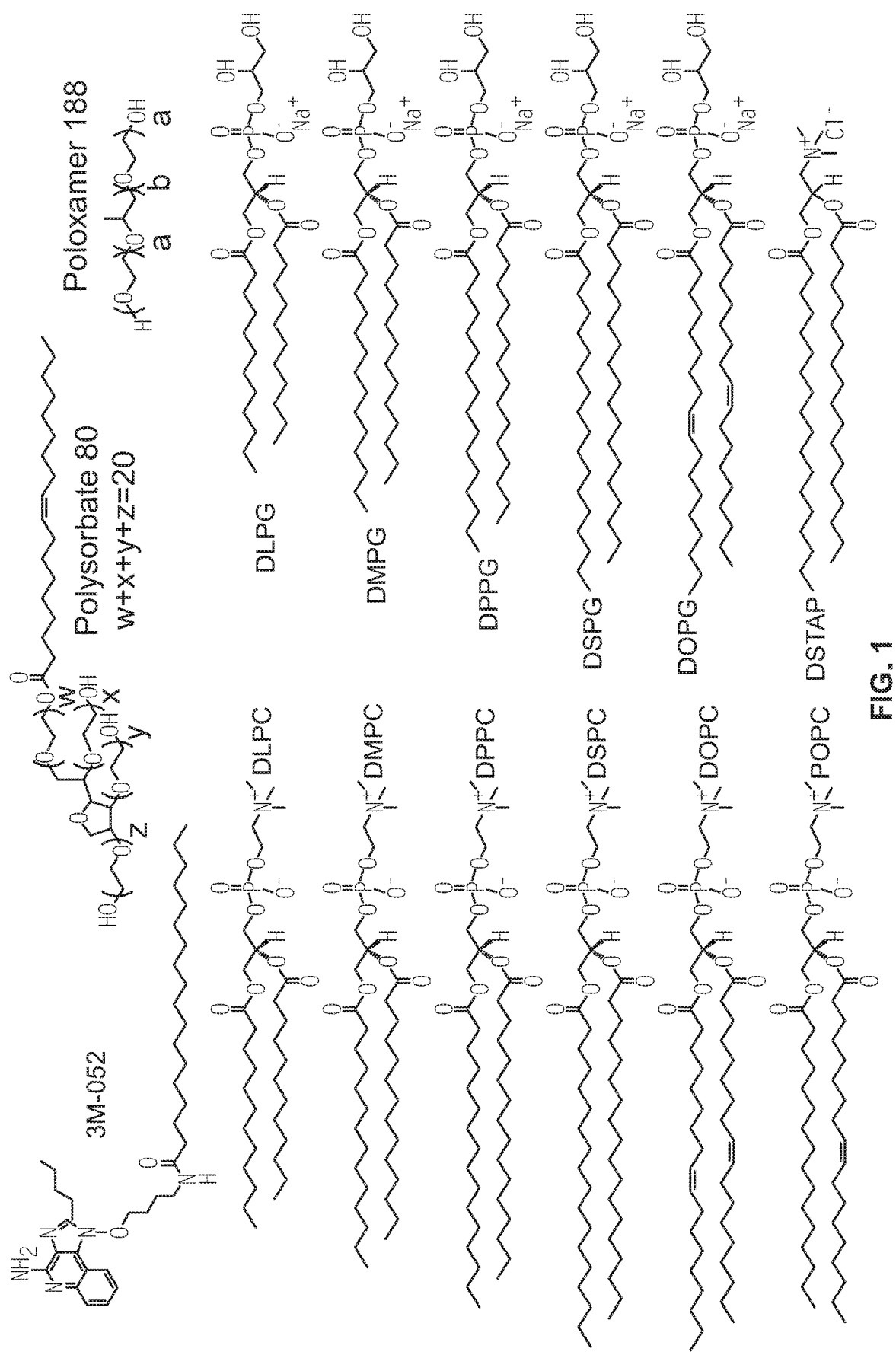
FIG. 1 shows structures of 3M-052 and various phospholipids.

The present disclosure relates to a composition comprising a TLR7/8 agonist or a TLR 4 agonist and a helper lipid, wherein the composition is suitable for binding with an aluminum salt in an aqueous solution. The present disclosure provides an aqueous formulation comprising a TLR7/8 agonist or a TLR 4 agonist and a helper lipid. The present disclosure also provides stable aqueous composition of adjuvant comprising a TLR7/8 agonist or a TLR4 agonist with a helper lipid that is adsorbed to an aluminum salt.

Absorption of TLR ligands to aluminum salts may result in more localized delivery and facilitate enhanced adjuvant activity. However, the structure of certain TLR agonists may not enable effective adsorption to alum. The present disclosure relates to a composition of a lipid-based composition comprising a TLR agonist that facilitates adsorption to an aluminum salt via a helper lipid.

The present disclosure provides for potentiation of the physiochemical structural compatibility of TLR agonists with alum and/or antigens through the formulation of a TLR agonist with a helper lipid to produce a stable aqueous formulation. The preparation of a stable aqueous formulation or nanosuspension is facilitated through an input of energy (e.g., sonication or microfluidization) through which the particles of TLR agonist and helper lipid can be sized to about 450 nm or less. The aqueous formulation or nanosuspension is stable at about 2-8C for at least about 1 week, 2 weeks, 4 weeks, 3 months, 6 months, 9 months, or 1 year. An aqueous formulation or nanosuspension is a composition of a TLR agonist and a helper lipid, in which the composition is a dispersion of TLR agonist and a helper lipid that is stable for a predetermined time period, as disclosed herein.

Compositions (such as vaccine compositions, pharmaceutical compositions) comprising the aqueous formulation described herein are also provided. In some embodiments, the compositions are useful for stimulating an immune response in a subject. In some embodiments, the composition described herein further comprises one or more antigens.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The following terms have the following meanings unless otherwise indicated. Any undefined terms have their art recognized meanings.

"Alkyl" means a straight chain or branched, noncyclic or cyclic, unsaturated or saturated aliphatic hydrocarbon containing from 1 to 20 carbon atoms, and in certain preferred embodiments containing from 11 to 20 carbon atoms. Representative saturated straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Halo" or "halogen" refers to fluoro, chloro, bromo, and iodo.

"Hydroxy" or "hydroxyl" refers to the group —OH.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Acylamino" refers to the groups —NR$^{20}$C(O)R$^{21}$, wherein R$^{20}$ and R$^{21}$ are independently selected from hydrogen, alkyl, and aryl.

"Acid functional group" means a functional group capable of donating a proton in aqueous media (i.e. a Brønsted-Lowry acid). After donating a proton, the acid functional group becomes a negatively charged species (i.e. the conjugate base of the acid functional group). Examples of acid functional groups include, but are not limited to: —OP(=O)(OH)$_2$ (phosphate), —OS(=O)(OH)$_2$ (sulfate), —OS(OH)$_2$ (sulfite), —C(=O)OH (carboxylate), —OC(=O)CH(NH$_2$)CH$_2$C(=O)OH (aspartate). —OC(=O)CH$_2$CH$_2$C(=O)OH (succinate), and —OC(=O)CH$_2$OP(=O)(OH)$_2$ (carboxymethylphosphate).

Compositions

The present disclosure provides an aqueous formulation comprising a TLR agonist and a helper lipid. In certain embodiments, the aqueous formulation or nanosuspension comprising a TLR agonist and a helper lipid is admixed with an aluminum salt. In some embodiments, the compositions described herein can further comprise one or more agents or antigens.

The present disclosure provides an aqueous formulation comprising (1) a TLR7/8 agonist or a TLR4 agonist and (2) a helper lipid. In certain embodiments, a composition comprising the TLR7/8 agonist and the helper lipid is subjected to a high energy source to produce an aqueous formulation or a nanosuspension composition. In certain embodiments, a composition comprising the TLR4 agonist and the helper lipid is subjected to a high energy source to produce an aqueous formulation or a nanosuspension composition. In the certain embodiments, the aqueous formulation or nanosuspension composition comprises particles that range in size from about 1 nm to 450 nm, such as less than about 400 nm or less than about 200 nm.

In certain embodiments, the aqueous formulation or nanosuspension comprising a TLR7/8 agonist or a TLR4 agonist and a helper lipid is admixed with an aluminum salt. The present disclosure provides a composition comprising (1) a TLR7/8 agonist; (2) a helper lipid; and (3) an aluminum salt. The present disclosure provides a composition comprising (1) a TLR4 agonist; (2) a helper lipid; and (3) an aluminum salt.

In some embodiments, the compositions described herein can further comprise one or more agents or antigens. The present disclosure provides an aqueous formulation comprising (1) a TLR7/8 agonist or a TLR4 agonist and (2) a helper lipid, further comprising one or more agents or antigens. The present disclosure provides an aqueous composition comprising (1) a TLR7/8 agonist or a TLR4 agonist; (2) a helper lipid; and (3) an aluminum salt, further comprising one or more agents or antigens. The present disclosure provides an aqueous composition comprising (1) a TLR7/8 agonist; (2) a helper lipid; and (3) an aluminum salt, further comprising one or more agents or antigens. The present disclosure provides an aqueous composition comprising (1) a TLR4 agonist; (2) a helper lipid; and (3) an aluminum salt, further comprising one or more agents or antigens.

Description of the components of the aqueous composition is provided below.

TLR Agonists

In some embodiments, the TLR agonists described herein are hydrophobic or relatively hydrophobic and in the absence of a helper lipid do not substantially form stable aqueous nanosuspensions of the present disclosure when mixed with water either in the presence or absence of an input from a high energy source. In some embodiments, the TLR agonists of the present disclosure contain nonpolar moieties such as hydrocarbon chains. In some embodiments, the TLR agonists of the present disclosure are soluble in the organic solvents but are poorly soluble or insoluble in water and have a tendency to array into large aggregates in aqueous solutions in the absence of the helper lipids of the present disclosure. Physicochemical properties of TLR agonists are described in Membrane Structural Biology: With Biochemical and Biophysical Foundations by Mary Luckey, Cambridge University Press, New York, 2014, which is herein incorporated by reference in its entirety.

As used herein, "insoluble in water" refers to a compound that does not dissolve when the compound is mixed with water, for example, when mixed with water at room temperature, for example, between or between about 25° C. and 50° C. As used herein, "low solubility in water" refers to a compound that has a solubility in water of less than or about 30 mg/mL, for example, when mixed with water at room temperature, such as between or between about 25° C. and 50° C. As used herein, "poorly soluble in water" can be used to refer to compounds, for example, non-polar compounds, that are water insoluble or have low water solubility.

TLR7/8 Agonists

Provided herein are TLR7/8 agonists that can be used in the compositions described herein. As used herein, a "TLR7/8 agonist" refers to an agonist that affects its biological activities through its interaction with TLR7, TLR8, or both. Such biological activities include, but are not limited to, the induction of TLR7 and/or TLR8 mediated signal transduction to potentiate immune responses via the innate immune system. In some embodiments, the TLR is an imidazoquinoline amine derivative (see. e.g., U.S. Pat. No. 4,689,338 (Gerster)), but other compound classes are known as well (see, e.g., U.S. Pat. No. 5,446,153 (Lindstrom et al.); U.S. Pat. No. 6,194,425 (Gerster et al.); and U.S. Pat. No. 6,110,929 (Gerster et al.); and International Publication Number WO2005/079195 (Hays et al.)).

In certain embodiments, the TLR7/8 agonist is a compound of following structure of Formula (I):

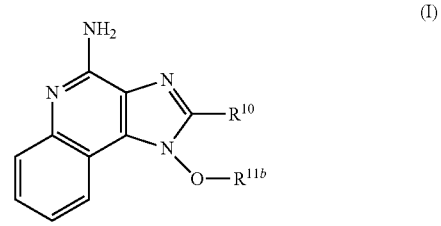

or a pharmaceutically acceptable salt thereof, wherein:
R$^{10}$ is selected from the group consisting of hydrogen and C$_{1-6}$alkyl; and
R$^{11b}$ is C$_{1-6}$alkyl optionally substituted with one or more groups selected from the group consisting of halo, hydroxyl. C$_{1-6}$alkoxy, and acylamino.

In some embodiments of Formula (I), $R^{10}$ is hydrogen. In some embodiments, $R^{10}$ is $C_{1-6}$alkyl. In some embodiments, $R^{10}$ is methyl, ethyl, n-propyl, or n-butyl. In some embodiments, $R^{10}$ is n-butyl.

In some embodiments of Formula (I), $R^{11b}$ is $C_{2-4}$alkyl, which is substituted with acylamino. In some embodiments, $R^{11b}$ is —(CH$_2$)$_4$-acylamino. In some embodiments, $R^{11b}$ is —(CH$_2$)$_4$—NH—C(O)—C$_{1-25}$alkyl. In some embodiments, $R^{11b}$ is —(CH$_2$)$_4$—NH—C(O)—C$_{15-25}$alkyl. In some embodiments, $R^{11b}$ is —(CH$_2$)$_4$—NH—C(O)—C$_{15-20}$alkyl. In some embodiments, $R^{11b}$ is —(CH$_2$)$_4$—NH—C(O)—C$_{17}$alkyl.

In certain embodiments, the TLR7/8 agonist is a compound of the following structure or pharmaceutically acceptable salts thereof:

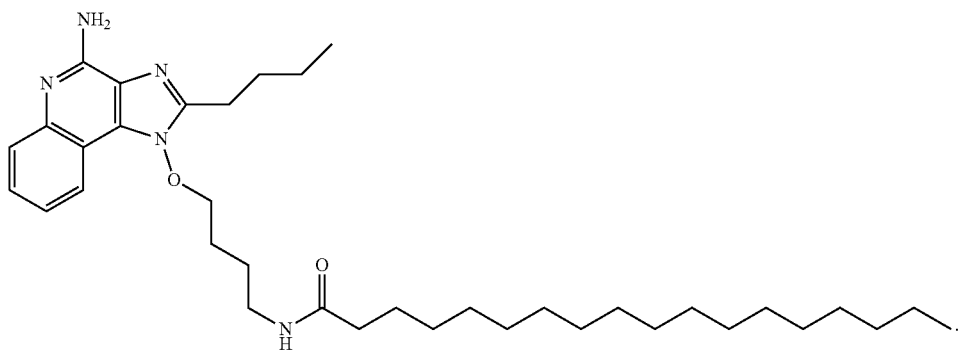

(3M-052)

In certain preferred embodiments, a TLR7/8 agonist used in the compositions herein comprises a N-(4-{[4-amino-2-butyl-1H-imidazo[4,5-c]quinolin-1-yl]oxy}butyl)octadecanamide), 3M-052 as described in U.S. Pat. No. 9,242,980.

TLR4 Agonists

In certain preferred embodiments, a TLR4 agonist used in the compositions herein comprises a glucopyranosyl lipid adjuvant (GLA), such as those described in U.S. Patent Publication Nos. US2007/021017, US2009/045033, US2010/037466, and US 2010/0310602, the contents of which are incorporated herein by reference in their entireties.

For example, in certain embodiments, the TLR4 agonist is a synthetic GLA adjuvant having the following structure of Formula (II):

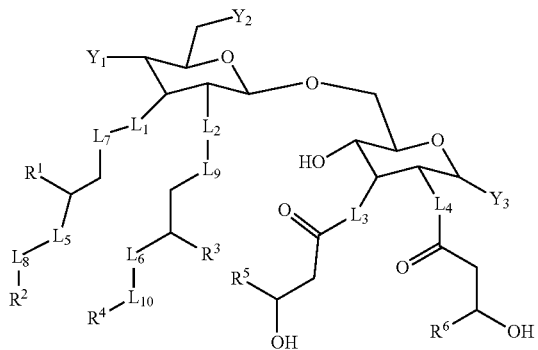

(II)

or a pharmaceutically acceptable salt thereof, wherein:
$L_1$, $L_2$, $L_3$, $L_4$, $L_5$ and $L_6$ are the same or different and independently —O—, —NH— or —(CH$_2$)—;
$L_7$, $L_8$, $L_9$, and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_{8-13}$ alkyl; and
$R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl. In certain embodiments, $R^1$, $R^3$, $R^5$ and $R^6$ are $C_{11}$ alkyl; and $R^2$ and $R^4$ are $C_9$ alkyl.

For example, in certain embodiments, the TLR4 agonist is a synthetic GLA adjuvant having the following structure of Formula (III) or a pharmaceutically acceptable salt thereof:

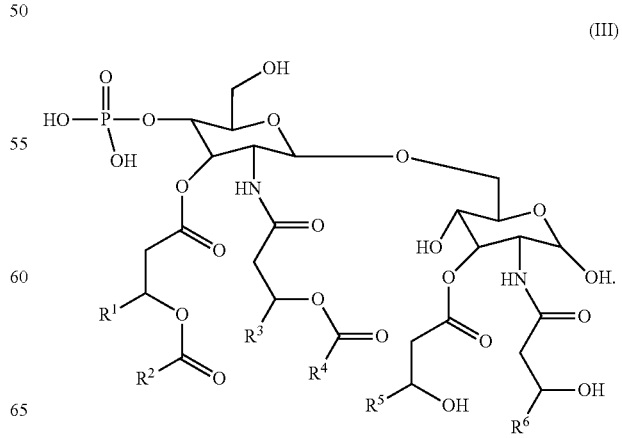

(III)

In certain embodiments of the above GLA structure, $R^1$, $R^3$, $R^5$ and $R^6$ are $C_{11}$-$C_{20}$ alkyl; and $R^2$ and $R^4$ are $C_{12}$-$C_{20}$ alkyl. In another specific embodiment, the GLA has the formula set forth above wherein $R^1$, $R^3$, $R^5$ and $R^6$ are $C_{11}$ alkyl; and $R^2$ and $R^4$ are $C_{13}$ alkyl. In another specific embodiment, the GLA has the formula set forth above wherein $R^1$, $R^3$, $R^5$ and $R^6$ are $C_{10}$ alkyl; and $R^2$ and $R^4$ are $C_8$ alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (IV) or a pharmaceutically acceptable salt thereof:

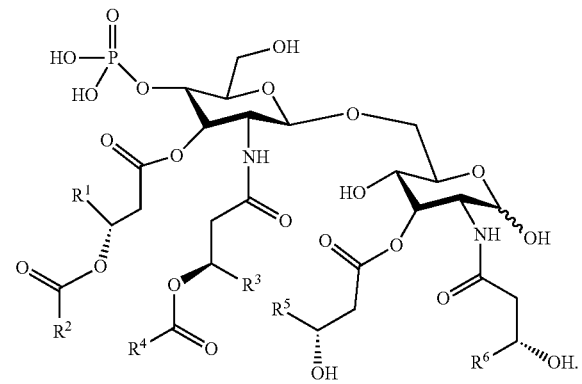

(IV)

In certain embodiments of the above GLA structure. $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (V):

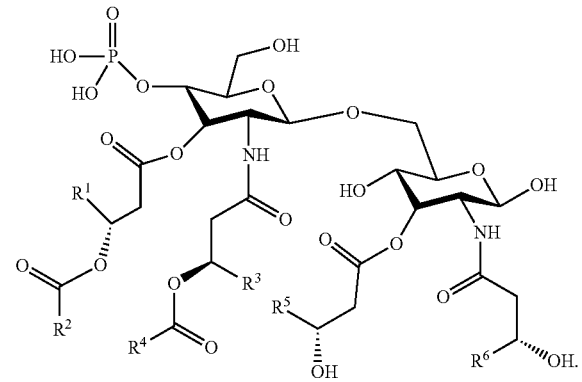

(V)

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^1$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (VI) or a pharmaceutically acceptable salt thereof:

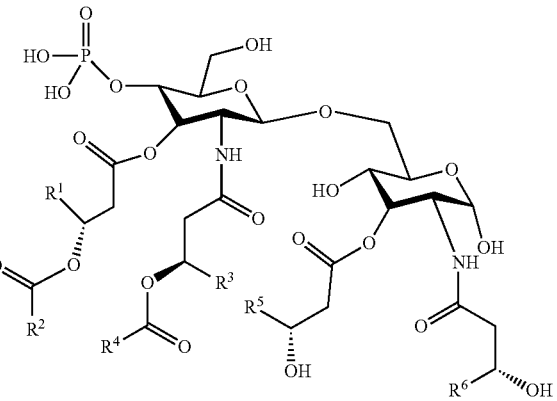

(VI)

In certain embodiments of the above GLA structure. $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure or a pharmaceutically acceptable salt thereof:

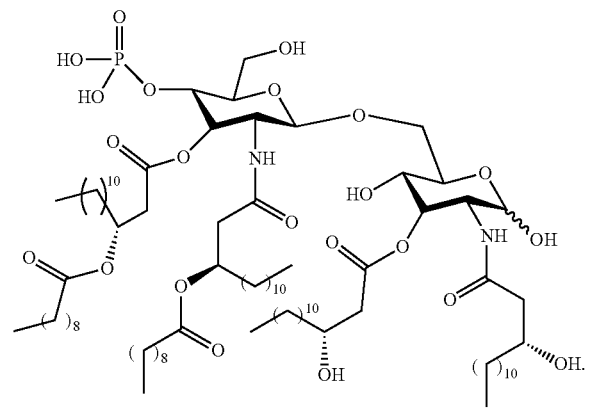

In certain embodiments, the TLR4 agonist is a synthetic GLA adjuvant having the following structure or a pharmaceutically acceptable salt thereof:

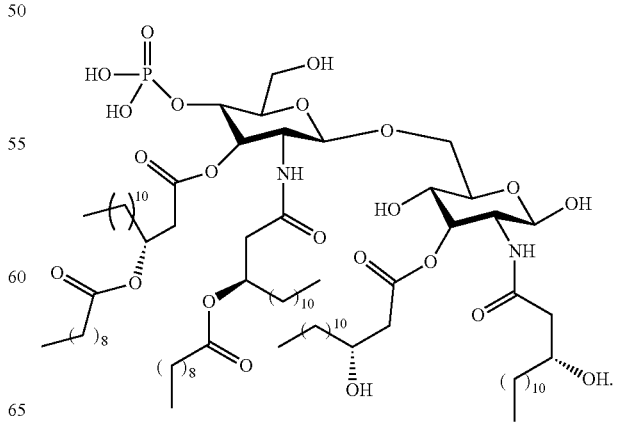

In certain embodiments, the TLR4 agonist is a synthetic GLA adjuvant having the following structure or a pharmaceutically acceptable salt thereof:

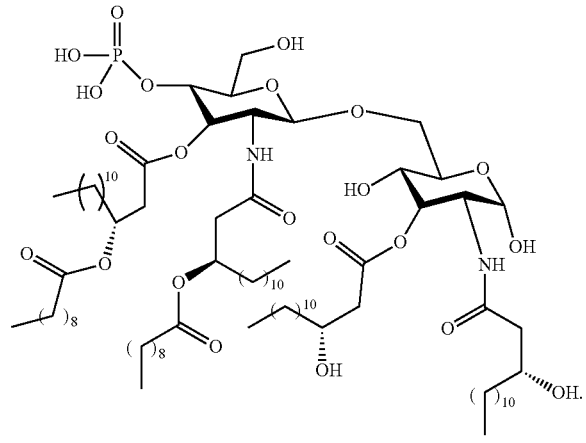

In another embodiment, an attenuated lipid A derivative (ALD) is incorporated into the compositions described herein. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$). ALDs useful according to the present disclosure include monophosphoryl lipid A (MLA or MPL) and 3-deacylated monophosphoryl lipid A (3D-MLA or 3D-MPL). MLA (MPL) and 3D-MLA (3D-MPL) are known and need not be described in detail herein. See, for example, U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi Immuno-Chem Research. Inc., embodies 3-deacylated monophosphoryl lipid A and a method for its manufacture. Also, see for example, GB 2220211 and WO 92/116556. 3 De-O-acylated monophosphoryl lipid A is known from GB 2220211 (Ribi). Chemically it is a mixture of 3 De-O-acylated monophosphoryl lipid A with 4, 5 or 6 acylated chains and is manufactured by Ribi Immunochem Montana. A certain form of 3 De-O-acylated monophosphoryl lipid A is disclosed in International Patent Application No. WO 92/116556. Disclosures of each of these patents with respect to MLA and 3D-MLA are incorporated herein by reference.

In the TLR4 agonist compounds above, the overall charge can be determined according to the functional groups in the molecule. For example, a phosphate group can be negatively charged or neutral, depending on the ionization state of the phosphate group.

In any of the embodiments provided herein, the TLR4 agonist is a synthetic GLA adjuvant having the structure of Formula (III) or a pharmaceutically acceptable salt thereof wherein $R^1$, $R^3$, $R^5$ and $R^6$ are $C_{11}$ alkyl; and $R^2$ and $R^4$ are $C_{13}$ alkyl.

Helper Lipid

Provided herein are helper lipids that can be used in the compositions described herein.

In certain embodiments, the helper lipid is a phospholipid or a quaternary ammonium salt lipid. In certain embodiments, the helper lipid is a phospholipid that is a phosphatidylcholine or a phosphoglyceride. In certain embodiments, the helper lipid comprises any of the following moieties:

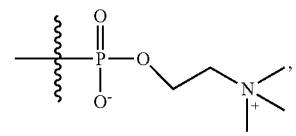

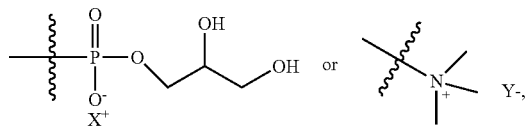

wherein $X^-$ is an alkali metal counterion and $Y^+$ is a halide counterion.

In certain embodiments, the helper lipid comprises a $C_{10-20}$ alkyl chain. In certain embodiments, the helper lipid comprises a $C_{12-18}$ alkyl chain.

In certain embodiments, the helper lipid is anionic. In certain embodiments, the helper lipid is cationic. In certain embodiments, the helper lipid is overall neutrally charged. In certain embodiments, the helper lipid is a zwitterion.

In certain embodiments, suitable helper lipids are shown below.

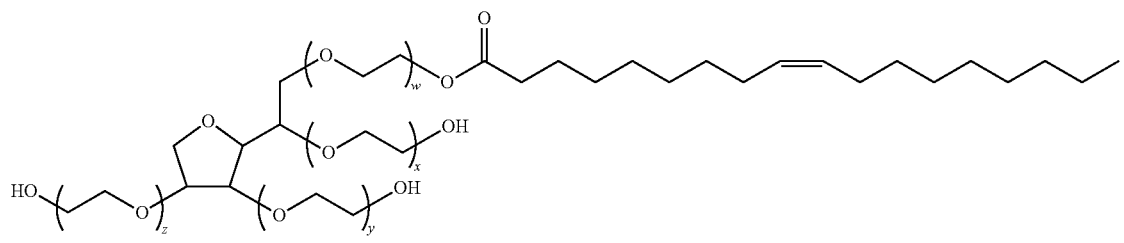

w + x + y + z = 20

Polysorbate 80

-continued
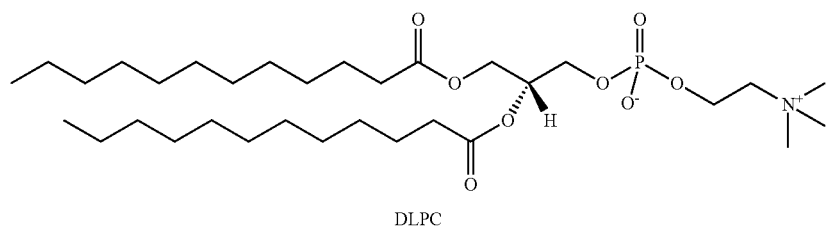
DLPC
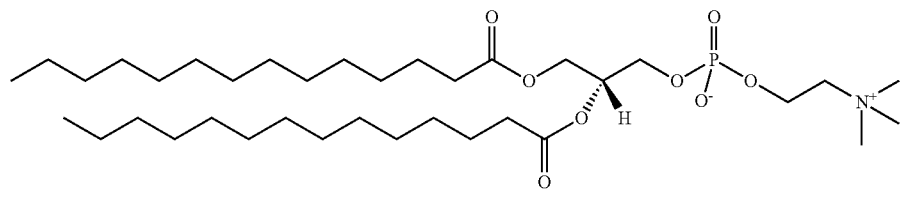
DMPC
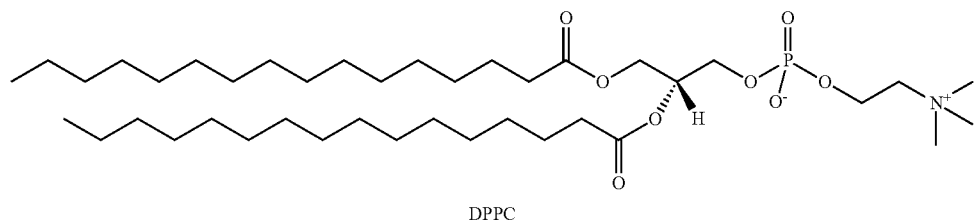
DPPC
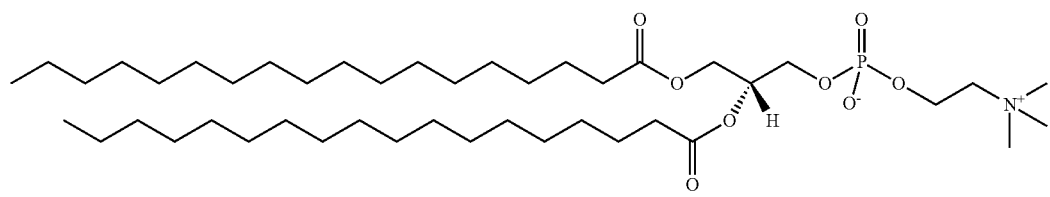
DSPC
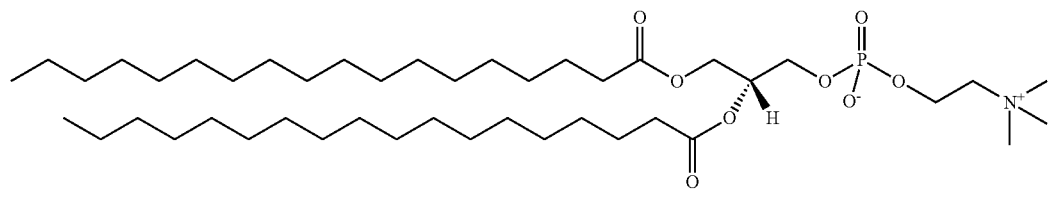
DOPC
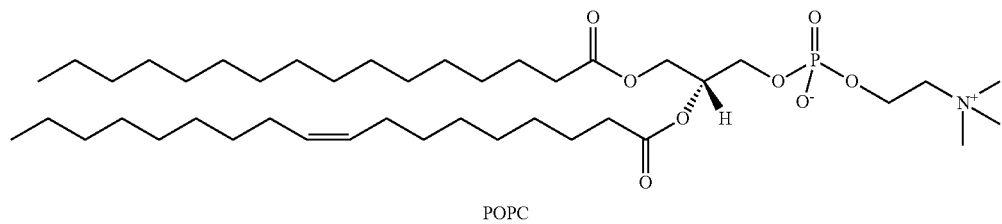
POPC
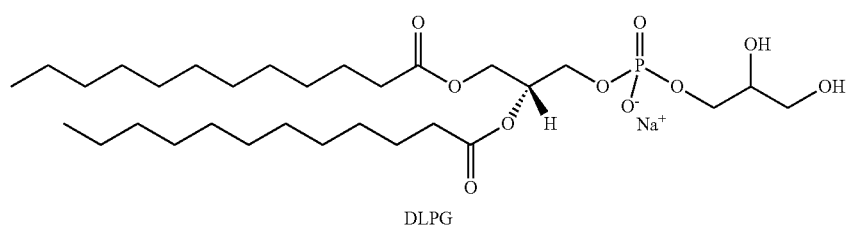
DLPG

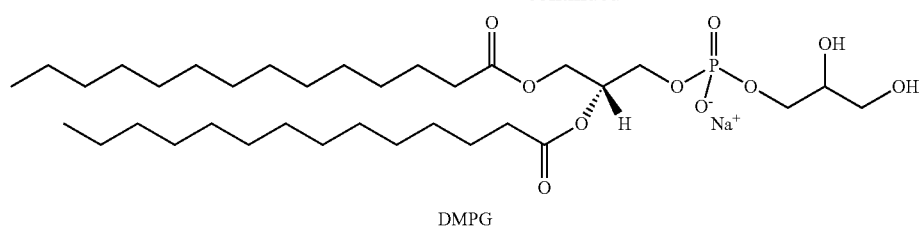
DMPG
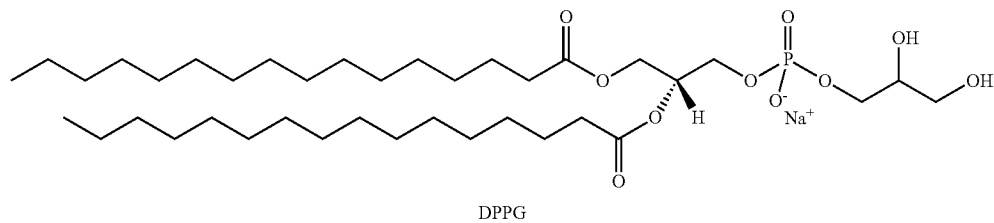
DPPG
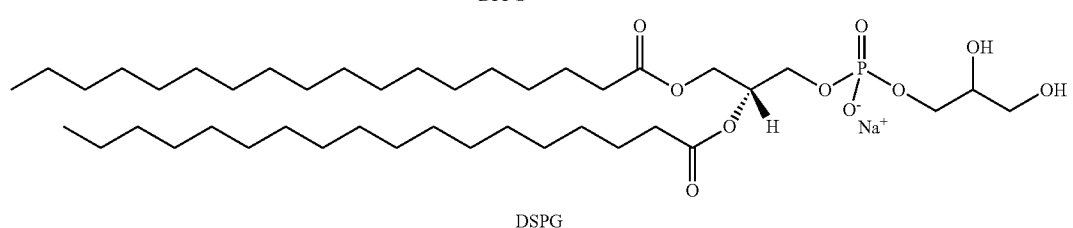
DSPG
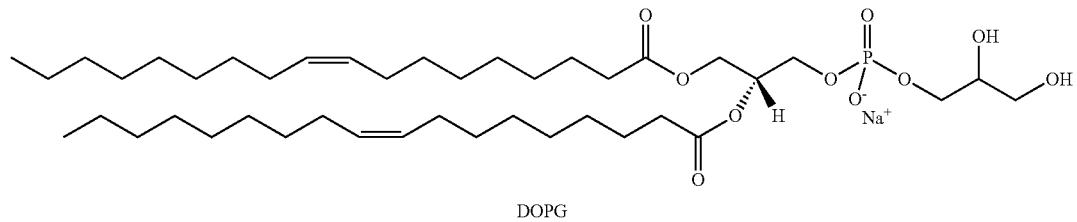
DOPG
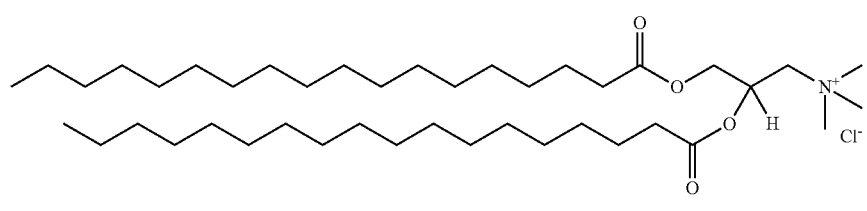
DSTAP
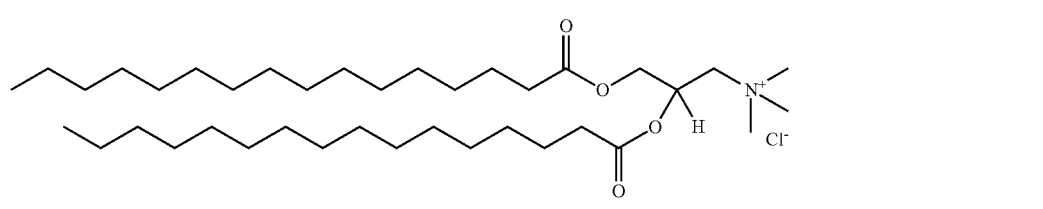
DPTAP
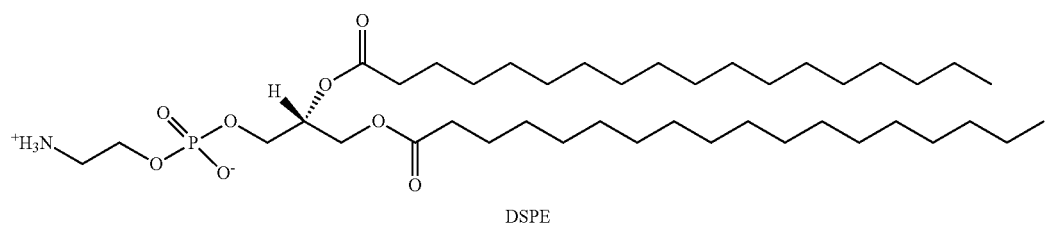
DSPE

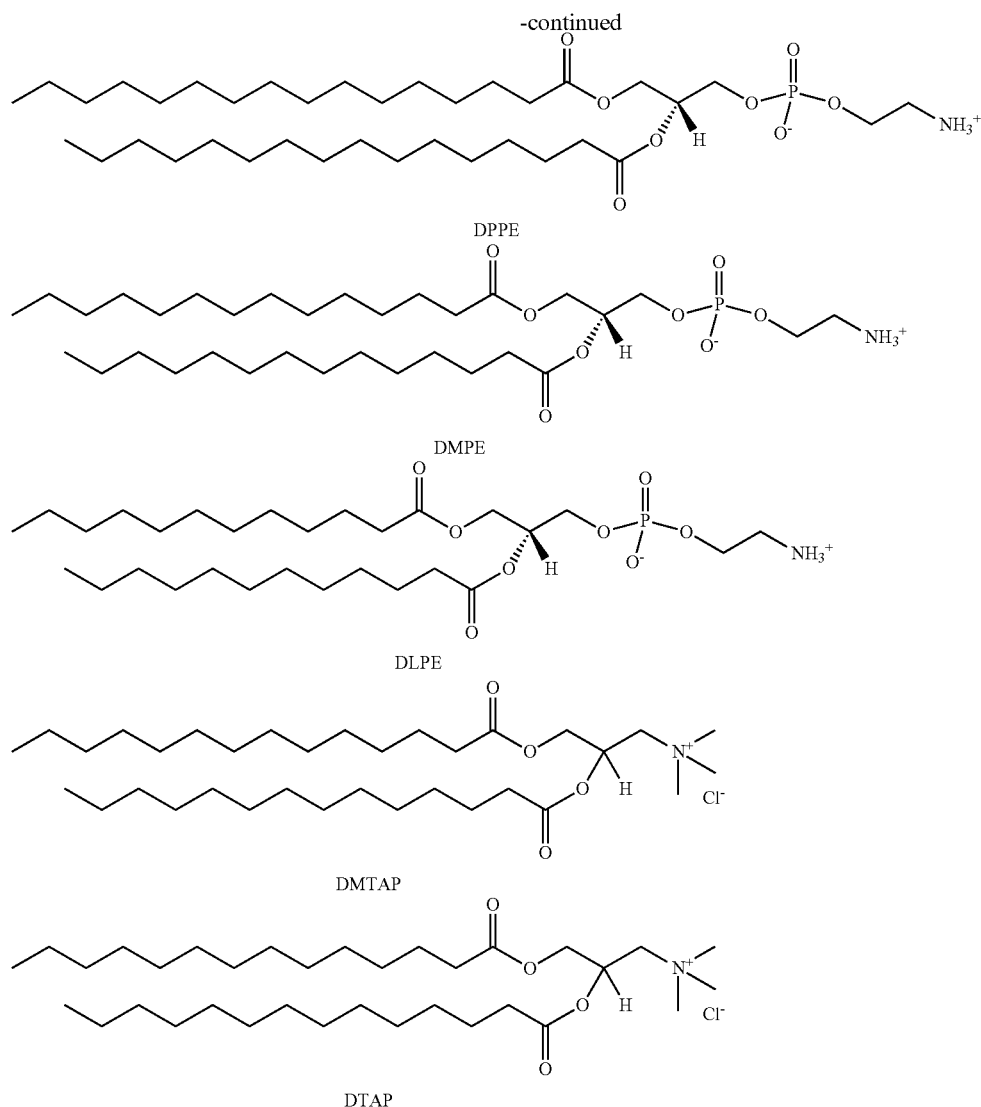

In certain embodiments, the helper lipid is selected from DLPG, DMPG, DPPG, DSPG, DOPG, DSTAP, and DVTAP. In certain embodiments, the helper lipid is selected from DLPG, DMPG, DPPG, DSPG, and DOPG. In certain embodiments, the helper lipid is selected from DSTAP and DPTAP.

In certain embodiments, the helper lipid is DSPG. In certain embodiments, the helper lipid is DSTAP. In certain embodiments, the helper lipid is DPTAP.

In certain embodiments, the helper lipid is selected from DSPG and DSTAP. In certain embodiments, the helper lipid is selected from DSPG and DSTAP. In certain embodiments, the helper lipid is DSPG. In certain embodiments, the helper lipid is DSTAP.

In certain embodiments, the helper lipid is selected from DLPC, DMPC, DPPC, DSPC, DOPC, and POPC. In certain embodiments, the helper lipid is selected from DLPC, DSPC, and DOPC.

In certain embodiments, the helper lipid is selected from DPPC and DPTAP. In certain embodiments, the helper lipid is DPPC. In certain embodiments, the helper lipid is DPTAP.

In certain embodiments, the helper lipid is selected from DOPC, DSPG. DSTAP, and Polysorbate 80.

In any of the embodiments described herein, the helper lipid can be DLPE.

In any of the embodiments described herein, the helper lipid can be DMTAP.

In any of the embodiments described herein, the helper lipid can be DTAP.

Aluminum Salt

As noted above, the compositions described herein can comprise an aluminum salt, which can be referred to herein as alum. Suitable aluminum salts include aluminum hydroxide, aluminum trihydrate, aluminum oxyhydroxide, aluminum phosphate, aluminum hydroxyphosphate, aluminum hydroxyphosphate sulfate, and potassium aluminum sulfate. Aluminum salts can also be referred to by the formulae: $Al(OH)_3$, $AlH_3O_3$, $AlH_6O_3$, $AlO(OH)$, $Al(OH)(PO_4)$, and $KAl(SO_4)_2$. Aluminum salts used as co-adjuvants are advantageous because they have a good safety record, augment antibody responses, stabilize antigens, and are relatively simple for large-scale production. (Edelman 2002 *Mol. Biotechnol.* 21:129-148; Edelman, R. 1980 *Rev. Infect. Dis.* 2:370-383.)

In certain embodiments, the aluminum salt is Alhydrogel®, an aluminum hydroxide or aluminum oxyhydroxide. Alhydrogel® has an overall positive charge and can readily adsorb negatively charged moieties. Alhydrogel® can also be referred to as Amphojel; Aluminum hydroxide gel; Hydrated alumina; Aluminum trihydroxide; or Alugelibye.

In certain embodiments, the aluminum salt is AdjuPhos®, an aluminum phosphate. AdjuPhos® has an overall negative charge and can readily adsorb positively charged moieties.

Aqueous Formulation of TLR Agonist and Helper Lipid

As noted above, the present disclosure provides an aqueous formulation comprising (1) a TLR agonist and (2) a helper lipid. The present disclosure provides an aqueous formulation comprising (1) a TLR7/8 agonist or a TLR4 agonist and (2) a helper lipid.

In certain embodiments, the present disclosure provides an aqueous formulation comprising (1) a TLR7/8 agonist and (2) a helper lipid. In certain embodiments, the aqueous formulation comprises a TLR 7/8 agonist and helper lipid selected from the group consisting of DOPC, DSPG, DSTAP, and Polysorbate 80. In certain embodiments, the aqueous formulation comprises a TLR 7/8 agonist and helper lipid selected from the group consisting of DSPG and DSTAP.

In certain embodiments, the present disclosure provides an aqueous formulation comprising (1) a TLR4 agonist and (2) a helper lipid. In certain embodiments, the present disclosure provides an aqueous formulation comprising (1) a TLR4 agonist and (2) a helper lipid that is DPTAP.

In certain embodiments, a composition comprising the TLR agonist and the helper lipid is subjected to a high energy source to produce an aqueous formulation or nanosuspension composition. In certain embodiments, a composition comprising the TLR7/8 agonist or a TLR4 agonist and the helper lipid is subjected to a high energy source to produce an aqueous formulation or nanosuspension composition. In the certain embodiments, the aqueous formulation comprises nanosuspension particles of TLR agonist and helper lipid that are range in size from about 1 nm to 450 nm, such as less than about 400 nm or less than about 200 nm.

Size

In some embodiments the size of the nanosuspension particle ranges from about 50 nm to 75 nm. In some embodiments the size of the nanosuspension particle ranges from about 50 nm to 100 nm. In some embodiments the size of the nanosuspension particle ranges from about 50 nm to 150 nm. In some embodiments the size of the nanosuspension particle ranges from about 50 nm to 200 nm. In some embodiments the size of the nanosuspension particle ranges from about 20 nm to 100 nm. In some embodiments the size of the nanosuspension particle ranges from about 20 nm to 50 nm. In some embodiments the size of the nanosuspension particle ranges from about 10 nm to 200 nm. In some embodiments the size of the nanosuspension particle ranges from about 10 nm to 100 nm. In some embodiments the size of the nanosuspension particle ranges from about 10 nm to 50 nm. In some embodiments the size of the nanosuspension particle is about 1 nm, is about 5 nm, is about 10 nm, is about 15 nm, is about 20 nm, is about 25 nm, is about 30 nm, is about 35 nm, is about 40 nm, is about 45 nm, is about 50 nm, is about 55 nm, is about 60 nm, is about 65 nm, is about 70 nm, is about 75 nm, is about 80 nm, is about 85 nm, is about 90 nm, is about 95 nm, is about 100 nm, is about 105 nm, is about 110 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, or is about 200 nm. In some embodiments, the size of the nanosuspension particle is no greater than about 1 nm, no greater than about 5 nm, no greater than about 10 nm, no greater than about 15 nm, no greater than about 20 nm, no greater than about 25 nm, no greater than about 30 nm, no greater than about 35 nm, no greater than about 40 nm, no greater than about 45 nm, no greater than about 50 nm, no greater than about 55 nm, no greater than about 60 nm, no greater than about 65 nm, no greater than about 70 nm, no greater than about 75 nm, no greater than about 80 nm, no greater than about 85 nm, no greater than about 90 nm, no greater than about 95 nm, no greater than about 100 nm, no greater than about 105 nm, no greater than about 110 nm, no greater than about 115 nm, no greater than about 120 nm, no greater than about 125 nm, no greater than about 130 nm, no greater than about 135 nm, no greater than about 140 nm, no greater than about 145 nm, no greater than about 150 nm, no greater than about 155 nm, no greater than about 160 nm, no greater than about 165 nm, no greater than about 170 nm, no greater than about 175 nm, no greater than about 180 nm, no greater than about 185 nm, no greater than about 190 nm, no greater than about 195 nm, or no greater than about 199 nm.

In some embodiments, the size of the nanosuspension particle of TLR agonist and helper lipid is no greater than about 200 nm, no greater than about 205 nm, no greater than about 10 nm, no greater than about 215 nm, no greater than about 220 nm, no greater than about 225 nm, no greater than about 230 nm, no greater than about 235 nm, no greater than about 240 nm, no greater than about 245 nm, no greater than about 250 nm, no greater than about 255 nm, no greater than about 260 nm, no greater than about 265 nm, no greater than about 270 nm, no greater than about 275 nm, no greater than about 280 nm, no greater than about 285 nm, no greater than about 90 nm, no greater than about 295 nm, no greater than about 300 nm, no greater than about 305 nm, no greater than about 310 nm, no greater than about 315 nm, no greater than about 320 nm, no greater than about 325 nm, no greater than about 130 nm, no greater than about 335 nm, no greater than about 140 nm, no greater than about 145 nm, no greater than about 150 nm, no greater than about 355 nm, no greater than about 360 nm, no greater than about 365 nm, no greater than about 370 nm, no greater than about 375 nm, no greater than about 380 nm, no greater than about 385 nm, no greater than about 390 nm, no greater than about 395 nm, or no greater than about 399 nm, no greater than about 400 nm; no greater than about 405 nm, no greater than about 410, nm no greater than about 415 nm, no greater than about 420 nm, no greater than about 425 nm, no greater than about 430 nm, no greater than about 435 nm, no greater than about, 440 nm, no greater than about 440 nm no greater than about 445 nm, or no greater than about 450 nm.

In some embodiments, the nanosuspension particle is capable of being filtered through at least a 0.45 micron filter. In some embodiments, the nanosuspension particle is capable of being filtered through a 0.45 micron or smaller pore size filter. In some embodiments, the nanosuspension particle is capable of being filtered through a 0.45 micron filter. In some embodiments, the nanosuspension particle is capable of being filtered through a 0.20 micron filter. In some embodiments, the nanosuspension particle is capable of being filtered through a 0.22 micron filter.

Stability

In some embodiments provided herein, the 1-450 nm size of the aqueous nanosuspension particle comprising the TLR agonist (e.g., TLR7/8 agonist or a TLR4 agonist) and a helper lipid is stable, in that the nanosuspension particle's size of less than 450 nm is maintained, and in that the particle exhibits reduced aggregation, or no aggregation, when compared to a TLR agonist in the absence of a helper lipid of the present disclosure.

In some embodiments, "stable" refers to a formulation or composition comprised of nanosuspension particles which displays little to no aggregation, or reduced aggregation or demonstrate little to no overall increase in average particle size or polydispersity of the formulation over time compared to the initial particle size.

The stability of the nanosuspension particle can be measured by techniques familiar to those of skill in the art. In some embodiments, the stability is observed visually. Visual inspection can include inspection for particulates, flocculence, or aggregates. In some embodiments, the stability is determined by the size of the nanosuspension particle. For example, the size can be assessed by known techniques in the art, including but not limited to, x-ray and laser diffraction, dynamic light scattering (DLS). CryoEM, or Malvern Zetasize. In some embodiments, the size of the nanosuspension particle refers to the Z-average diameter. In some embodiments, the stability is assessed by the ability of the nanosuspension particle to pass through a filter of a particular size, for example through a 0.20, 0.22 or 0.45 micron filter. In some embodiments, stability is determined by pH. In some embodiments, stability is determined by measurement of the polydispersity index (PdI), for example with the use of the dynamic light scattering (DLS) technique.

In some embodiments, the Z-average diameter of the nanosuspension particle increases less than 50%, less than 40%, less than 30%, less than 25%, less than 20%, less than 15%, less than 12%, less than 10%, less than 7%, less than 5%, less than 3%, less than 1% over time period assayed.

In some embodiments, the nanosuspension particle is stable at 0-8° C., such as 2-8° C. In some embodiments, the nanosuspension particle is stable at 0° C., 1° C., 2° C., 3° C. 4° C. 5° C., 6° C. 7° C., or 8° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanosuspension particle is stable at 20-30° C. In some embodiments, the nanosuspension particle is stable at 25° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanosuspension particle is stable at 35-40° C. In some embodiments, the nanosuspension particle is stable at 35° C., 36° C., 37° C. 38° C., 39° C., or 40° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanosuspension particle is stable at 57-62° C. In some embodiments, the nanosuspension particle is stable at 57° C., 58° C., 59° C., 60° C., 61° C., or 62° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month.

In one exemplary embodiment, the nanosuspension particle is stable at 2-8° C. for at least 2 weeks, 3 weeks, 1 month, 2 months, 3 months, 4 months, 5 months, 6 months, 7 months, 8 months, 9 months, 10 months, 11 month, or one year.

In some embodiments, the nanosuspension particle is stable after 1-4 freeze thaws. In some embodiments, the nanosuspension particle is stable after 1, after 2, after 3, or after 4 freeze thaws.

Combination of TLR Agonist, Helper Lipid, and Aluminum Salt

As noted above, a stable aqueous formulation of adjuvant comprising a TLR agonist with a helper lipid that are adsorbed to an aluminum salt is provided. The present disclosure provides a stable aqueous formulation of adjuvant comprising a TLR7/8 agonist or a TLR4 agonist with a helper lipid that are adsorbed to an aluminum salt.

In certain embodiments, the present disclosure provides an aqueous composition comprising (1) a TLR7/8 agonist; (2) a helper lipid; and (3) an aluminum salt. In certain embodiments, the aqueous formulation comprises (1) a TLR 7/8 agonist; (2) helper lipid selected from the group consisting of DOPC, DSPG, DSTAP, and Polysorbate 80; and (3) an aluminum salt. In certain embodiments, the aqueous formulation comprises (1) a TLR 7/8 agonist; (2) helper lipid selected from the group consisting of DSPG and DSTAP; and (3) an aluminum salt.

In certain embodiments, the present disclosure provides an aqueous composition comprising (1) a TLR4 agonist; (2)

a helper lipid; and (3) an aluminum salt. In certain embodiments, the present disclosure provides an aqueous composition comprising (1) a TLR4 agonist; (2) a helper lipid that is DPTAP; and (3) an aluminum salt. In certain embodiments, the present disclosure provides an aqueous composition comprising (1) a TLR4 agonist; (2) a helper lipid; and (3) an aluminum salt that is aluminum phosphate (e.g., AdjuPhos®). In certain embodiments, the present disclosure provides an aqueous composition comprising (1) a TLR4 agonist; (2) a helper lipid that is DPTAP; and (3) an aluminum salt that is aluminum phosphate (e.g., AdjuPhos®).

The factors that relate to the selection of each of the components include, but are not limited to, the charges of the components and presence of exchangeable ligands. With proper selection of the components, the TLR agonist and helper lipid is suitable to be adsorbed to the aluminum salt. In certain embodiments, the adsorption occurs with in vitro conditions.

Binding or adsorption refers to an interaction between molecules or portions thereof that exhibit mutual affinity or binding capacity, typically due to specific or non-specific binding or interaction, including, but not limited to, biochemical, physiological, and/or chemical interactions. In certain embodiments, binding to an aluminum salt can be determined by UV spectroscopy, SDS-PAGE, or centrifugation studies.

In some embodiments, at least 25%, at least 40%, at least 50%, at least 65%, at least 70%, at least 75%, at least 80%, at least 85%, at least 90%, at least 95%, at least 97%, at least 99%, of the TLR agonist with helper lipid present in the composition is associated with alum particles. One exemplary method of determining the percent association is demonstrated in Example 1.

Adsorption onto an aluminum salt can take place generally, but not limited to, by the following mechanisms: electrostatic interaction and ligand exchange. Electrostatic interaction uses the presence of opposite charges on the components under a certain solution condition. Ligand exchange uses a phosphate group in one of the components to exchange with a hydroxyl group of another component. For ligand exchange, accessible phosphate groups and hydroxyl groups in the components are used. To prepare a vaccine composition with an antigen in combination with the adjuvant composition comprising TLR agonist, helper lipid, and aluminum salt, there is consideration of the charge and presence of phosphate groups and hydroxyl groups on the antigen.

Ligand Exchange

In certain embodiments with respect to the ligand exchange mechanism, there may be ligand exchange between the antigen and adjuvant composition comprising TLR agonist, helper lipid, and aluminum salt.

In certain embodiments, there may be ligand exchange between the components of the adjuvant composition (e.g., TLR agonist, helper lipid, and aluminum salt). As noted above, certain components in the adjuvant composition comprise phosphate groups while other certain components comprise hydroxyl groups, thus enabling ligand exchange. For example, certain TLR4 agonists comprise phosphate groups. Also, certain helper lipids comprise phosphate groups. Also, AdjuPhos® comprises phosphate groups.

Hydroxyl groups are present in the following components: antigens, TLR agonists, helper lipid, and Alhydrogel®.

Electrostatic Interaction

In certain embodiments with respect to the electrostatic interaction mechanism, a vaccine composition is substantially neutrally charged at about physiological pH.

If the antigen for a vaccine composition is charged, the components for the adjuvant composition (e.g., TLR agonist, helper lipid, and aluminum salt) can be selected to neutralize the charge of the antigen to provide a substantially neutrally charged vaccine composition. If the antigen for the vaccine composition is substantially neutrally charged, the components for the adjuvant composition (e.g., TLR agonist, helper lipid, and aluminum salt) can be selected to maintain the substantially neutral charge of the antigen to provide a substantially neutrally charged vaccine composition. As noted above, each of the components in the adjuvant composition can be characterized by negatively charged, positively charged, or neutrally charged.

In certain embodiments, a formulation composition comprises a TLR agonist, a helper lipid, and an aluminum salt, wherein the components are selected with the features from the table below.

| TLR agonist | Helper lipid | Aluminum salt | Antigen |
|---|---|---|---|
| Substantially neutrally charged | Sufficient to solubilize TLR agonist | Comprises charge to neutralize charge from antigen | Comprises charge to neutralize charge from aluminum salt |
| Positively charged | Sufficient to solubilize composition | Comprises charge to neutralize charge from TLR agonist and antigen | Comprises charge |

In certain embodiments, a formulation composition comprises a TLR agonist, a helper lipid, and an aluminum salt, wherein the components are selected from the table below.

| TLR agonist | Helper lipid | Aluminum salt |
|---|---|---|
| TLR7/8 agonist (e.g. 3M-052) | DSPG DLPG DMPG DPPG DOPG | Alhydrogel ® |
| TLR7/8 agonist (e.g. 3M-052) | DSPG | Alhydrogel ® |
| TLR7/8 agonist (e.g. 3M-052) | DSTAP | AdjuPhos ® |
| TLR4 agonist (e.g., GLA) | DPPC | Alhydrogel ® |
| TLR4 agonist (e.g., GLA) | DPTAP | AdjuPhos ® |
| TLR4 agonist (e.g., GLA) | DSTAP, DMTAP, DTAP | AdjuPhos ® |

Process of Making Compositions

The present disclosure provides a process for preparing an aqueous formulation comprising a TLR agonist (e.g., TLR7/8 agonist or a TLR4 agonist) and a helper lipid; wherein the method comprises
    (a) mixing a TLR agonist (e.g., TLR7/8 agonist or a TLR4 agonist) and a helper lipid in solvent to make solution;
    (b) removing the solvent from the solution of step (a) to make a film composition; and (c) rehydrating the film composition from step (c) to make a rehydrated composition; and (d) subjecting the rehydrated composition to a high energy source to make a nanosuspension composition.

In some embodiments, the solvent has a low boiling point. Solvents that are suitable for the process include, but not limited to, chloroform, methylene chloride, methanol, and water. In certain embodiments, the solvent is chloroform. In certain embodiments, the solvent comprises chloroform, methanol, and water.

In certain embodiments, the mixing of a TLR7/8 agonist or a TLR4 agonist and a helper lipid can be in a ratio of about 1:2 of the TLR7/8 agonist or the TLR4 agonist to helper lipid.

The mixing of the components in step (a) can be performed at room temperature or with light heating. Light heating can be heating up to 30, 35, or 40 OC.

In step (b) of the process, the solvent is removed with light heating or reduced pressure. In some embodiments, the solvent is removed with reduced pressure. Reduced pressure is a pressure that is lower than atmospheric pressure.

In step (c), the film composition is rehydrated. A suitable solvent for rehydration is water. In certain embodiments, the water is ultrapure water.

In step (d), the rehydrated composition is subjected to a high energy source to make a nanosuspension composition. In certain embodiments, the rehydrated composition is agitated. A method of agitation is sonication. The sonication can occur for up to several hours. In certain embodiments, the agitation is continued until the composition is translucent. In certain embodiments, the agitation is continued until the composition is with substantially no visible particles. In some embodiments, a solution is translucent as evidenced by a reading by UV spectroscopy, a turbidimeter, or dynamic light scattering.

In step (d), the rehydrated composition can processed or milled. Processing or milling occurs using standard techniques known in the art including sonication, silverson mixing, and microfluidization.

In some embodiments the high energy source provides at least 2,000 PSI, at least 3,000, 5,000 PSI, at least 10,000 PSI, at least 15,000 PSI at least 20,000 PSI, at least 25,000 PSI, at least 30,000 PSI, at least 35,000 PSI, at least 40,000 PSI, at least 45,000 PSI, or at least 50,000 PSI. In some embodiments the high energy source provides about 5,000 to 50.000; 5,000 to 10.000; 5.000 to 15.000; 5,000 to 20,000; 5,000 to 25,000; 5,000 to 30,000; 5,000 to 35,000; 5.000 to 40.000; 5.000 to 45.000; or 5.000 to 50000 PSI. In some embodiments the high energy source provides about 45,000 to 50,000; 40,000 to 50,000; 35,000 to 50,000; 30,000 to 50,000; 25,000 to 50,000; 20,000 to 50,000; 15.000 to 50.000; 10.000 to 50,000; or 5.000 to 50.000 PSI.

In some embodiments the high energy source provides about 25.000 to 35.000; 25,000 to 30,000; or 30,000 to 35,000 PSI. In some embodiments the high energy source provides about 30,000 PSI.

In some embodiments, the high energy source is a high shear source.

In some embodiments the high energy source is a microfluidizer. Microfluidization is used to describe a process in which compositions are exposed to high shear force. In some embodiments, the compositions are processed by an instrument or a device known as a MICROFLUIDIZER®.

In some embodiments the high energy source is an extruder.

In some embodiments the high energy source is a sonicator.

In some embodiments the high energy source is a homogenizer.

In some embodiments the composition is subjected to least 1, 2, 3, 4, 5, 6, 7, 8, 9, 10, 15, 20, 25, 30, 50, or 100 passes of the high shear force. In some embodiments the composition is subjected to 1-5, 6-10, 11-15, 16-20, 21-30, 31-40, 41-50, 51-60, 61-70, 71-80, 81-90, or 91-100 passes of the high shear force. In some embodiments the composition subjected to 3, 6, or 10 passes of the high shear force.

In the certain embodiments, the size of the nanosuspension particle ranges in size from about 1 nm to 450 nm, such as less than about 400 nm or less than about 200 nm.

In some embodiments the size of the nanosuspension particle ranges from about 50 nm to 75 nm. In some embodiments the size of the nanosuspension particle ranges from about 50 nm to 100 nm. In some embodiments the size of the nanosuspension particle ranges from about 50 nm to 150 nm. In some embodiments the size of the nanosuspension particle ranges from about 50 nm to 200 nm. In some embodiments the size of the nanosuspension particle ranges from about 20 nm to 100 nm. In some embodiments the size of the nanosuspension particle ranges from about 20 nm to 50 nm. In some embodiments the size of the nanosuspension particle ranges from about 10 nm to 200 nm. In some embodiments the size of the nanosuspension particle ranges from about 10 nm to 100 nm. In some embodiments the size of the nanosuspension particle ranges from about 10 nm to 50 nm. In some embodiments the size of the nanosuspension particle is about 1 nm, is about 5 nm, is about 10 nm, is about 15 nm, is about 20 nm, is about 25 nm, is about 30 nm, is about 35 nm, is about 40 nm, is about 45 nm, is about 50 nm, is about 55 nm, is about 60 nm, is about 65 nm, is about 70 nm, is about 75 nm, is about 80 nm, is about 85 nm, is about 90 nm, is about 95 nm, is about 100 nm, is about 105 nm, is about 110 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, or is about 200 nm. In some embodiments, the size of the nanosuspension particle is no greater than about 1 nm, no greater than about 5 nm, no greater than about 10 nm, no greater than about 15 nm, no greater than about 20 nm, no greater than about 25 nm, no greater than about 30 nm, no greater than about 35 nm, no greater than about 40 nm, no greater than about 45 nm, no greater than about 50 nm, no greater than about 55 nm, no greater than about 60 nm, no greater than about 65 nm, no greater than about 70 nm, no greater than about 75 nm, no greater than about 80 nm, no greater than about 85 nm, no greater than about 90 nm, no greater than about 95 nm, no greater than about 100 nm, no greater than about 105 nm, no greater than about 110 nm, no greater than about 115 nm, no greater than about 120 nm, no greater than about 125 nm, no greater than about 130 nm, no greater than about 135 nm, no greater than about 140 nm, no greater than about 145 nm, no greater than about 150 nm no greater than about 155 nm, no greater than about 160 nm, no greater than about 165 nm, no greater than about 170 nm, no greater than about 175 nm, no greater than about 180 nm, no greater than about 185 nm, no greater than about 190 nm, no greater than about 195 nm, or no greater than about 199 nm.

The aqueous formulation can be further mixed with an aluminum salt, as described herein.

The aqueous formulation can be further mixed with an antigen, as described herein.

The aqueous formulation can be further mixed with an aluminum salt and an antigen, as described herein.

The present disclosure provides for products made by any of the above processes.

The present disclosure provides for a nanosuspension composition made by
(a) mixing a TLR agonist (e.g., TLR7/8 agonist or a TLR4 agonist) and a helper lipid in solvent to make solution;
(b) removing the solvent from the solution of step (a) to make a film composition; and
(c) rehydrating the film composition from step (c) to make a rehydrated composition; and
(d) subjecting the rehydrated composition to a high energy source to make a nanosuspension composition.

The present disclosure provides for a nanosuspension composition made by steps (a) to (d) above, further comprising mixing the nanosuspension composition with an aluminum salt; mixing the nanosuspension composition with an antigen; or mixing the nanosuspension composition with an aluminum salt and an antigen.

Agents

The aqueous formulation provided herein may further comprise one or more agents, wherein the agent can be a polypeptide, a polynucleotide, an antigen, an adjuvant, a diagnostic agent, a therapeutic agent, an organism, a genome, or a virus. In some embodiments, the aqueous formulation comprises two or more agents. In some embodiments, the agent is associated with the aqueous formulation. In some embodiments, the agent is associated with the aqueous formulation by ligand exchange and/or by an electrostatic (charge-based) interaction.

Polypeptides

In some embodiments the agent is a polypeptide. In some embodiments the polypeptide is a full length protein or a fragment thereof. In some embodiments the polypeptide is a peptide. In some embodiments, the polypeptide is a fusion protein. In some particular embodiments, the fusion protein is capable of eliciting an immune response upon administration to an individual. In some embodiments, the polypeptide is an antigen, as further described below.

Antigens

In one embodiment, the agent comprises an antigen.

In some embodiments the polypeptide antigen is involved in, or derived from, an allergy, cancer, or infectious disease.

In some embodiments the compositions described herein are useful for vaccination purposes, and are provided as vaccine formulations (vaccine compositions).

An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Certain embodiments contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (MFV), cytomegalovirus. Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. viva, P. malariae* and *P. ovale*; or another parasite such as one or more of *Acanthamoeba, Entamoeba histolytica, Angiostrongylus, Schistosoma mansonii, Schistosoma haematobium. Schistosoma japonicum, Cryptosporidium, Ancylostonua, Entamoeba histolytica, Entamoeba coli, Entamoeba dispar, Entamoeba hartmanni, Entamoeba polecki, Wuchereria bancrofti, Giardia*, and *Leishmania*. In specific embodiments, the antigen may be from, or related to antigens involved in tuberculosis, influenza, amebiasis, HIV, hepatitis, or Leishmaniasis.

In some embodiments, the antigen is an amebiasis-related antigen. In some embodiments, the antigen is an amebiasis-causing antigen. In some embodiments, the antigen is from an amebiasis causing organism. In some embodiments, the antigen is from *Entamoeba histolytica*. In one embodiment, the antigen comprises LecA. In one embodiment, the antigen is LecA.

In some embodiments, the antigen is an influenza-related antigen. In some embodiments, the antigen is an influenza-causing antigen. In some embodiments, the antigen is from an influenza causing virus. In one embodiment, the antigen comprises H5N1. In one embodiment, the antigen comprises H5N1.

For example, in certain embodiments, antigens are derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

In certain embodiments the antigen is derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof). Rotavirus (including live-attenuated viruses), Epstein Barr virus (such as gp350 or derivatives thereof), Varicella Zoster Virus (such as gpl, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus. Japanese Encephalitis Virus) or Influenza virus (whole live or inactivated virus, split influenza virus, or MDCK cells, or whole flu virosomes (as described by Gluck, Vaccine, 1992, 10, 915-920) or purified or recombinant proteins thereof, such as HA, NP, NA, or M proteins, or combinations thereof).

In certain other embodiments, the antigen is derived from one or more bacterial pathogens such as Neisseria spp, including N. gonorrhea and N. meningitidis (for example capsular polysaccharides and conjugates thereof, transferrin-binding proteins, lactoferrin binding proteins, PilC, adhesins); S. pyogenes (for example M proteins or fragments thereof, C5A protease, lipoteichoic acids), S. agalactiae. S. mutans: H. ducreyi; Moraxella spp, including M. catarrhalis, also known as Branhamella catarrhalis (for example high and low molecular weight adhesins and invasins); Bordetella spp, including B. pertussis (for example pertactin, pertussis toxin or derivatives thereof, filamentous hemagglutinin, adenylate cyclase, fimbriae), B. parapertussis and B. bronchiseptica; Mycobacterium spp., including M. tuberculosis (for example ESAT6, Antigen 85A, —B or —C), M. bovis, M. leprae, M. avium, M. paratuberculosis, M. smegmatis; Legionella spp, including L. pneumophila; Escherichia spp, including enterotoxic E. coli (for example colonization factors, heat-labile toxin or derivatives thereof, heat-stable toxin or derivatives thereof), enterohemorragic E. coli, enteropathogenic E. coli (for example shiga toxin-like toxin or derivatives thereof); Vibrio spp. including V. cholera (for example cholera toxin or derivatives thereof); Shigella spp, including S. sonnei, S. dysenteriae, S. flexnerii; Yersinia spp, including Y. enterocolitica (for example a Yop protein), Y. pestis, Y. pseudotuberculosis; Campylobacter spp. including C. jejuni (for example toxins, adhesins and invasins) and C. coli; Salmonella spp, including S. typhi, S. paratyphi, S. choleraesuis, S. enteritidis; Listeria spp., including L. monocytogenes; Helicobacter spp. including H. pylori (for example urease, catalase, vacuolating toxin); Pseudomonas spp. including P. aeruginosa; Staphylococcus spp., including S. aureus. S. epidermidis; Enterococcus spp., including E. faecalis, E. faecium; Clostridium spp., including C. tetani (for example tetanus toxin and derivative thereof), C. botulinum (for example botulinum toxin and derivative thereof), C. difficile (for example clostridium toxins A or B and derivatives thereof); Bacillus spp., including B. anthracis (for example botulinum toxin and derivatives thereof); Corynebacterium spp., including C. diphtheriae (for example diphtheria toxin and derivatives thereof); Borrelia spp., including B. burgdorferi (for example OspA, OspC, DbpA, DbpB), B. garinii (for example OspA, OspC, DbpA, DbpB), B. afzelii (for example OspA, OspC, DbpA, DbpB), B. andersonii (for example OspA, OspC, DbpA, DbpB), B. hermsii; Ehrlichia spp., including E. equi and the agent of the Human Granulocytic Ehrlichiosis; Rickettsia spp, including R. rickettsii; Chlamydia spp. including C. trachomatis (for example MOMP, heparin-binding proteins), C. pneumoniae (for example MOMP, heparin-binding proteins), C. psittaci; Leptospira spp., including L. interrogans; Treponema spp., including T. pallidum (for example the rare outer membrane proteins), T. denticola, T. hyodysenteriae; or other bacterial pathogens.

In certain other embodiments, the antigen is derived from one or more parasites (See, e.g., John, D. T, and Petri, W. A., Markell and Voge's Medical Parasitology—9th Ed., 2006, W B Saunders, Philadelphia; Bowman, D. D., Georgis' Parasitology for Veterinarians—8th Ed., 2002, W B Saunders, Philadelphia) such as Plasmodium spp., including P. falciparum; Toxoplasma spp., including T. gondii (for example SAG2, SAG3, Tg34); Entamoeba spp., including E. histolytica; Babesia spp., including B. microti; Trypanosoma spp., including T. cruzi; Giardia spp., including G. lamblia; Leshmania spp., including L. major; Pneumocystis spp., including P. carinii; Trichomonas spp., including T. vaginalis; or from a helminth capable of infecting a mammal, such as: (i) nematode infections (including, but not limited to, Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis, and Strongyloides stercoralis); (ii) trematode infections (including, but not limited to, Schistosoma mansoni, Schistosoma haematobium, Schistosoma japonicum, Schistosoma mekongi, Opisthorchis sinensis, Paragonimus sp, Fasciola hepatica, Fasciola magna, Fasciola gigantica); and (iii) cestode infections (including, but not limited to, Taenia saginata and Taenia solium). In certain embodiments, the antigen is derived from Schisostoma spp., Schistosoma mansonii, Schistosoma haematobium, and/or Schistosoma japonicum, or derived from yeast such as Candida spp., including C. albicans; Cryptococcus spp., including C. neoformans.

Other specific antigens are derived from M. tuberculosis, for example Th Ra12, Tb H9, Tb Ra35, Th38-1. Erd 14, DPV, MTI, MSL, mTTC2 and hTCC1 (WO 99/51748). Proteins for M. tuberculosis also include fusion proteins and variants thereof where at least two, three, or four or more, polypeptides of M. tuberculosis are fused into a larger protein. Certain fusions include Ra12-TbH9-Ra35, Erd14-DPV-MTI, DPV-MTI-MSL. Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647. In one exemplary embodiment, the fusion protein is ID93. In one exemplary embodiment, the fusion protein is ID91.

Other specific antigens are derived from Chlamydia, and include for example the High Molecular Weight Protein (HWMP) (WO 99/17741), ORF3 (EP 366 412), and putative membrane proteins (Pmps). Other Chlamydia antigens can be selected from the group described in WO 99128475. Certain antigens may be derived from Streptococcus spp. including S. pneumoniae (for example capsular polysaccharides and conjugates thereof, PsaA, PspA, streptolysin, choline-binding proteins) and the protein antigen Pneumolysin (Biochem Biophys Acta. 1989, 67, 1007; Rubins et al., Microbial Pathogenesis, 25, 337-342), and mutant detoxified derivatives thereof (WO 90/06951; WO 99/03884). Other bacterial vaccines comprise antigens derived from Haemophilus spp., including H. influenzae type B (for example PRP and conjugates thereof), non typeable H. influenzae, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Other specific antigens fare derived from Hepatitis B. Derivatives of Hepatitis B Surface antigen are well known in the art and include, inter alia, those PreS1, Pars2 S antigens set forth described in European Patent applications EP-A414 374; EP-A-0304 578, and EP 198474. In one aspect antigen is HIV-1 gp120, especially when expressed in CHO cells. In a further embodiment, the antigen is gD2t.

In other embodiments, the antigen is derived from the Human Papilloma Virus (HPV) considered to be responsible for genital warts (HPV 6 or HPV 11 and others), and the HPV viruses responsible for cervical cancer (HPV 16. HPV 18 and others). Particular antigens include L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and proteinD(1/3)-E7 disclosed in GB 9717953.5 (PCT/EP98/05285). Additional possible antigens include HPV 16 or 18 antigens. For example, L1 or L2 antigen monomers, or L1 or L2 antigens presented together as a virus like particle (VLP) or the L1 alone protein presented alone in a VLP or capsomer structure. Such antigens, virus like particles and capsomer are per se known. See for example WO94/00152, WO94/20137. WO94/05792, and WO93/02184.

In other embodiments, the antigen is a fusion protein. Fusion proteins may be included alone or as fusion proteins such as E7, E2 or F5 for example; particular embodiments include a VLP comprising LIE7 fusion proteins (WO 96/11272). Particular HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, for example a Protein D-E6/E7 fusion. Compositions may optionally contain either or both E6 and E7 proteins front HPV 18, for example in the form of a Protein D-E6 or Protein D-E7 fusion protein or Protein D E6/E7 fusion protein. Compositions may additionally comprise antigens from other HPV strains, for example from strains HPV 31 or 33.

Antigens may also be derived from parasites that cause Malaria. For example, antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXPI, Pfs25, Pfs28, PFS27125, Pfs16, Pfs48/45, Pfs230 and their analogues in *Plasmodium* spp.

In one embodiment, the antigen is derived from a cancer cell, as may be useful for the immunotherapeutic treatment of cancers. For example, the antigen may be a tumor rejection antigen such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 *Current Opinions in Immunology* 8, pps 628-636; Van den Eynde et al., *International Journal of Clinical & Laboratory Research* (1997 & 1998); Correale et al. (1997), *Journal of the National Cancer Institute* 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are include, but are not restricted to, tumor-specific or tumor-associated gangliosides such as $GM_2$, and $GM_3$ or conjugates thereof to carrier proteins; or a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., *Proc. Nat. Acad. Sci. USA* 95(4) 1735-1740 1998), PSMA or, in one embodiment an antigen known as Prostase. (e.g., Nelson, et al., *Proc. Natl. Acad. Sci. USA* (1999) 96: 3114-3119; Ferguson, et al, *Proc. Natl. Acad. Sci. USA* 1999, 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (*PNAS* 96 14523 14528 7-12 1999).

Other tumor associated antigens useful in the context of the present invention include: Plu-1 (*J Biol. Chem* 274 (22) 15633-15645, 1999). HASH-1, HasH-2. Cripto (Salomon et al *Bioessays* 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

In certain embodiments, the compositions of the present disclosure will be particularly applicable in treatment of the elderly and/or the immunosuppressed, including subjects on kidney dialysis, subjects on chemotherapy and/or radiation therapy, transplant recipients, and the like. Such individuals generally exhibit diminished immune responses to vaccines and therefore use of the compositions of the present disclosure can enhance the immune responses achieved in these subjects.

In other embodiments, the agents used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g. pneumococcal) infection (Clin Microbiol Rev. 2001 April; 14(2):336-63).

Polynucleotides

In some embodiments the agent is a polynucleotide. A polynucleotide includes, but is not limited to a DNA, an RNA, an aptamer, and an oligonucleotide. In some embodiments the polynucleotide is DNA. In some embodiments the polynucleotide is RNA. In some embodiments, the DNA or RNA is single stranded or double stranded. In some embodiments the polynucleotide is a non-coding RNA. In some embodiments the polynucleotide is a coding RNA. In some embodiments the RNA is selected from the group consisting of replicon RNA, mRNA, tRNA, siRNA, shRNA, and microRNA.

In some embodiments, the polynucleotide encodes a polypeptide. In some embodiments, the polynucleotide encodes a polypeptide that is an antigen or comprises an antigen. In some embodiments, the polypeptide encoded by the polynucleotide is a fusion protein. In some embodiments, the polypeptide encoded by the polynucleotide is LecA. In some embodiments, the polypeptide encoded by the polynucleotide is H5N1. In some embodiments, the polypeptide encoded by the polynucleotide is ID93.

In some embodiments, the polynucleotide is a replicon. In some embodiments, the replicon is a plasmid, cosmid, bacmid, phage or virus, that is capable of replication largely under its own control. In some embodiments, the replicon is RNA or DNA. In some embodiments, the replicon is single or double stranded. In some embodiments, the replicon is derived from an RNA virus.

Adjuvants

In some embodiments, the compositions provided herein further comprise an adjuvant, other than the TLR agonist. In some embodiments, the adjuvant is selected from the group consisting of a AS-2, monophosphoryl lipid A, 3-de-O-acylated monophosphoryl lipid A, IFA, QS21, CWS, TOM, AGPs, CpG-containing oligonucleotides. Toll-like receptor (TLR) agonists, Leif, saponins, saponin mimetics, biological and synthetic lipid A, imiquimod, gardiquimod, resiquimod, polyI:C, flagellin, GLA, SLA, Stingin, and combinations thereof.

Organisms

In some embodiments, the compositions provided herein comprise an organism. For example, the *Entamoeba histolytica*, an influenza-causing virus, or the bacterium *Mycobacterium tuberculosis* which causes tuberculosis (TB). Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. Thus in some embodiments the composition comprises a *Mycobacterium.*

In some embodiments the agent is a virus or a viral genome. Thus in these embodiments, the compositions comprise a virus or viral genome.

TLR Agonists

As described herein, certain embodiments of the present disclosure contemplate compositions and immunological adjuvant compositions, including pharmaceutical compositions that include one or more toll-like receptor agonist (TLR agonist). Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 *Genome Biol.* 3(8): reviews3011.1-3011.6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335; Takeda et al. 2005 *Int. Immunol.* 17:1; Kaisho et al., 2004 *Microbes Infect.* 6:1388; Datta et al., 2003 *J. Immunol.* 170:4102).

Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Phsiol.* 286:C739; Lin et al., 2005 *Shock* 24:206); poly(inosine-cytidine) (polyI:C) may be a TLR agonist through TLR3 (Salem et al., 2006 *Vaccine* 24:5119); peptidoglycans may be TLR2 and/or TLR6 agonists (Soboll et al., 2006 *Biol. Reprod.* 75:131; Nakao et al., 2005 *J. Immunol.* 174:1566); 3M003 (4-amino-2-(ethoxymethyl)-α, α-dimethyl-6,7,8,9-tetrahydro-1H-imidazo[4,5-c]quinoline-1-ethanol hydrate, Mol. Wt. 318 Da from 3M Pharmaceuticals. St. Paul, Minn., which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 *Hepatol.* 42:724). Other TLR agonists are known (e.g., Schirmbeck et al., 2003 *J. Immunol.* 171: 5198) and may be used according to certain of the presently described embodiments.

In various embodiments, the TLR agonist may be a TLR2 agonist, TLR3 agonist, TLR4 agonist. TLR5 agonist, TLR6 agonist. TLR7 agonist, TLR8 agonist, TLR7/8 agonist, TLR9 agonist, combinations thereof.

Recombinant Expression Construct

According to certain herein disclosed embodiments, the compositions described herein may contain at least one recombinant expression construct which comprises a promoter operably linked to a nucleic acid sequence encoding an antigen. In certain further embodiments the recombinant expression construct is present in a viral vector, such as an adenovirus, adeno-associated virus, herpesvirus, lentivirus, poxvirus or retrovirus vector. Compositions and methods for making and using such expression constructs and vectors are known in the art, for the expression of polypeptide antigens as provided herein, for example, according to Ausubel et al. (Eds.), Current Protocols in Molecular Biology, 2006 John Wiley & Sons, NY. Non-limiting examples of recombinant expression constructs generally can be found, for instance, in U.S. Pat. Nos. 6,844,192; 7,037,712; 7,052,904; 7,001, 770; 6,106,824; 5,693,531; 6,613,892; 6,875,610; 7,067, 310; 6,218,186; 6,783,981; 7,052,904; 6,783,981; 6,734, 172; 6,713,068; 5,795,577 and 6,770,445 and elsewhere, with teachings that can be adapted to the expression of polypeptide antigens as provided herein, for use in certain presently disclosed embodiments.

Immune Response

The present disclosure thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the present disclosure should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

Determination of the induction of an immune response by the vaccines of the present disclosure may be established by any of a number of well-known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (*Immunology Methods Manual: The Comprehensive Sourcebook of Techniques,* 1998; see also *Current Protocols in Immunology*; see also, e.g., Weir, *Handbook of Experimental Immunology,* 1986 Blackwell Scientific, Boston, Mass.; Mishell and Shigii (eds.) *Selected Methods in Cellular Immunology,* 1979 Freeman Publishing, San Francisco, Calif.; Green and Reed, 1998 *Science* 281: 1309 and references cited therein.).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present disclosure using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems. Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.). *Manual of Clinical Laboratory Immunolog,* $5^{th}$ Ed., 1997 American Society of Microbiology, Washington, D.C.

Accordingly it is contemplated that the vaccine and adjuvant compositions provided herein will be capable of eliciting or enhancing in a host at least one immune response that is selected from a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13. IL-16, IL-18 and IL-23, production one or a plurality of chemokines wherein the chemokine is selected from MIP-1α, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. Nos. 6,692,752; 7,084, 256; 6,977,073; 6,749,856; 6,733,763; 6,797,276; 6,752, 995; 6,057,427; 6,472,515; 6,309,847; 6,969,704; 6,120, 769; 5,993,800; 5,595,888; Smith et al., 1987 J Biol Chem.

262:6951; Kriegler et al., 1988 Cell 53:45 53; Beutler et al., 1986 Nature 320:584; U.S. Pat. Nos. 6,991,791; 6,654,462; 6,375,944.

Pharmaceutical Compositions

Provided herein are pharmaceutical compositions (including pharmaceutical compositions) comprising compositions described herein. In some embodiments, the composition further comprises a pharmaceutically acceptable carrier, excipient or diluent. In some embodiments, the pharmaceutical composition is a vaccine composition. The compositions described herein can be administered to a subject for stimulating an immune response in the subject (including non-specific response and antigen-specific response). In some embodiments, the subject is a mammal (e.g., an animal including farm animals (cows, pigs, goats, horses, etc.) and pets (cats, dogs, etc.), or a human). In one embodiment, the subject is a human. In another embodiment, the subject is a non-human mammal. In another embodiment, the non-human mammal is a dog, cow, or horse. In some embodiments, the subject is a warm-blooded animal.

Pharmaceutical compositions generally comprise compositions described herein and may further comprise one or more components as provided herein that are selected from antigen, additional TLR agonists, or a recombinant expression construct, in combination with a pharmaceutically acceptable carrier, excipient or diluent.

Therefore, in certain aspects, the present disclosure is drawn to TLR7/8 agonist or TLR4 agonist "monotherapy" wherein the TLR7/8 agonist or TLR 4 agonist, as described herein, is formulated in a composition that is substantially devoid of other antigens, and is administered to a subject in order to stimulate an immune response, e.g., a non-specific immune response, for the purpose of treating or preventing a disease or other condition, such as an infection by an organism. In other aspects, the present disclosure is drawing to TLR7/8 agonist or TLR4 agonist in a composition that is substantially devoid of other antigens, and is administered to a subject in order to stimulate an immune response, e.g., a non-specific immune response, for the purpose of treating or preventing a disease or other condition, such as an infection by an organism. In one embodiment, for example, the compositions and methods of the present disclosure are employed for stimulating an immune response in a subject. In another embodiment, the GLA is in the form of a spray, optionally provided in a kit.

In certain other embodiments, the pharmaceutical composition is a vaccine composition that comprises both compositions described herein and an antigen and may further comprise one or more components, as provided herein, that are selected from other TLR agonists and the like and/or a recombinant expression construct, in combination with a pharmaceutically acceptable carrier, excipient or diluent. Illustrative carriers will be nontoxic to recipients at the dosages and concentrations employed.

Illustrative carriers will be nontoxic to recipients at the dosages and concentrations employed. For vaccines comprising TLR7/8 agonist or TLR4 agonist plus an antigen, about 0.01 µg/kg to about 100 mg/kg body weight will be administered, typically by the intradermal, subcutaneous, intramuscular or intravenous route, or by other routes.

A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit, 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id, at 1449. In addition, antioxidants and suspending agents may be used. Id.

"Pharmaceutically acceptable salt" refers to salts of the compounds of the present embodiments derived from the combination of such compounds and an organic or inorganic acid (acid addition salts) or an organic or inorganic base (base addition salts). The compositions of the present embodiments may be used in either the free base or salt forms, with both forms being considered as being within the scope of the present embodiments.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033, 598; 7,018,345; 6,970,739), sonophoretic (e.g., U.S. Pat. Nos. 4,780,212; 4,767,402; 4,948,587; 5,618,275; 5,656, 016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the present disclosure in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline. Ringer's solution, isotonic sodium chloride, fixed oils such as squalene, squalane, mineral oil, a mannide monooleate, cholesterol, and/or synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In another embodiment, a composition of the present disclosure is formulated in a manner which can be aerosolized.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of the present disclosure, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of the present embodiments. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

As described above, in certain embodiments the present disclosure includes compositions capable of delivering nucleic acid molecules encoding desired antigens. Such compositions include recombinant viral vectors (e.g., retroviruses (see WO 90/07936. WO 91/02805. WO 93/25234, WO 93/25698, and WO 94/03622), adenovirus (see Berkner, Biotechniques 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. Nos. 4,769,330; 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264: 16985-16987, 1989) and lipid-DNA combinations (see Feigner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

Accordingly, the present embodiments are useful for enhancing or eliciting, in a host, a patient or in cell culture, an immune response. As used herein, the term "patient" refers to any warm-blooded animal, preferably a human. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes. B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

In certain embodiments a liquid composition intended for either parenteral or oral administration should contain an amount of vaccine composition such that a suitable dosage will be obtained. Typically, this amount is at least 0.01 wt % of an antigen in the composition. When intended for oral administration, this amount may be varied to be between 0.1 and about 70% of the weight of the composition. Preferred oral compositions contain between about 4% and about 50% of the antigen. Preferred compositions and preparations are prepared so that a parenteral dosage unit contains between 0.01 to 1% by weight of active composition.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, Ala.; e.g., product number 699800) of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the present disclosure, the vaccine compositions/adjuvants may be administered through use of insert(s), bead(s), timed-release formulation(s), patch(es) or fast-release formulation(s).

Also contemplated in certain embodiments are kits comprising the herein described vaccine compositions and/or immunological adjuvant compositions, which may be provided in one or more containers. In one embodiment all components of the vaccine compositions and/or immunological adjuvant compositions are present together in a single container, but the embodiments are not intended to be so limited and also contemplate two or more containers in which, for example, an immunological adjuvant composition is separate from, and not in contact with, the antigen component. By way of non-limiting theory, it is believed that in some cases administration only of the immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a vaccine composition as described herein and containing both antigen and adjuvant composition, and optionally other herein described components as well.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

The following Examples are offered by way of illustration and not by way of limitation.

EXAMPLES

Example 1. Adsorption of a Synthetic TLR7/8 Ligand to Aluminum Oxyhydroxide for Enhanced Adjuvant Activity

Abstract

For nearly a century, aluminum salts have been the most widely used vaccine adjuvant formulation, and have thus established a history of safety and efficacy. Nevertheless, for extremely challenging disease targets such as tuberculosis or HIV, the adjuvant activity of aluminum salts may not be potent enough to achieve protective efficacy. Adsorption of TLR ligands to aluminum salts facilitates enhanced adjuvant activity, such as in the human papilloma virus vaccine Cervarix®. However some TLR ligands such as TLR7/8 agonist imidazoquinolines do not efficiently adsorb to aluminum salts. The present disclosure describes a formulation approach to solving a challenge by developing a lipid-based nanosuspension of a synthetic TLR7/8 ligand (e.g., 3M-052) that facilitates adsorption to aluminum salts via the structural properties of the helper lipid employed. In immunized mice, the aluminum oxyhydroxide-adsorbed formulation of 3M-052 enhanced antibody and TH1-type cellular immune responses to vaccine antigens for tuberculosis and HIV.

The present disclosure provides that structural properties of helper lipids may promote the adsorption of PRR ligands to aluminum salts, without altering PRR ligand chemical structure, when the PRR ligand is first formulated with the helper lipid in the form of an aqueous nanosuspension. Moreover, the versatility of the approach may allow adsorption of the same PRR ligand to different types of aluminum salts depending on the structure of the helper lipid with which it is complexed. The present disclosure provides a formulation approach involving the development of nanosuspensions to modulate the adsorption interactions between the synthetic TLR7/8 ligand 3M-052 (5) and aluminum salts in order to create a vaccine adjuvant formulation that enhances antibody and cellular immunogenicity to co-adsorbed recombinant tuberculosis or HIV vaccine antigens.

Materials and Methods

Adjuvant formulation materials. Synthetic 1,2-dilauroyl-sn-glycero-3-phosphcocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1,2-dilauroyl-sn-glycero-3-phospho-(1'-rac-glycerol) (DLPG), 1,2-dimyrsitoyl-sn-glycero-3-phospho-(1'-rac-glycerol) (DMPG), 1,2-dipalmitoyl-sn-glycero-3-phospho-(1'-rac-glycerol) (DPPG), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-3-trimethylammonium-propane (DSTAP), 1,2-dipalmitoyl-3-trimethylammonium-propane (DPTAP), and glucopyranosyl lipid adjuvant (GLA, also known as PHAD®) were purchased from Avanti Polar Lipids Inc (Alabaster, Ala.). Polysorbate 80 was purchased from J.T. Baker (San Francisco, Calif.). Poloxamer 188 was purchased from Spectrum Chemical (Gardena, Calif.). Saline solution (0.9% w/v) was purchased from Teknova (Hollister, Calif.). TLR9 CpG control was obtained from Avecia (Milfrod, Mass.). Alhydrogel® '85' and AdjuPhos® were purchased from E.M. Sergeant Pulp & Chemical Co. (Clifton, N.J.). HIV gp120 antigen is referred to in Fouts et al. ("Expression and Characterization of a Single-Chain Polypeptide Analogue of the Human Immunodeficiency Virus Type 1 gp120-CD4 Receptor Complex" Virol. vol. 74, no. 24, December 2000, 11427-11436.)

GLA used in the examples has the structure of Formula (III) wherein $R^1$, $R^3$, $R^5$ and $R^6$ are $C_{11}$ alkyl; and $R^2$ and $R^4$ are $C_{13}$ alkyl.

Adjuvant Formulation Manufacture

Aqueous nanosuspensions were manufactured by dispersing 3M-052 or GLA with lipid excipient at a 1:2 molar ratio (adjuvant:lipid), in chloroform or a mixture of chloroform, methanol, and water. The solvent was then evaporated using a Genevac EZ-2 centrifugal evaporator (Stone Ridge, N.Y.). The dried films were rehydrated in ultrapure water, then sonicated in a Crest powersonic CP230D (Trenton, N.J.) sonicating water bath at ~60° C. for up to several hours or until the formulations were translucent with no visible particles. To formulate alum-containing compositions, the aqueous nanosuspensions were mixed with Alhydrogel® or AdjuPhos®. For the immunogenicity studies, recombinant vaccine antigens (ID93 or HIV gp120 antigen) were mixed together with the nanosuspension, alum, and the indicated diluent.

Adjuvant Formulation Characterization and Stability

Aqueous nanosuspensions were characterized for particle size by dynamic light scattering (DLS) using the Malvern Instruments (Worcestershire, UK) Zetasizer Nano-S or -ZS. Aqueous nanosuspensions were diluted 1:10 or 1:100 fold in water in a polystyrene cuvette prior to analysis, which consisted of three measurements resulting in a scattering intensity-biased average diameter value reported as the Z-ave. Zeta potential was measured using the Zetasizer Nano-ZS using a disposable capillary cell, with nine consecutive measurements collected from each sample prepared at 1:10 dilution in water. In general, 3M-052 concentration was measured by UV absorbance at 322.5 nm after diluting formulations 1:20 into ethanol:HCl (98:2 v:v) and comparing to a standard curve. The dilution into organic solvent removes potential interference from light scattering of the nanosuspension particles. However, for the 3M-052 binding isotherm, where maximum sensitivity was desired, no dilution was performed for the samples or the standards. Alternatively, 3M-052 concentration was determined by reverse phase HPLC with charged aerosol detection. TLR9 CpG control concentration was measured by UV absorbance at 260 nm after 1:20 dilution into ethanol:HCl. GLA concentration was measured by reverse-phase HPLC with an C18 column (Atlantis T3 or Agilent XBridge) and charged aerosol detection (CAD) using a methanol:chloroform:water mobile gradient as described previously (6). To detect unbound TLR ligand, alum-containing formulations were centrifuged briefly as indicated and the supernatant assayed by UV absorbance or HPLC-CAD. Depending on experiment, centrifugation time was 2-5 min at 2,000-16.000×g. In some experiments (FIG. 2D and Table 4), to remove the influence of saline or buffer salts on the sedimentation of TLR agonists in aluminum salt preparations, aluminum salts were first centrifuged and the supernatants removed and replaced with water; this process was repeated for another wash prior to employing the aluminum salts in the binding studies.

CryoTEM Imaging

Samples were preserved in vitrified ice supported by holey carbon films on 400-mesh copper grids. Samples were prepared by applying a 3 µL drop of sample suspension to a cleaned grid, blotting away with filter paper, and immediately proceeding with vitrification in liquid ethane. Grids were stored under liquid nitrogen until transferred to the electron microscope for imaging. Electron microscopy was performed using an FEI Tecnai T12 electron microscope, operating at 120 keV equipped with an FEI Eagle 4k×4k CCD camera. Vitreous ice grids were transferred into the electron microscope using a cryostage that maintains the grids at a temperature below –170° C. Images of each grid were acquired at multiple scales to assess the overall distribution of the specimen. After identifying potentially suitable target areas for imaging at lower magnifications, high magnification images were acquired at nominal magnifications of 110,000× (0.10 nm/pixel), 52,000× (0.21 nm/pixel) and 21,000× (0.50 nm/pixel). The images were acquired at a nominal underfocus of –2 µm (110.000×), –3 µm to –2 µm (52,000×) and –5 µm (21,000×) and electron doses of ~9-42 e/Å$^2$.

Antigen Adsorption to Aluminum Salts

Binding efficiency of 3M-052 and ID93 or HIV gp120 antigen to Alhydrogel® and AdjuPhos® was determined by UV-Vis Spectroscopy and SDS-PAGE with silver stain. 1-mL of formulation was prepared by mixing saline diluent, antigen, 3M-052-AF, and/or aluminum salt. To determine HIV gp120 antigen adsorption, 30 µl of sample supernatant was mixed with 10 µl of 4× reducing or non-reducing LDS Sample Buffer, following which 20-25 µl was loaded into a 10-lane SDS-PAGE gel with 15 µl of SeeBlue2 Prestained Standard. To determine ID93 adsorption, 45 µl of sample supernatant was mixed with 15 µl of 4× reducing LDS Sample Buffer, following which 25 µl was loaded into a 10-lane SDS-PAGE gel with 15 µl of SeeBlue2 Prestained Standard. The gels were run for 55 minutes at 190 V and then placed into a fixing solution of 50:40:10 EtOH: $CH_3COOH:H_2O$ for overnight. The gels were then stained according to the directions provided by Sigma-Aldrich (Saint Louis, Mo.) ProteoSilver Plus Silver Stain Kit.

Animals and Immunizations

C57Bl/6 and B6.129S1-TLR7$^{tm1Flv}$/J (TLR7$^{-/-}$) were purchased from Jackson Laboratories (Bar Harbor, Me.). Mice were immunized by intramuscular injection with the recombinant TB vaccine antigen ID93 (0.5 µg/dose) or the HIV gp120 antigen (10 µg/dose) adjuvanted with AdjuPhos, Alhydrogel®, 3M-052+Alhydrogel®, 3M-052+AdjuPhos, or GLA+Alhydrogel®. The final adjuvant dose was 5 µg GLA or 0.1-10 µg 3M-052 with 200 µg of AdjuPhos or Alhydrogel® in 100 µL. Mice were boosted three weeks after the first immunization. All mice were maintained in specific pathogen-free conditions. All procedures were approved by the IDRI Institutional Animal Care and Use Committee.

Antibody Titers

Mouse sera (N=5/group) were prepared 21 days after immunization by collection of retro-orbital blood into microtainer serum collection tubes (VWR International. West Chester, Pa.), followed by centrifugation. Each serum sample was then analyzed by antibody capture ELISA. Briefly, ELISA plates (Nunc, Rochester, N.Y.) were coated with 2 µg/ml of the immunizing antigen in 0.1 M bicarbonate buffer and blocked with 1% BSA-PBS. Then, in consecutive order and following washes in PBS/Tween20, serially diluted serum samples, anti-mouse IgG, IgG1 or IgG2c-HRP (Southern Biotech, Birmingham, Ala.) and ABTS-H2O2 (Kirkegaard and Perry Laboratories, Gaithersburg, Md.) were added to the plates. Plates were analyzed at 405 nm (ELX808. Bio-Tek Instruments Inc, Winooski, Vt.). Endpoint titers were calculated using Prism software V6 (GraphPad). Alternatively vaginal lavage fluid was collected three weeks after the third immunization with HIV gp120 antigen and analyzed for antibody titers using the same methods.

Intracellular Cytokine Staining

One week after the final immunization splenocytes and were isolated. Red blood cells were lysed using Red Blood Cell Lysis Buffer (eBioscience) and resuspended in RPMI 1640 and 10% FBS. Cells were plated at $2\times10^6$ cells/well in 96-well plates and were stimulated for 2 hours with the immunizing antigen (10 µg/mL), or unstimulated at 37° C. GolgiPlug (BD Biosciences) was added and the cells were incubated for an additional 8 hours at 37° C. Cells were washed and surface stained with fluorochrome-labeled antibodies to CD4 (clone GK1.5). CD44 (clone IM7) and CD8 (clone 53-6.7) (BioLegend and eBioscience) in the presence of anti-CD16/32 (clone 2.4G2) for 20 minutes. Cells were washed and permeabilized with Cytofix/Cytoperm (BD Biosciences) for 20 minutes. Cells were washed twice with Perm/Wash (BD Biosciences) and stained intracellularly with fluorochrome-labeled antibodies to CD154 (clone MR1), IFN-γ (clone XMG-1.2). IL-2 (clone JES6-5H4), TNF (clone MP6-XT22), GM-CSF (clone MP1-22E9), IL-5 (clone TRFK5), and IL-17A (clone TC11-18H10.1) (BioLegend and eBioscience) for 20 minutes at room temperature. Cells were washed and resuspended in PBS. Up to $10^6$ events were collected on an LSRFortessa flow cytometer (BD Biosciences). Data were analyzed with FlowJo (TreeStar). Cells were gated as singlets>lymphocytes>CD4+ CD8−>cytokine positive or CD44$^{hi}$>cytokine positive. Antigen-specific response frequencies were determined by subtracting the frequency of response positives of unstimulated cells from antigen stimulated cells.

Antibody Secreting Cell ELISPOT Assay

Antigen-specific antibody secreting cells present in the bone marrow were quantified using an ELISPOT assay. One day prior to assay initiation. Multiscreen ELISPOT plates (Millipore) were coated with 1 ug of antigen/well, and incubated overnight. Blocked plates were washed three time with washing buffer (PBS+0.5% Tween 20), blocked with collection medium for two hours, and washed 3 times. Bone marrow was collected 21 days post-immunization in RPMI medium supplemented with 10% fetal bovine serum (FBS), quantified using a Guava automated cell counter (Millipore) and resuspended to $1\times10^6$ cells/mL. Cells were serially diluted 3-fold, added to plates, and incubated for 5 hours at 37° C. Secreted antibody was detected by addition of a 1:100 dilution of horse radish peroxidase (HRP) conjugated goat anti-mouse IgG antibody (Southern Biotech). Spots were visualized with AEC Peroxidase substrate kit (Vector Labs) according to manufacturer's instructions. Spots were quantitated on a CTL bioanalyzer.

Innate Immune Response

Eighteen hours after intramuscular immunization into the gastrocnemius muscle the draining popliteal lymph node was collected and dissociated in PBS containing protease inhibitors (Thermo Fisher Scientific). Cells were surface stained for CD8, CD90.2 (clone 53-2.1), CD19 (clone ID3), NK1.1 (clone PK136), CD11c (clone N418), CD11b (clone M1/70), Ly6G (clone 1A8), Ly6C (HK1.4), CD69 (clone H1.2F3), and CD86 (clone GL1) for 20 minutes on ice. Cells were washed and permeabilized with Cytofix/Cytoperm (BD Biosciences) for 20 minutes. Cells were washed twice with Perm/Wash (BD Biosciences) and stained intracellularly with fluorochrome-labeled antibodies to IFN-γ and proIL-1β (clone NJTEN3) (BioLegend and eBioscience) for 20 minutes at room temperature. Cells were washed and resuspended in PBS. Up to $10^6$ events were collected on an LSRFortessa flow cytometer (BD Biosciences). Data were analyzed with FlowJo (TreeStar). Cells were gated as singlets>cells>CD19+CD90.2− (B cells), CD8+CD90.2+ (CD8 T cells), CD8− CD90.2+(CD4 T cells), CD8− CD19− NK1.1+(NK cells). CD8− CD19− CD11c+(DCs), CD8− CD19−CD11b+Ly6C+(inflammatory monocytes), or CD19−CD11b+Ly6G+(PMNs)

Statistical Analysis

Antibody and T-cell responses were analyzed by two-way ANOVA with Tukey's multiple comparison correction using Prism version 5 or later (GraphPad). Comparisons resulting in p-values<0.05 were considered significant. Only meaningful comparisons are reported in the figures (adjuvanted groups vs. antigen alone; 3M-052-Alhydrogel® vs. Alhydrogel®, 3M-052-AF, or 3M-052-AdjuPhos®; 3M-052-AdjuPhos vs. AdjuPhos® or 3M-052-AF).

Results

Formulation Development and Physicochemical Characterization

Figure 2A:
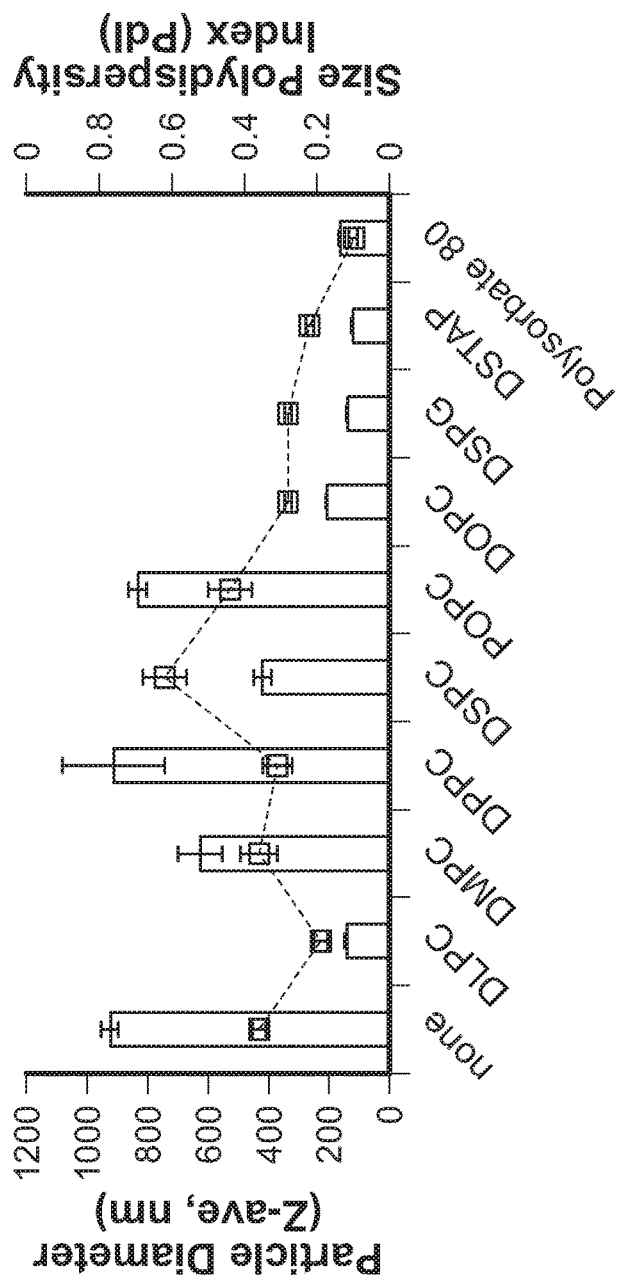
FIG. 2A-2D show physical properties of aqueous suspensions of 3M-052 and adsorption to aluminum salts.
Figure 2B:
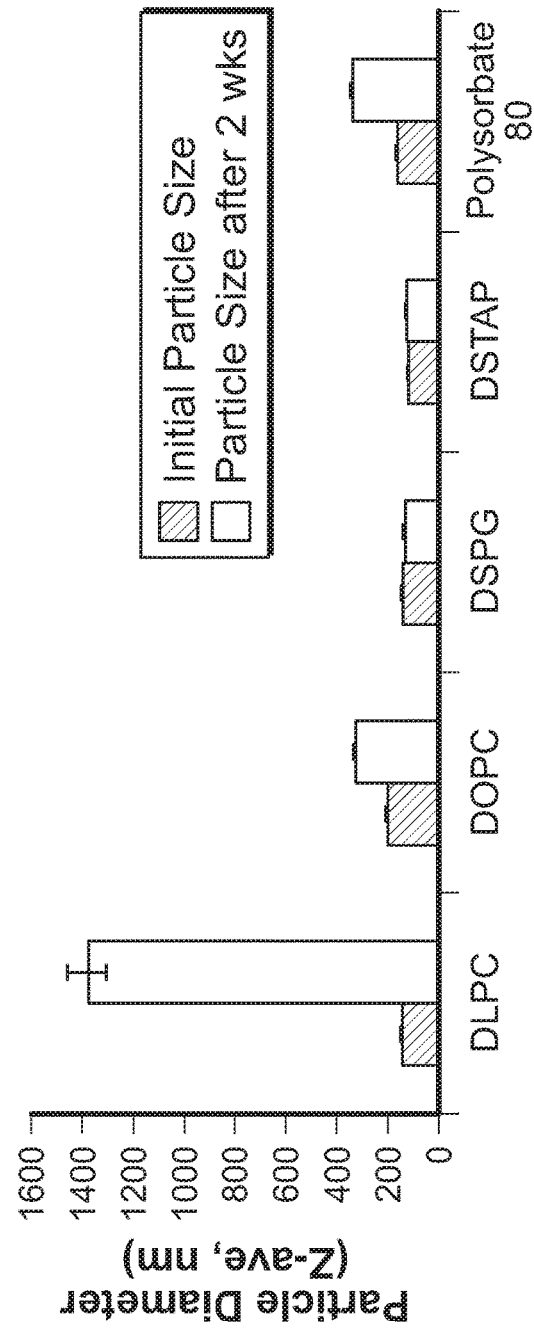

Aqueous nanosuspensions of TLR ligands are formed by adding a suitable helper lipid and inputting energy (e.g. sonication) to break down the particle size of the lipid complex (7). To determine a suitable helper lipid to form nanosize particles with 3M-052, a range of phospholipids (FIG. 1) was screened. These helper lipids were first mixed with 3M-052 in organic solvent at a molar ratio of 1:2 (3M-052:helper lipid), based on work with a TLR4 ligand (8). Following evaporation of the solvent, the formulations were hydrated and sonicated to reduce particle size to about <200 nm to enable the potential for terminal sterile filtration. Several formulations demonstrated acceptable particle size (about <200 nm) after manufacture as determined by dynamic light scattering (FIG. 2A). The nature of the helper lipid dictated formulation particle size and physical stability. Some formulations had grown significantly in size (DLPC, DOPC, polysorbate 80) indicating formulation physical instability while others demonstrated little change (DSPG. DSTAP) upon storage at 5° C. for 2 weeks (FIG. 2B).

Figure 2C:
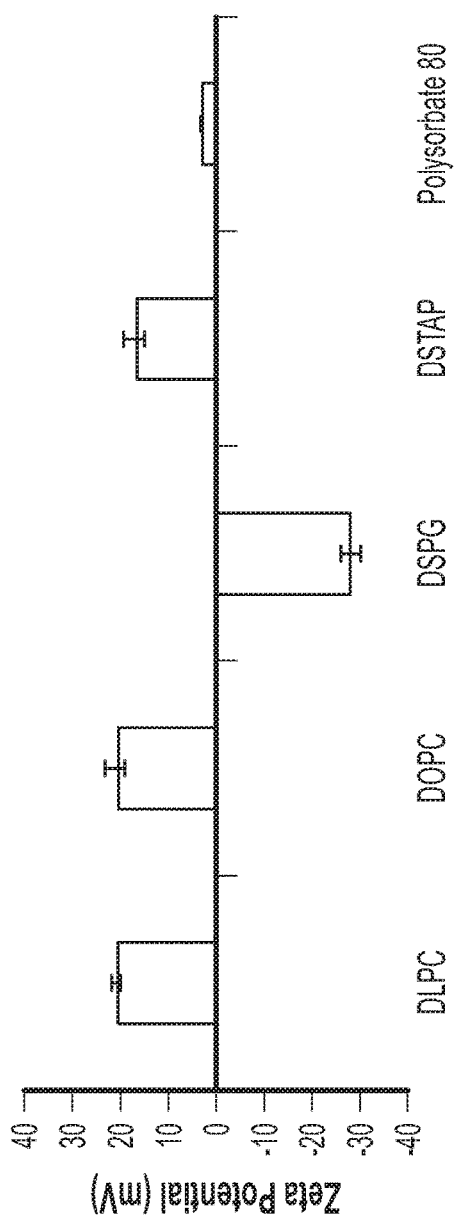
Figure 2D:
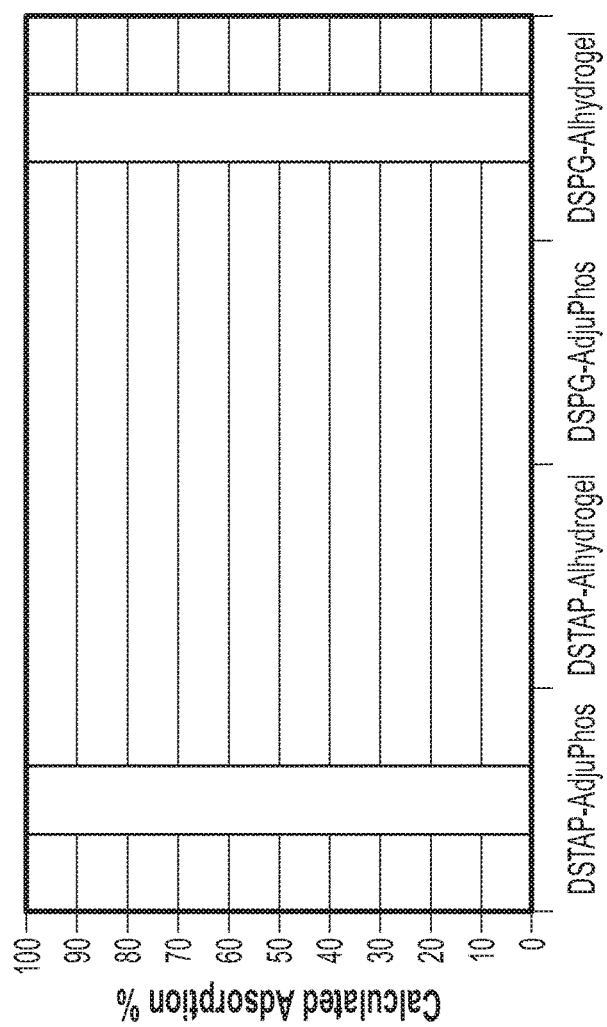

Most of the formulations were positively charged (FIG. 2C), as expected due to the chemical structure of imidazoquinolines such as 3M-052, which have a pKa ~7 (9). However, DSPG caused formation of anionic particles due to the negative charge of the phosphate group in DSPG. An anionic aqueous suspension is of particular interest for vaccine adjuvant development due to the potential for adsorption to aluminum oxyhydroxide. Accordingly, the adsorption of the stable aqueous suspensions of 3M-052 to aluminum oxyhydroxide or aluminum phosphate was tested. At a concentration of 100 µg/ml 3M-052, efficient binding of the DSPG-based suspension to aluminum oxyhydroxide was observed but no detectable adsorption of the DSTAP-based suspension of 3M-052 to aluminum oxyhydroxide occurred (FIG. 2D, estimated LOD~5 µg/mL). In contrast, the DSTAP-based suspension efficiently adsorbed to aluminum phosphate but not to aluminum oxyhyroxide. Thus, by appropriate selection of helper lipid, the adsorption of 3M-052 aqueous nanosuspensions to different types of aluminum salts is facilitated. Phospholipids with the same or similar headgroup as DSPG but different acyl chain length or saturation also promoted nanosuspension formation and adsorption of 3M-052 to aluminum oxyhydroxide (Table 1).

TABLE 1

Effect of acyl chain and saturation on PG-based nanosuspension size and adsorption properties. Values represent average +/− s.d. of three measurements from the same sample for particle size and size polydispersity, or duplicate samples for the adsorption to Alhydrogel ® experiment.

| Helper Lipid | Acyl Chain Length:Number of Unsaturated Bonds | Size (Z-Ave, nm) | PdI | Calculated Adsorption to Alhydrogel ® |
|---|---|---|---|---|
| DLPG | 12:0 | 114 ± 9 | 0.79 ± 0.09 | 85 ± 2% |
| DMPG | 14:0 | 117 ± 47 | 0.25 ± 0.07 | 79 ± 0% |
| DPPG | 16:0 | 167 ± 13 | 0.38 ± 0.09 | 86 ± 1% |
| DSPG | 18:0 | 182 ± 1 | 0.44 ± 0.01 | 87 ± 1% |
| DOPG | 18:1 | 181 ± 9 | 0.52 ± 0.07 | 87 ± 0% |

Figure 10:
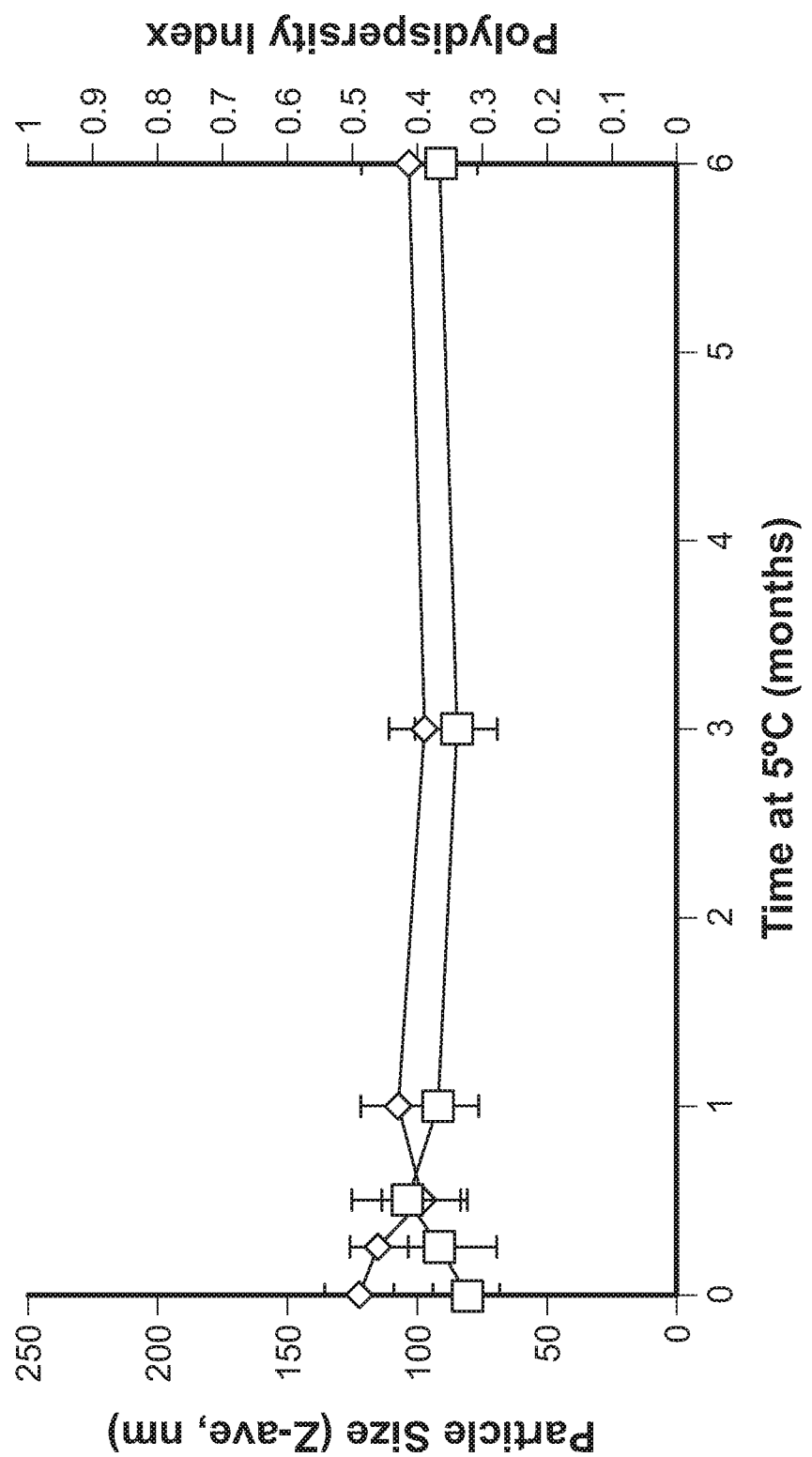
FIG. 10 shows 3M-052-DSPG nanosuspension particle size and size polydispersity over 6 months (n=6 batches, average+/−s.d. is shown).

Subsequent efforts on the DSPG-based nanosuspension (hereafter denoted 3M-052-AF) was focused due to its ability to form a nanosuspension that adsorbs to aluminum oxyhydroxide, which is the generally preferred aluminum salt for anionic recombinant protein antigens such as those employed in the present disclosure. 3M-052-AF was physically stable for at least 6 months at 4° C., showing little change in average particle size or particle size polydispersity (FIG. 10).

Figure 3A:
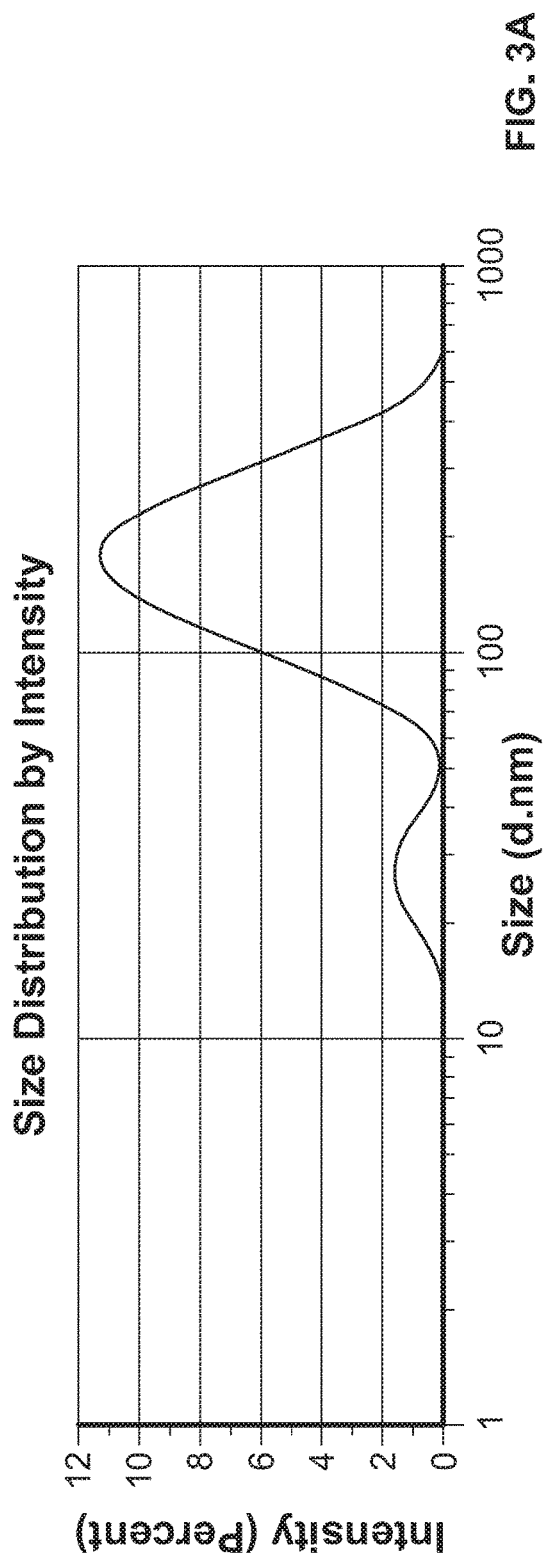
FIG. 3A-3B show particle size characteristics of 3M-052-AF alone or in the presence of aluminum oxyhydroxide.
Figure 3B:
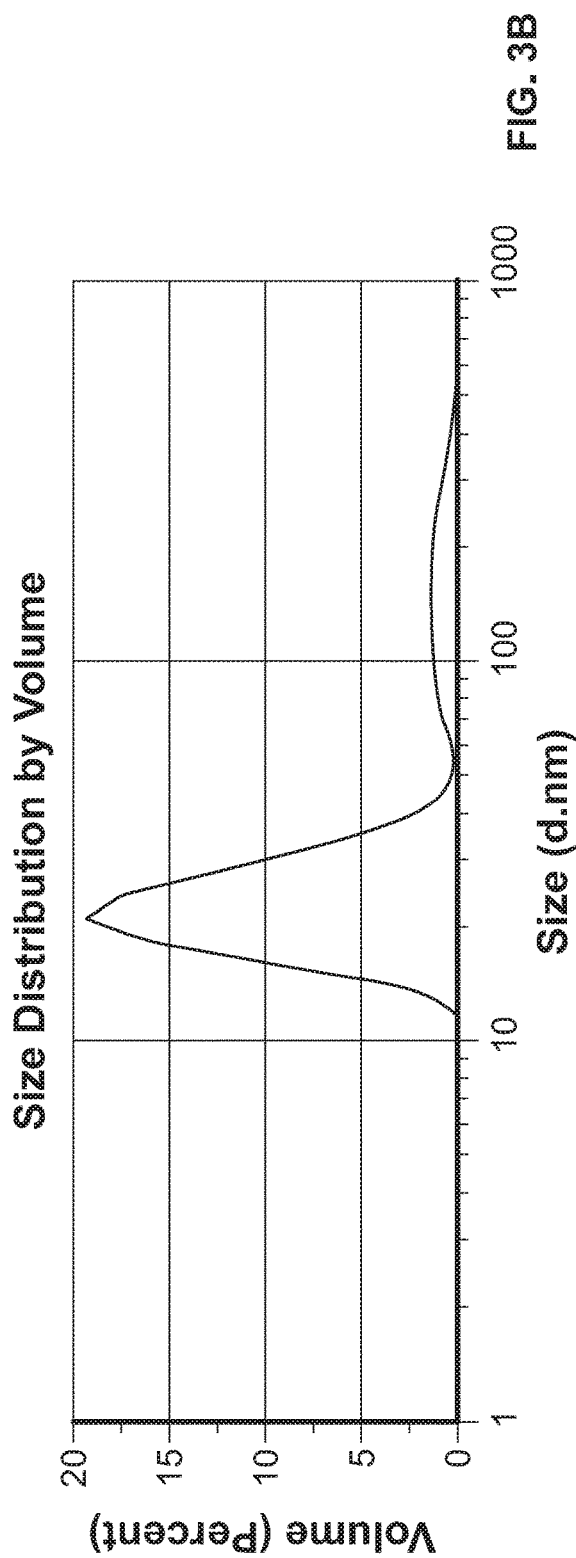

The morphology of 3M-052-AF as characterized by cryo-transmission electron microscopy (cryoTEM) indicates a fairly uniform suspension of micellar structures ~5-15 nm in diameter, although larger irregularly shaped particles were also present (data not shown). These size characteristics may appear to contradict the dynamic light scattering indicated above, where Z-ave values were generally over 100 nm. However, the light scattering intensity-based Z-ave value reported by dynamic light scattering is influenced by small proportion of large particles since they scatter more light than smaller particles (light scattering is proportional to $10^6$ of the particle diameter) as evident in FIG. 3A. Mathematical conversion of the intensity based size distribution to a volume-based size distribution indicates more particles in the ~20 nm range, although even volume-based size distributions are also skewed by larger particles, with a proportionality of $10^3$. Nevertheless, the volume-based size distribution of 3M-052-AF is more consistent with the cryoTEM results (FIG. 3b). Due to the small particle size of the 3M-052-AF, the nanosuspension particles were not evident in the cryo-TEM images containing aluminum oxyhydroxide (data not shown). Indeed, the morphology of the aluminum oxyhydroxide particles appeared much the same regardless of whether 3M-052-AF was present, with the notable exception that the crystalline aggregates appeared larger in size in the sample containing 3M-052-AF compared to the aluminum oxyhydroxide control.

Figure 4:
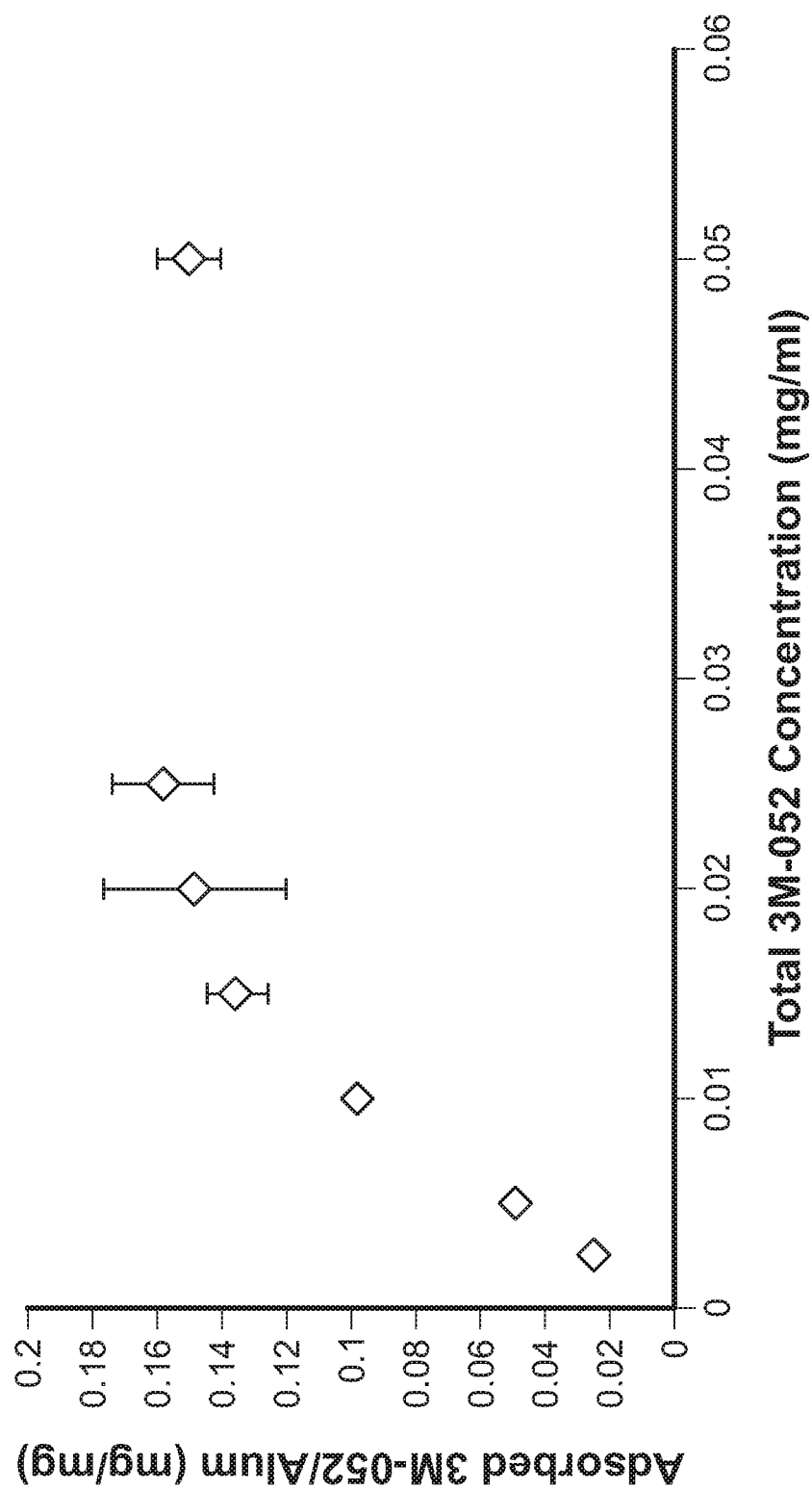
FIG. 4 shows adsorption isotherm of 3M-052-AF to Alhydrogel® as measured by UV absorbance of supernatant. Error bars represent standard deviation from two separate experiments using separate batches of 3M-052, where each sample from each experiment was performed in duplicate.

To determine the adsorption capacity of Alhydrogel® for 3M-052-AF, the nanosuspension at various concentrations was mixed with aluminum oxyhydroxide and allowed to sit for ~30 min with intermittent vortexing, followed by centrifugation such that the aluminum particles pelleted. The supernatant was then assayed for 3M-052 to detect unbound material (FIG. 4). The adsorption capacity of the nanosuspension was ~0.16 mg per mg of aluminum. The doses of 3M-052 employed in the subsequent mouse immunogenicity experiments described in the present disclosure were below this level. The adsorption stability of 3M-052-AF on Alhydrogel® over time was evaluated by assaying samples for unbound 3M-052 before and after storage at 5° C. for 16 wks. Although there appeared to be partial loss of 3M-052 in the supernatants of the controls (possibly indicative of sticking to the plastic microcentrifuge tube), there was no increase in detectable 3M-052 in the supernatants of Alum-containing samples, indicating no desorption over 16 wks (Table 2). Moreover, the presence of other TLR ligands did not appear to interfere with the adsorption of 3M-052 to aluminum oxyhydroxide, indicating that an Alum-based formulation containing multiple adsorbed PRR ligands could be feasible (Table 2).

TABLE 2

Stability of adsorption of 3M-052-AF over time and in the presence of co-adsorbed TLR ligands. 3M-052-AF contains DSPG whereas GLA-AF contains DPPG. TLR9 CpG control is soluble and thus contains no helper lipid. Unbound TLR ligands were assayed by UV absorbance (3M-052, TLR9 CpG control) or HPLC with charged aerosol detection (GLA). Values represent average +/− s.d. of duplicate samples.

| TLR Ligand(s) | Aluminum Salt | TLR Agonist Conc. In Supernatant (µg/ml, T = 0) | TLR Agonist Conc. In Supernatant (µg/ml, T = 16 wks) |
|---|---|---|---|
| 3M-052 | — | 94 ± 1 | 74 ± 1 |
| GLA | — | 93 ± 1 | 84 ± 4 |
| TLR9 CpG control | — | 90 ± 3 | 81 ± 0 |
| 3M-052/GLA | — | 88 ± 1/94 ± 6 | 80 ± 2/89 ± 8 |
| 3M-052/TLR9 CpG control | — | 93 ± 1/NM | 81 ± 1/NM |
| 3M-052 | Alhydrogel ® | 11 ± 1 | 10 ± 1 |
| GLA | Alhydrogel ® | <10 | <10 |
| TLR9 CpG control | Alhydrogel ® | <10 | <10 |
| 3M-052/GLA | Alhydrogel ® | 11 ± 3/<10 | <10/<10 |
| 3M-052/TLR9 CpG control | Alhydrogel ® | 11 ± 1/<10 | <10/<10 |

NM: not measured

To determine whether 3M-052 adsorbed to aluminum oxyhydroxide via a ligand exchange or electrostatic mechanism, the effect of ionic strength on adsorption, which neutralizes electrostatic mediated binding (10), was evaluated. A trend of decreasing 3M-052 content in the supernatant of the control samples with increasing sodium chloride concentration is attributable to a rapid increase in particle of 3M-052-AF upon exposure to saline, resulting in pelleting of the nanosuspension even when the aluminum was not present (Table 3). Nevertheless, increasing sodium chloride concentration did not appear to reduce the binding of 3M-052-AF to aluminum oxyhydroxide.

TABLE 3

Effect of concentration of saline on adsorption of 3M-052-AF to Alhydrogel ®. Samples were centrifuged for 10 s at 2000 x g. Values represent average +/− s.d. of duplicate samples.

| Saline Conc. (mM) | Aluminum Salt | 3M-052 Conc. in Supernatant (µg/ml) | Adsorption to Alhydrogel ® |
|---|---|---|---|
| 60 | — | 79 ± 1 | — |
| 60 | Alhydrogel ® | <10 | ≥87% |
| 120 | — | 61 ± 3 | — |
| 120 | Alhydrogel ® | <10 | ≥84% |
| 240 | — | 57 ± 9 | — |

TABLE 3-continued

Effect of concentration of saline on adsorption of 3M-052-AF to Alhydrogel ®. Samples were centrifuged for 10 s at 2000 x g. Values represent average +/- s.d. of duplicate samples.

| Saline Conc. (mM) | Aluminum Salt | 3M-052 Conc. in Supernatant (μg/ml) | Adsorption to Alhydrogel ® |
|---|---|---|---|
| 240 | Alhydrogel ® | <10 | ≥82% |
| 480 | — | 51 ± 10 | — |
| 480 | Alhydrogel ® | <10 | ≥80% |

Adjuvant Biological Activity

Figure 5A:
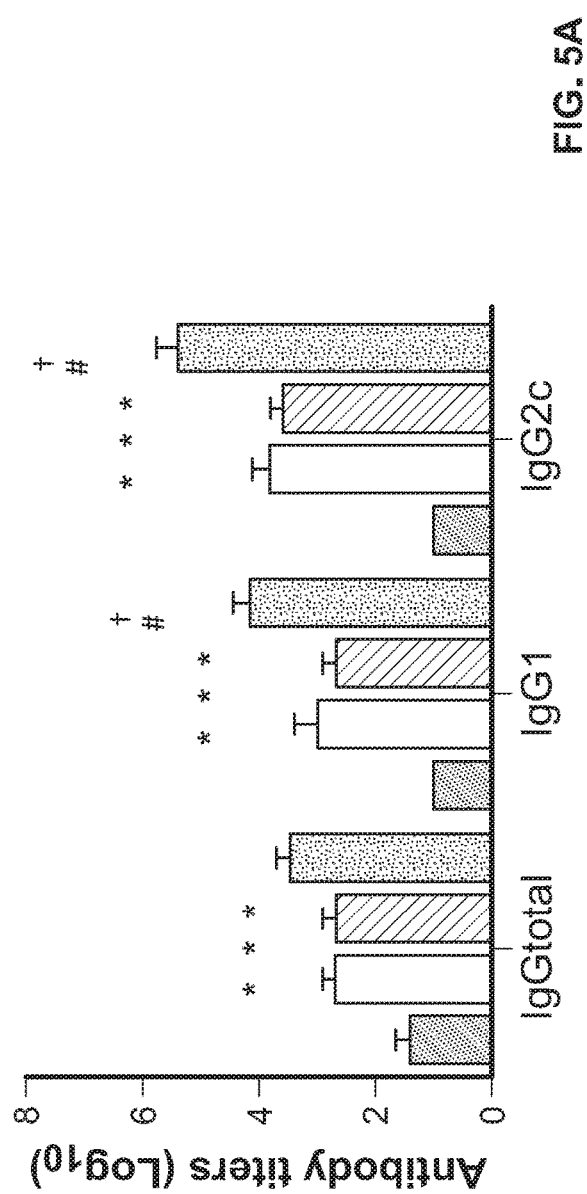
FIG. 5A-5B show that alum and 3M052 induce synergistic antigen-specific immunogenicity. C57BL/6 mice were immunized three times, three weeks apart via intramuscular injection with ID93 (0.5 µg) alone or adjuvanted with 3M-052-AF (0.5 µg), Alhydrogel®, or 3M-052-AF (0.5 µg) bound to Alhydrogel®.
Figure 5B:
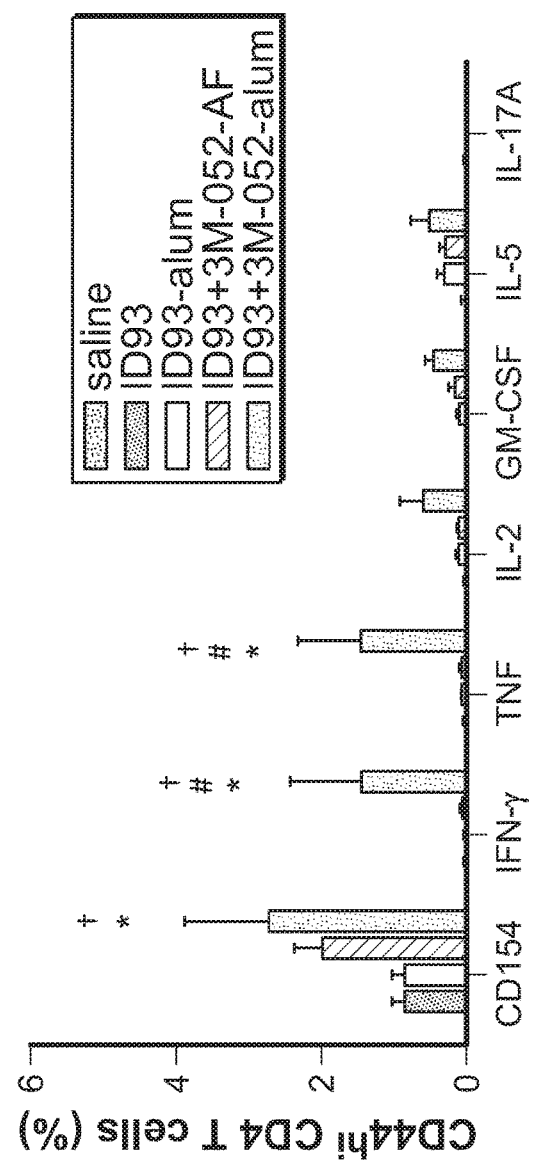

To determine whether the binding of 3M-052 to aluminum oxyhydroxide alters the in vivo adjuvanticity of aluminum oxydroxide or 3M-052-AF we immunized C57BL/6 mice with the tuberculosis vaccine antigen ID93 (11) adjuvanted with either 3M-052-AF, aluminum oxyhydroxide, or 3M-052-AF bound to aluminum oxyhydroxide. Three weeks after the first immunization, mice receiving ID93+3M-052-Alhydrogel® exhibited the highest serum titers of ID93-specific total IgG as well as IgG1 and IgG2c subtypes indicating that 3M-052-Alhyrogel has unique adjuvant properties compared to either 3M-052-AF or Alhydrogel® alone (FIG. 5A). One month after the third immunization, CD4 T cell responses were assessed by stimulating splenocytes with ID93 and measuring cytokine production in the presence of Brefeldin A by flow cytometry. Compared to mice immunized with ID93 alone, both ID93+3M-052-AF and ID93+3M-052-Alhydrogel® immunized mice had greater frequencies of ID93-specific CD4 T cells expressing CD154. The mice immunized with ID93+3M-052-Alhydrogel® exhibited TH1 cells that made IFN-γ, TNF. IL-2 and GM-CSF upon ID93 stimulation (FIG. 5B). While several follow-up experiments confirmed these findings, some batches of 3M-052-AF appeared to induce TH11 T cell adjuvant activity comparable to 3M-052-Alhydrogel®. One potential explanation for this discrepancy concerns the ratio of phospholipid (DSPG) to 3M-052. In work using a TLR4 ligand, it was shown that systematically varying the phospholipid: TLR4 ligand ratio revealed a bi-phasic response in physicochemical as well as in vitro bioactivity assays (12). Thus, if the phospholipid:3M-052 ratio employed in the present disclosure is near such an inflection point, seemingly minor variations in the preparation or physical properties of the formulation could result in changes in its biological activity.

Figure 6D:
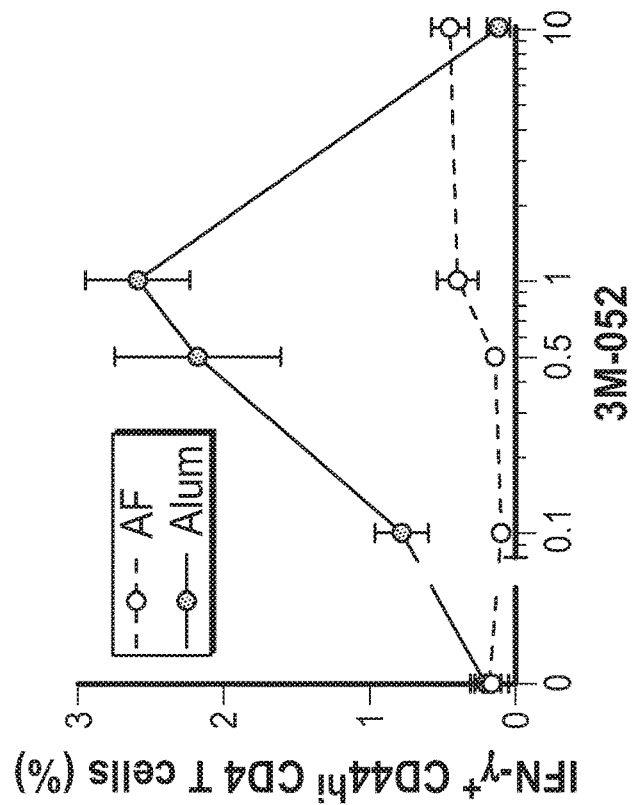
Figure 6C:
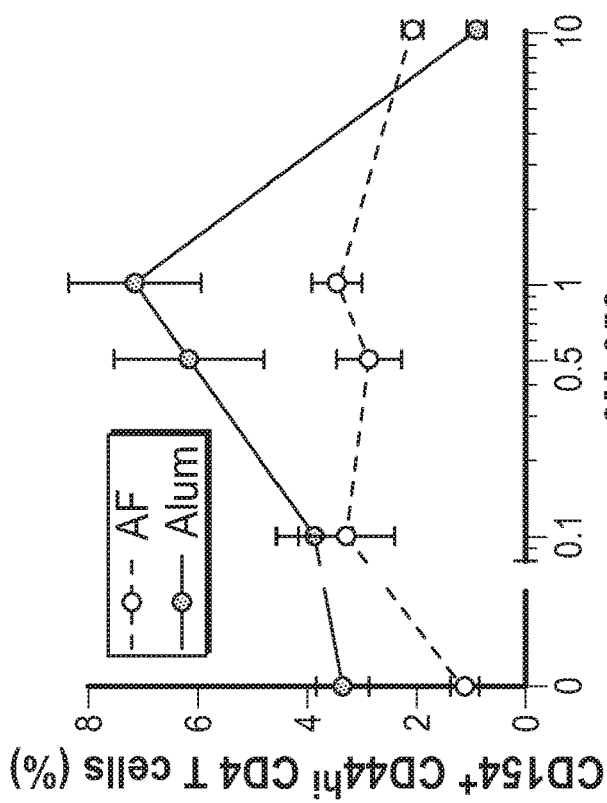

To determine whether binding 3M-052-AF to aluminum oxyhydroxide fundamentally changed its adjuvant activity or simply altered its bioavailability, the adjuvant activity of 3M-052-AF alone or bound to aluminum oxyhydroxide over a two $\log_{10}$ dose range was examined. Three weeks after the first immunization with adjuvanted ID93, the Alum-adsorbed formulation of 3M-052-AF consistently elicited higher serum antibody titers across the entire dose range compared to either Alhydrogel® alone or the same dose range of 3M-052-AF (FIGS. 6A and 6B). Similarly 3M-052-Alhydrogel® demonstrated a bell shaped dose response for augmenting ID93-specific CD4 T cells with the peak response of the tested doses at 1 μg. These CD154 and IFN-γ responses were substantially higher than those elicited with ID93 adjuvanted with aluminum oxyhydroxide or 3M-052-AF at 0.1, 1, or 10 μg (FIGS. 6C and 6D). Similar dose responses were observed for TNF and IL-2 producing CD4 T cells as well. Based on this, it can be concluded that binding 3M-052-AF to aluminum oxyhydroxide alters its adjuvant activity by some means other than simply changing the bioavailability over a 1 $\log_{10}$ range in either direction.

Figure 7A:
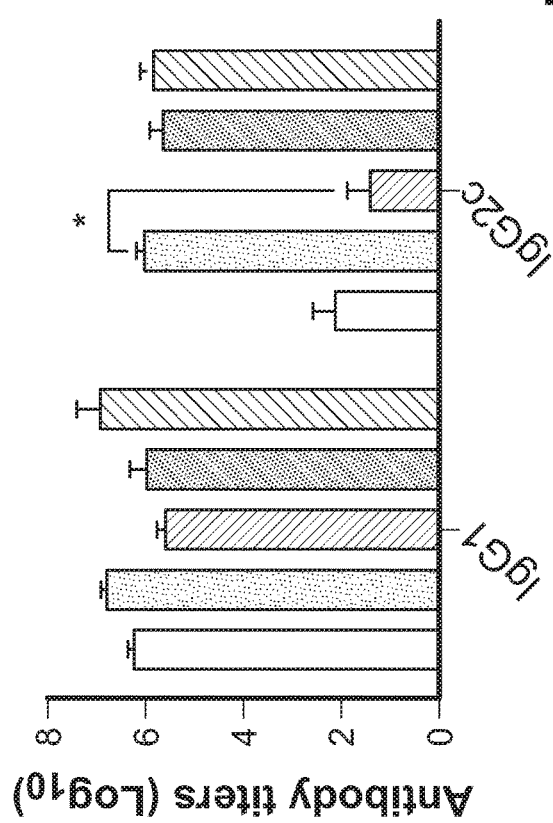
FIG. 7A-7B show that TLR7 is used for the TH1 inducing adjuvant activity of 3M-052. Wildtype C57BL/6 or B6.129S1-TLR7$^{tm1Flv}$ (TLR7$^{-/-}$) mice were immunized twice three weeks apart via intramuscular injection with ID93 (0.5 µg) adjuvanted with Alhydrogel®, 3M-052-AF (1 µg) bound to Alhydrogel®, or GLA-AF (5 µg) bound to Alhydrogel®.
Figure 7B:
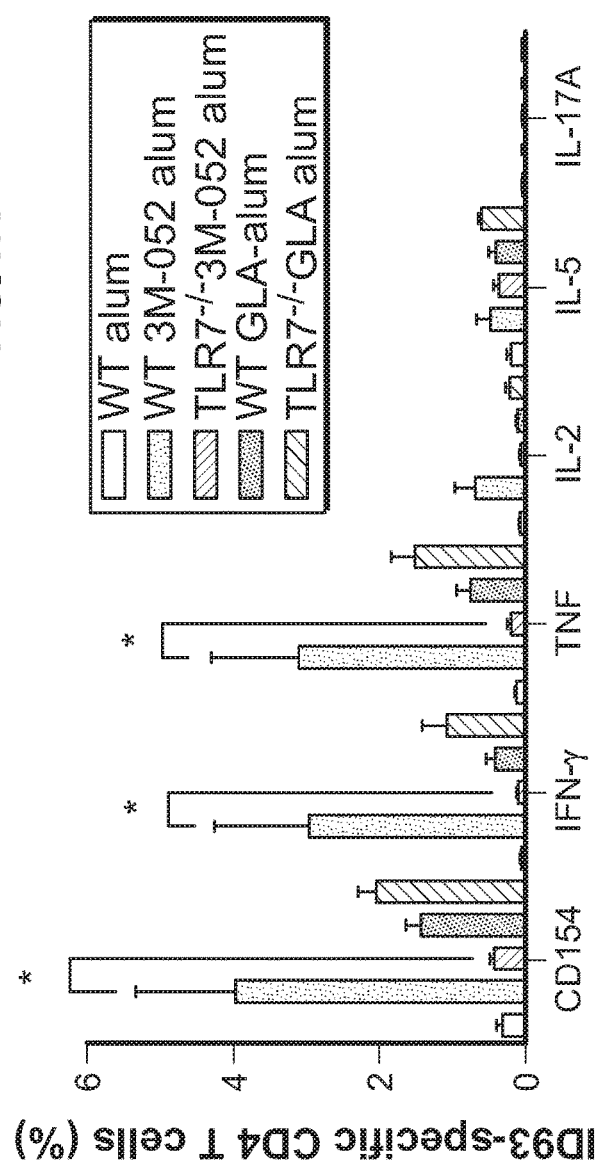

In vitro 3M-052 activates human TLR7 and TLR8 (5). To determine whether these innate immune receptors are a factor for the in vivo adjuvant activity of 3M-052-Alhydrogel®, the immune responses of vaccinated wild type (WT) C57BL/6 mice and mice lacking TLR7 (C57BL/6 mice express a hypofunctional TLR8) were compared. As a control, C57BL/6 and TLR7-/- mice were immunized with ID93 adjuvanted with the TLR4 agonist adjuvant GLA-Alum. All of the immunized groups produced high titers of ID93-specific IgG1 antibodies, regardless of adjuvant or genotype (FIG. 7A). Both 3M-052-Alhydrogel® and GLA-Alhydrogel® also elicited high titers of IgG2c in C57B/6 mice compared to Alhydrogel® alone. In TLR7-/- mice the IgG2c induction was drastically reduced in animals immunized with ID93+3M-052-Alum, whereas the IgG2c response to ID93+GLA-Alhdyrogel was not affected by TLR7 deficiency, showing that TLR7 was used to recognize 3M-052, but not Alhydrogel® or GLA. ID93+3M-052-Alhdyrogel® also elicited robust cellular responses in WT mice characterized by CD4 T cells capable of producing IFN-γ and TNF with very little IL-5 or IL-17A produced (markers of TH2 and TH17 immunity, respectively). However in TLR7-/- mice ID93+3M-052-Alhydrogel® elicited only minor CD4 T cell responses to ID93 which were not substantially different in magnitude from the responses elicited by ID93 adjuvanted with Alhydrogel® alone in WT mice (FIG. 7B). Immunization of WT and TLR7-/- mice with ID93+GLA-Alhydrogel® elicited similar TH1 responses indicating that TLR7-/- mice are not impaired in their CD4 T cell response to vaccines with other TLR agonist containing adjuvants formulated on Alum. Therefore, it can be concluded that similar to the in vitro findings, 3M-052-Alhydrogel® uses TLR7 for its in vivo adjuvant activity, particularly in eliciting high frequencies of TH1 CD4 T cells and IgG2c switched antibody responses.

Figure 8A:
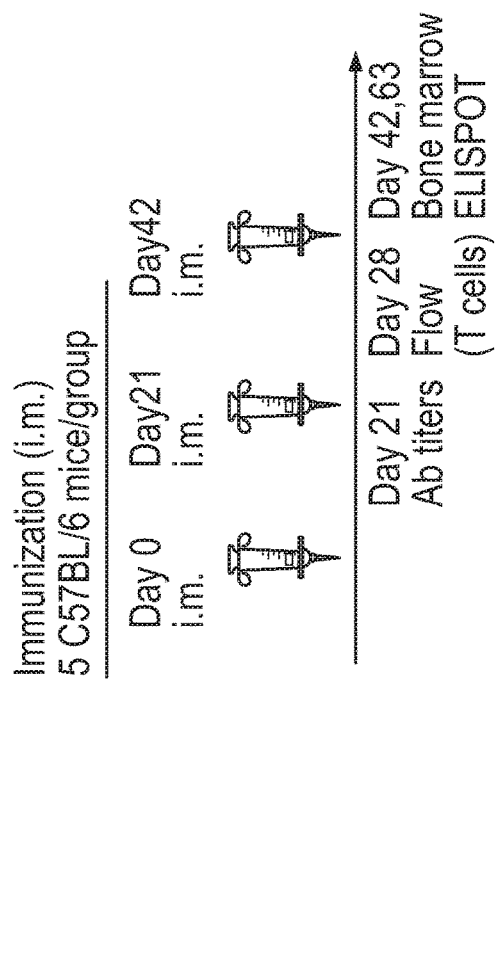
FIG. 8A-8D show that HIV gp120 antigen formulated with 3M-052-Alhydrogel induces enhanced antibody and TH1-type cellular responses compared to HIV gp120 antigen formulated with 3M-052-AdjuPhos, 3M-052 alone, or either type of Alum alone. C57BL/6 mice were immunized three times, three weeks apart via intramuscular injection with HIV gp120 antigen (10 µg) alone or adjuvanted with 3M-052-AF (1 µg), Alhydrogel®, AdjuPhos®, 3M-052-Alhydrogel®, or 3M-052-AdjuPhos®.
Figure 8B:
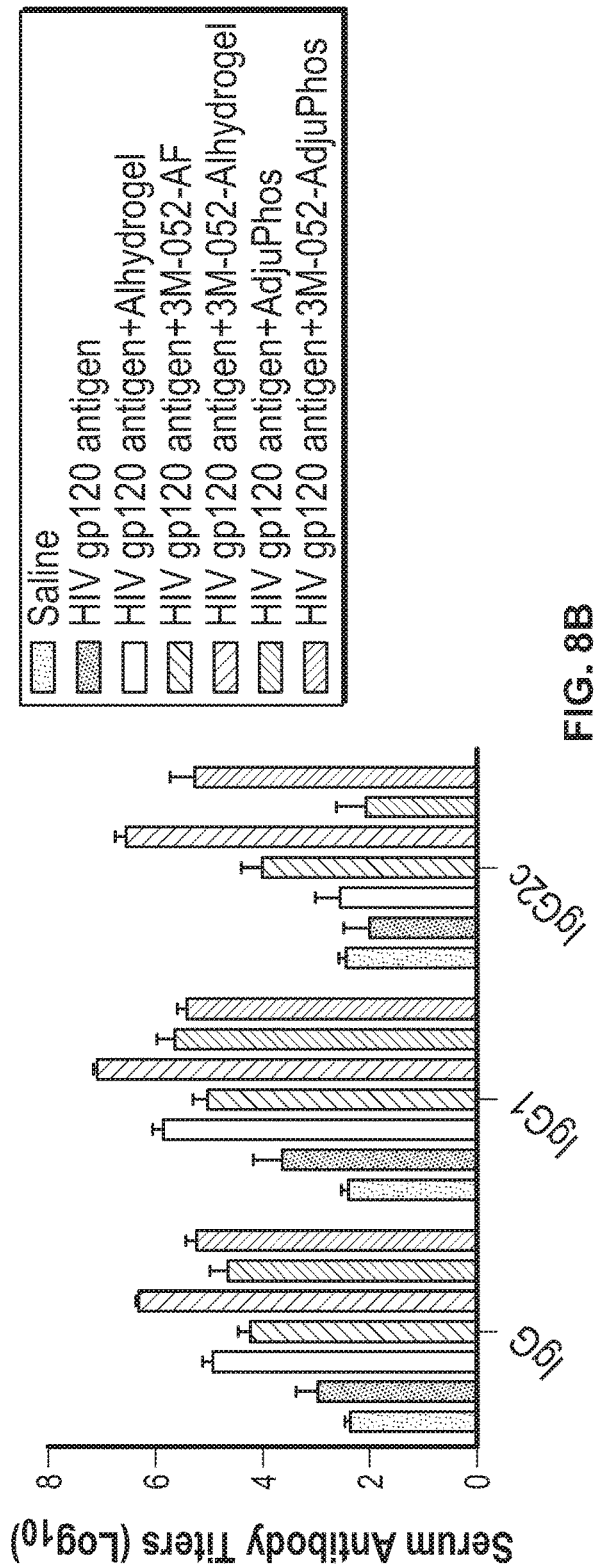
Figures 8C, 8D:
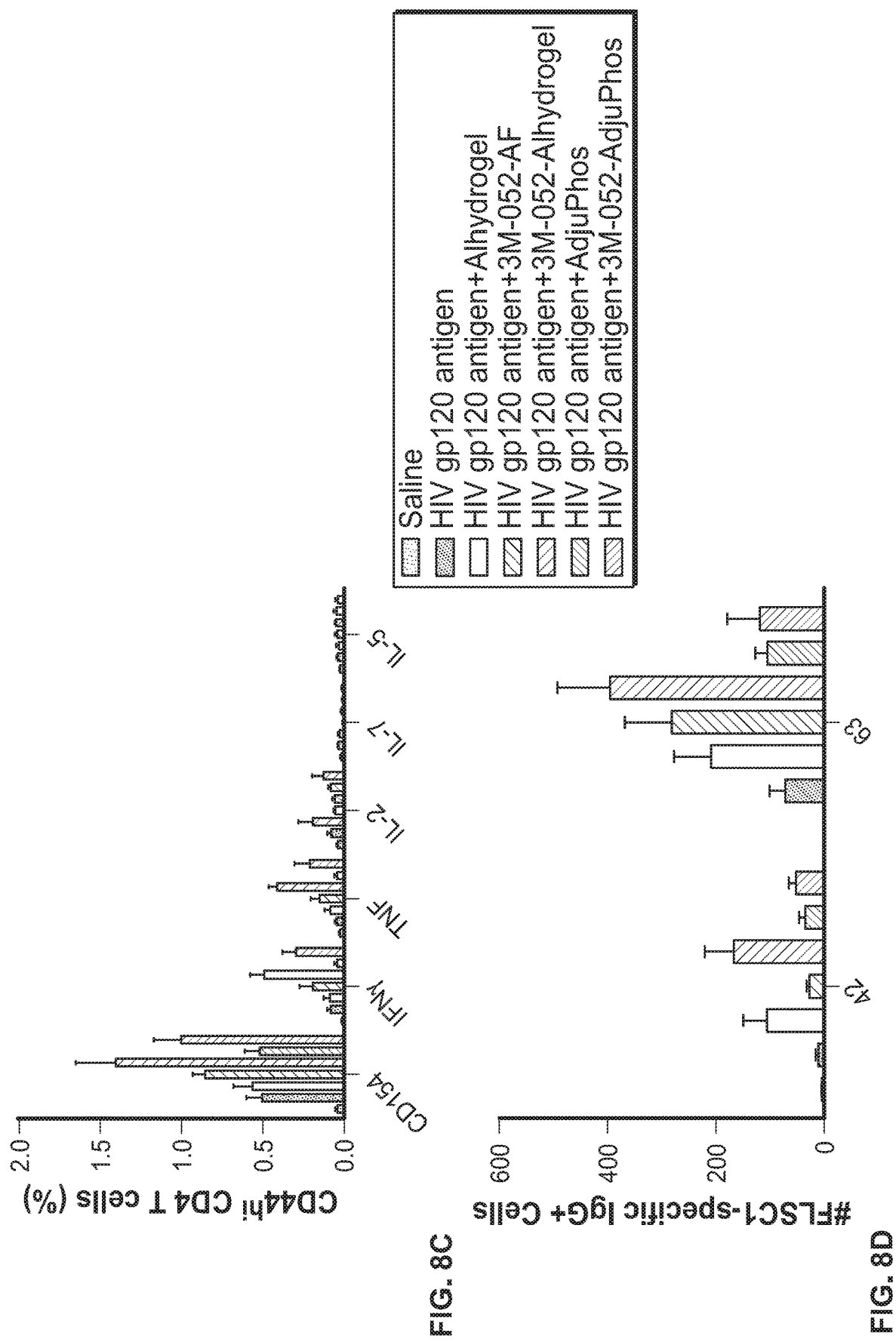
Figure 11A:
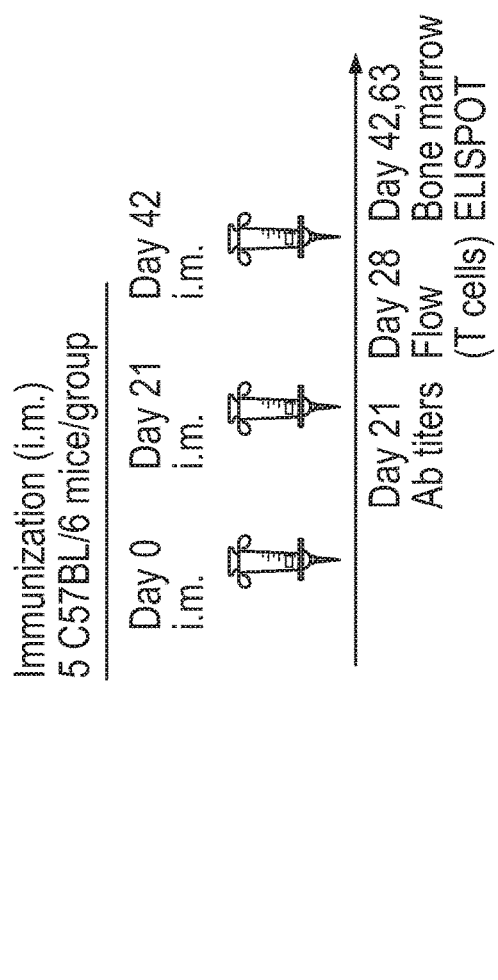
FIG. 11A-11C shows that HIV gp120 antigen formulated with 3M-052-Alhydrogel induces enhanced vaginal and TH1-type cellular responses. C57BL/6 mice were immunized three times, three weeks apart via intramuscular injection with HIV gp120 antigen (10 µg) alone or adjuvanted with 3M-052-AF (1 µg), Alhydrogel®, AdjuPhos®, 3M-052-Alhydrogel®, or 3M-052-AdjuPhos®.
Figure 11B:
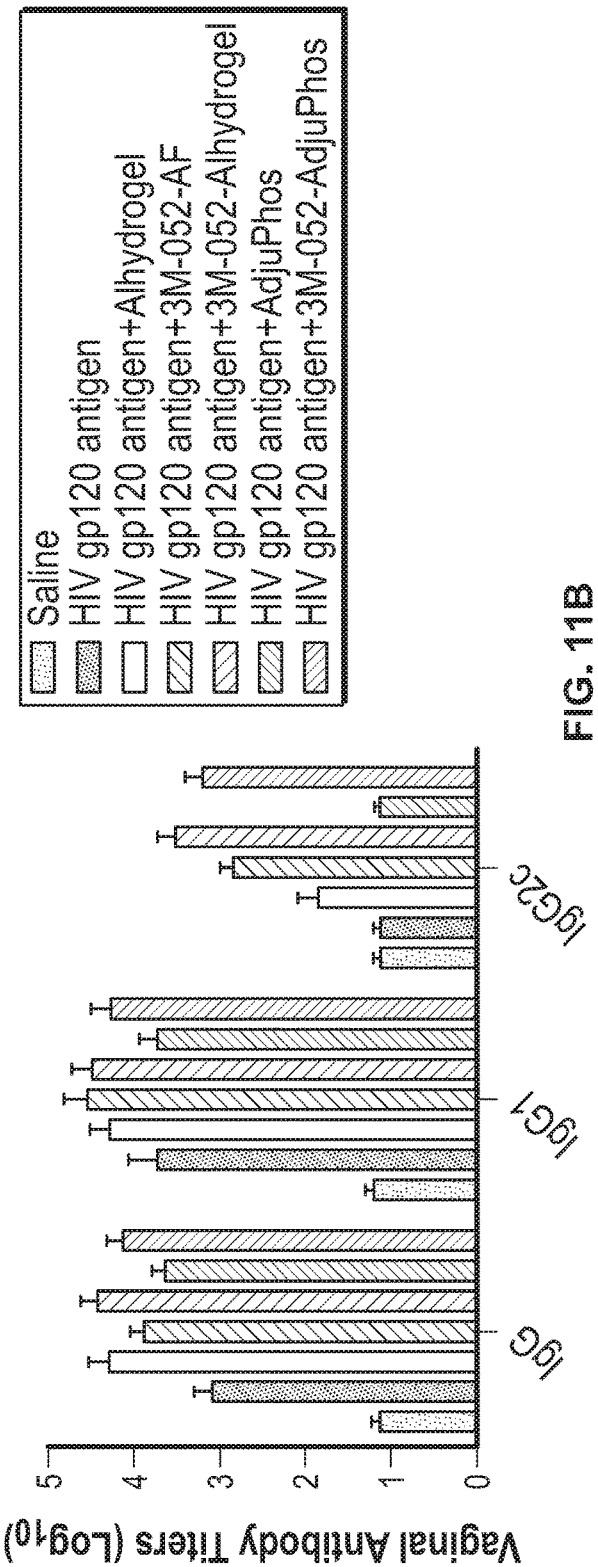
Figure 11C:
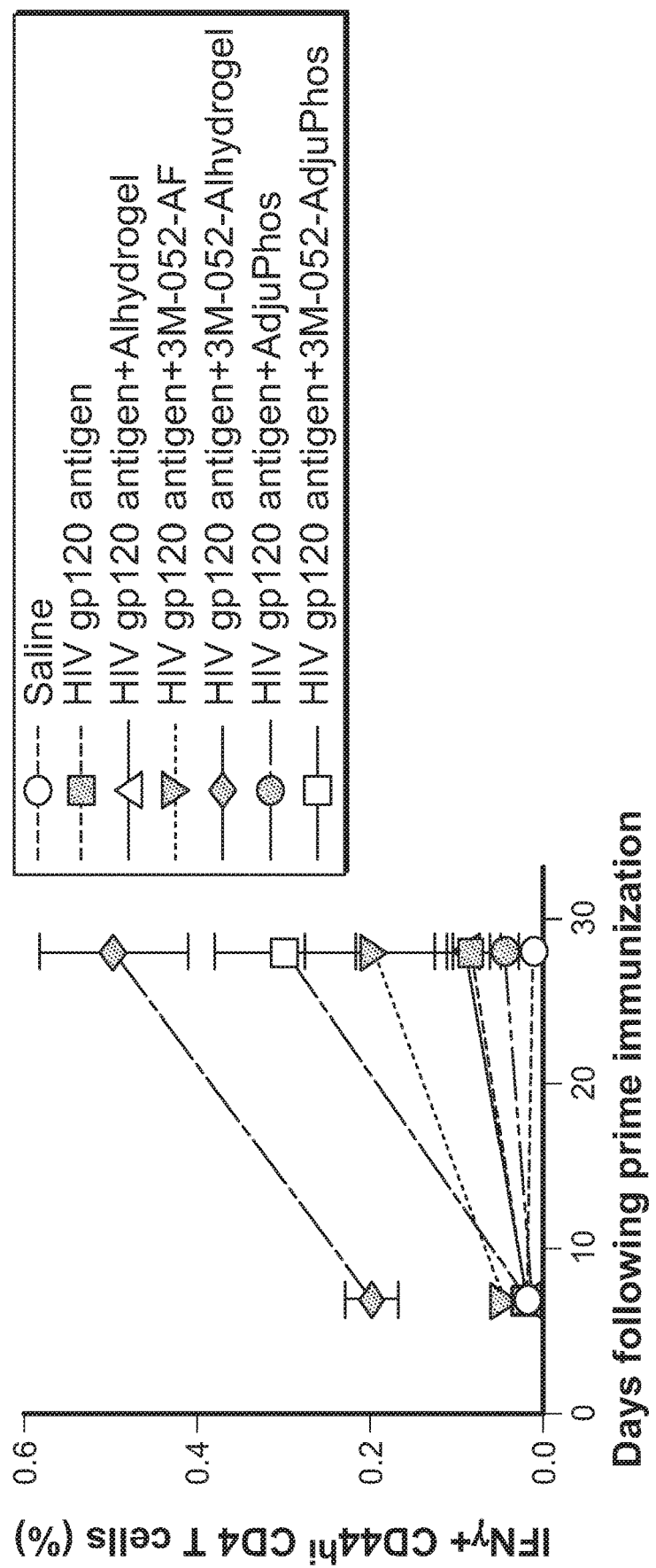

To test the in vivo adjuvant activity of 3M-052 with a different vaccine antigen as well as the effect of different aluminum salts, C57BL/6 mice were immunized with the HIV gp120 antigen (13) adjuvanted with either 3M-052-AF, aluminum oxyhydroxide, aluminum phosphate, or 3M-052-AF in combination with aluminum oxyhydroxide or aluminum phosphate. Three weeks after the first immunization, the most elevated serum IgG and IgG2c antibody responses were elicited by HIV gp120 antigen adjuvanted with 3M-052-aluminum oxyhydroxide (FIG. 8B). Interestingly, 3M-052-aluminum oxyhydroxide also produced the highest levels of mucosal IgG2c and antibody-secreting long lived plasma cells (FIGS. 8D and 11). Moreover, the formulation containing 3M-052 and aluminum oxyhydroxide was the most potent inducer of IFNγ and TNF from CD4+ T cells (FIG. 8C), particularly one week after the prime immunization (FIG. 11). Overall, 3M-052-aluminum oxyhydroxide appeared to have more potent adjuvant activity in this model than 3M-052-aluminum phosphate; however, since the HIV gp120 antigen adsorbs to aluminum oxyhydroxide but not substantially to aluminum phosphate (data not shown), reduced immunogenicity responses could be attributable to less optimal adsorption of both antigen and/or 3M-052 to aluminum phosphate.

Induction of a robust adaptive immune response to vaccine antigens uses appropriate activation of the innate immune system to provide the costimulatory and cytokine milieu. Thus, the innate immune responses in the draining lymph node that are altered by immunization with 3M-052+/-aluminum phosphate or aluminum oxyhydroxide was analyzed. 3M-052 synergized with aluminum oxyhydroxide and to a lesser extent aluminum phosphate to elicit a robust increase in the number of inflammatory monocytes (CD11b$^+$ Ly6$^+$) in the draining lymph node 18 hours after i.m. injection (FIG. 9A). Similarly 3M-052 and both alum formulations augmented expression of the co-stimulatory molecule CD86 on APCs including B cells, monocytes and dendritic cells and transient activation of CD4 and CD8 T cells as well as B cells as indicated by CD69 expression (FIGS. 9B and C). 3M-052 uniquely synergized with aluminum oxyhydroxide to augment number of NK cells expressing IFN-γ and neutrophils producing IL-1 (FIG. 9D), both molecules important for the induction of robust TH1 responses with vaccine adjuvants (14). This innate response to the synergy between 3M-052 and alum likely creates the appropriate environment for the robust generation of adaptive immune responses to the vaccine antigens. The expansion of IFN-γ producing NK cells and IL-1 producing neutrophils correlates with the stronger adjuvant activity of 3M-052+aluminum oxyhydroxide compared to the weaker responses induced by 3M-052+aluminum phosphate.

Discussion

Appropriate formulation of TLR7/8 agonists is an attractive adjuvant development approach for several reasons including manufacturability, induction of potent TH1 responses, and prior use in an FDA-approved product. The ability of imidazoquinolines to target TLR7 and/or TLR8 to generate enhanced TH1-type innate immune responses, including IgG2 antibodies in mice, has been documented in the literature (15-17). As synthetic small molecules, imidazoquinolines can be manufactured cost effectively and at high purity. The TLR7 ligand imiquimod is the active component in the topical cream Aldara®, approved for human immunotherapeutic use to treat skin cancer and genital warts. However, injected imidazoquinolines as vaccine adjuvants have not progressed beyond early phase clinical testing. Due to their small size, it is hypothesized that soluble unformulated imidazoquinolines such as R848 rapidly diffuse from the injection site, causing systemic immune activation rather than localized stimulation. For this reason, strategies to "slow down" imidazoquinoline diffusion such as covalent conjugation to vaccine antigens or encapsulation in particulate formulations have shown promise in preclinical testing (5, 18-21). Smirnov et al. describe a chemical synthesis approach resulting in the addition of an 18-carbon chain to an imidazoquinoline structure that maintains local adjuvant activity but not systemic responses evident with non-lipidated structures such as R848 (5). This molecule, called 3M-052 (FIG. 1), is thus more amenable to incorporation in lipid-based formulations such as nanosuspensions, liposomes, or emulsions.

Work by Wu et al. demonstrated that chemical synthesis of new TLR7 ligands with phosphonate groups facilitated adsorption to aluminum oxyhydroxide, resulting in improved transient localized adjuvant activity while reducing systemic activation (21). Alum-adsorbed TLR7 formulations effectively boosted antibody magnitude and quality to various vaccine antigens, including enhanced protection against challenge compared to the antigen with alum alone or the TLR7 ligand alone (21). In contrast, the formulation approach described herein does not substantially use phosphonate groups on the PRR ligand to facilitate adsorption of PRR ligands to aluminum salts, and thus may have broader applicability. The ability to promote adsorption of PRR ligands to aluminum salts could provide a development advantage from a regulatory standpoint, since an alum-adsorbed PRR ligand formulation is already contained in approved vaccines such as Cervarix®. A formulation-based approach could avoid the need to chemically modify existing agonist structures, relying instead on the properties of the formulation to promote adsorption to aluminum salts. Moreover, lipid formulation modifications could tailor PRR ligand adsorption preference to specific aluminum salts such that vaccine antigen and PRR ligand could be adsorbed to the same type of aluminum salt. Such excipient properties include length and saturation of acyl chains and headgroup structure/charge. We found that the latter appeared to be the main determinant in the ability of the nanosuspension to adsorb to aluminum salts, although acyl chain structure should also be taken into account in order to ensure stable suspension formation between PRR ligand and helper lipid.

Despite the versatility of this nanosuspension-based formulation approach, it is noted that the effects of buffer/salt selection, aluminum salt type, order of mixing, diluent, and vaccine antigen properties should be well characterized in order to optimize the adjuvanted vaccine formulation. For example, it was not possible to completely distinguish the importance of 3M-052-AF adsorption independent of antigen adsorption, since HIV gp120 antigen and 3M-052-AF adsorbed less optimally to aluminum phosphate compared to aluminum oxyhydroxide.

The helper lipid approach was used to adsorb TLR4 ligands to aluminum oxyhydroxide. The otherwise insoluble TLR4 ligand GLA can be formulated as an aqueous suspension using a helper lipid, which can then be mixed with aluminum oxyhydroxide to allow for adsorption. However, in the case of GLA the agonist itself contains a phosphate group which promotes adsorption through ligand exchange. In the case of 3M-052, the agonist contains no phosphate group, thus adsorption due to ligand exchange can be attributed to the helper lipid. Although in the present disclosure, ID93+3M-052-Alum appeared to induce a more potent TH1 response than ID93+GLA-Alum. Cellular location and distribution of TLR7/8 and TLR4 is significantly different and varies between species (17). For example, TLR8 is considered refractory in mice; thus, an agonist such as 3M-052 may elicit altered or enhanced responses in humans or other species with functional TLR8. Such considerations, combined with the data presented here, indicate that an Alum-based TLR7/8 adjuvant formulation could provide a potent adjuvant formulation for TH1 responses in humans.

3M-052 and alum synergized to increase expression of the co-stimulatory molecule CD86 on APCs in the draining LN and to transiently activate lymphocytes to remain in the draining lymph node in an antigen-independent fashion. By activating APCs and trapping lymphocytes in the same draining LN this synergy creates an optimal environment for lymphocyte priming and expansion. Interestingly innate responses including early production of IFN-γ and IL-1β which we found to be used for the adjuvanticity of the GLA-SE (14) were also pronounced when 3M-052 was formulated with aluminum oxyhydroxide. This may suggest that these parameters could be useful universal signatures of effective adjuvant activity. Identification of such signatures would aid the rational development of new vaccine candidates.

In conclusion, a method to formulate lipid-based PRR ligands into aqueous nanosuspensions that can be made to adsorb to aluminum salts based on the properties of the helper lipid was developed. The ability to develop Alum-compatible formulations of new PRR ligands may enable more rapid translation to the clinic since such formulations are analogous to the TLR4 ligand-Alum combination employed in Cervarix®, and aluminum salts are the most widely employed class of adjuvants in human vaccines, with a well-established safety and immunogenicity record.

Example 2. Adsorption of a Synthetic TLR4 Ligand to Alum

The adsorption of the stable aqueous suspensions of TLR 4 ligand GLA to aluminum oxyhydroxide or aluminum phosphate was tested and the results are shown in Table 4. These data indicate that adsorption of the TLR4 ligand can be tailored to aluminum oxyhydroxide or aluminum phosphate by appropriate selection of helper lipid.

TABLE 4

Adsorption of aqueous nanosuspensions of GLA to Alhydrogel ® or AdjuPhos ®.

| Helper Lipid | Aluminum Salt | GLA Conc. in Supernatant (µg/ml) | Calculated Adsorption % |
|---|---|---|---|
| DPPC | — | 112 ± 4 | — |
| DPTAP | — | 88 ± 6 | — |
| DPPC | Alhydrogel ® | <10 | ≥91% |
| DPTAP | Alhydrogel ® | 80 ± 1 | 1% |
| DPPC | AdjuPhos ® | 114 ± 4 | 0% |
| DPTAP | AdjuPhos ® | <10 | ≥89% |

REFERENCES

1. Glenny A T, Pope C G, Waddington H, Wallace U. The antigenic value of toxoid precipitated by potassium alum. J Pathol Bacteriol. 1926; 29:31-40.
2. Hem S L, HogenEsch H. Aluminum-containing adjuvants: properties, formulation, and use. In: Singh M, editor. Vaccine Adjuvants and Delivery Systems. Hoboken, N.J.: John Wiley & Sons: 2007, p. 81-114.
3. Didierlaurent A M. Morel S, Lockman L, Giannini S L, Bisteau M, Carlsen H, Kielland A, Vosters O, Vanderheyde N, Schiavetti F, Larocque D, Van Mechelen M, Garcon N. AS04, an aluminum salt- and TLR4 agonist-based adjuvant system, induces a transient localized innate immune response leading to enhanced adaptive immunity. J Immunol. 2009; 10:6186-97.
4. Mullen G E D, Aebig J A, Dobrescu G. Rausch K, Lambert L, Long C A, Miles A P, Saul A. Enhanced antibody production in mice to the malaria antigen AMA1 by CPG 7909 requires physical association of CpG and antigen. Vaccine. 2007; 25(29):5343-7.
5. Smirnov D, Schmidt J J, Capecchi J T, Wightman P D. Vaccine adjuvant activity of 3M-052: an imidazoquinoline designed for local activity without systemic cytokine induction. Vaccine. 2011; 29:5434-42.
6. Misquith A, Fung M, Dowling Q M, Guderian J A, Vedvick T S, Fox C B. In vitro evaluation of TLR4 agonist activity: formulation effects. Coll Surf B: Biointerfaces. 2014; 113:312-9.
7. Fung H W M, Mikasa T J T, Vergara J, Sivananthan S J, Guderian J A, Duthie M S, Vedvick T S. Optimizing manufacturing and composition of a TLR4 nanosuspension: physicochemical stability and vaccine adjuvant activity. J Nanobiotechnology. 2013; 11:43.
8. Fox C B. Characterization of TLR4 agonist effects on Alhydrogel sedimentation: a novel application of laser scattering optical profiling. J Pharm Sci. 2012; 101:4357-64.
9. Chollet J L, Jozwiakowski M J, Phares K R, Reiter M J, Roddy P J, Schultz H J, Ta Q V. Tomai M A. Development of a topically active imiquimod formulation. Pharm Dev Technol. 1999:4:35-43.
10. Iyer S, Robinett R S R, HogenEsch H, Hem S L. Mechanism of adsorption of hepatitis B surface antigen by aluminum hydroxide adjuvant. Vaccine. 2004; 22(11-12):1475-9.
11. Bertholet S, Ireton G C, Ordway D J, Windish H P, Pine S O. Kahn M, Phan T, Orme I M, Vedvick T S. Baldwin S L, Coler R N, Reed S G. A defined tuberculosis vaccine candidate boosts BCG and protects against multidrug-resistant *Mycobacterium tuberculosis*. Sci Transl Med. 2010; 2:53ra74.
12. Dowling Q M, Sivananthan S J, Guderian J A. Moutaftsi M, Chesko J D, Fox C B, Vedvick T S, Kramer R M. Modulating Potency: Physicochemical Characteristics are a Determining Factor of TLR4-Agonist Nanosuspension Activity. Journal of Pharmaceutical Sciences. 2014; 103 (3):879-89.
13. Fouts T R, Tuskan R, Godfrey K, Reitz M, Hone D. Lewis G K, DeVico A L. Expression and Characterization of a Single-Chain Polypeptide Analogue of the Human Immunodeficiency Virus Type 1 gp120-CD4 Receptor Complex. Journal of Virology. 2000:74(24):11427-36.
14. Desbien A L, Reed S J, Bailor H R, Cauwelaert N D, Laurance J D, Orr M T, Fox C B, Carter D, Reed S G, Duthie M S. Squalene emulsion potentiates the adjuvant activity of the TLR4 agonist, GLA, via inflammatory caspases, IL-18, and IFN-γ. European Journal of Immunology. 2015; 45(2):407-17.
15. Vasilakos J P, Tomai M A. The use of Toll-like receptor 7/8 agonists as vaccine adjuvants. Expert Review of Vaccines. 2013; 12(7):809-19.
16. Schwenk R, DeBot M, Porter M, Nikki J, Rein L, Spaccapelo R, Crisanti A, Wightman P D, Ockenhouse C F, Dutta S. IgG2 Antibodies against a Clinical Grade *Plasmodium falciparum* CSP Vaccine Antigen Associate with Protection against Transgenic Sporozoite Challenge in Mice. PLoS ONE. 2014:9(10):e111020.
17. Reed S G, Orr M T, Fox C B. Key roles of adjuvants in modern vaccines. Nat Med. 2013; 19:1597-608.
18. Fox C, Sivananthan S, Duthie M, Vergara J, Guderian J, Moon E, Coblentz D, Reed S, Carter D. A nanoliposome delivery system to synergistically trigger TLR4 AND TLR7. Journal of Nanobiotechnology. 2014; 12(1):17.
19. Kasturi S P, Skountzou I, Albrecht R A, Koutsonanos D, Hua T, Nakaya H I, Ravindran R, Stewart S, Alam M, Kwissa M, Villinger F, Murthy N, Steel J, Jacob J, Hogan R J, García-Sastre A, Compans R, Pulendran B. Programming the magnitude and persistence of antibody responses with innate immunity. Nature. 2011; 470:543-7.
20. Wille-Reece U, Wu C-y, Flynn B J, Kedl R M, Seder R A. Immunization with HIV-1 Gag Protein Conjugated to a TLR7/8 Agonist Results in the Generation of HIV-1 Gag-Specific Th1 and CD8+ T Cell Responses. The Journal of Immunology. 2005; 174(12):7676-83.
21. Wu T Y-H, Singh M, Miller A T, De Gregorio E, Doro F, D'Oro U, Skibinski D A G, Mbow M L, Bufali S, Herman A E, Cortez A, Li Y, Nayak B P, Tritto E, Filippi C M, Otten G R, Brito L A. Monaci E, Li C, Aprea S, Valentini S, Calabró S, Laera D, Brunelli B, Caproni E, Malyala P, Panchal R G, Warren T K. Bavari S, O'Hagan D T, Cooke M P, Valiante N M, Rational design of small molecules as vaccine adjuvants. Science Translational Medicine. 2014; 6(263):263ra160

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition comprising:
   (a) a TLR7/8 agonist, wherein the TLR7/8 agonist is 3M-052;
   (b) a helper lipid, wherein the helper lipid is DSTAP, DLPG, DMPG, DPPG, DSPG, or DOPG, wherein a molar ratio of the TLR7/8 agonist to the helper lipid is about 1:2; and
   (c) an aluminum salt, wherein the composition is an aqueous formulation comprising a stable nanosuspension of the TLR7/8 agonist and the helper lipid adsorbed to the aluminum salt.

2. The composition of claim 1, wherein the stable nanosuspension has a particle size of 400 nm or less.

3. The composition of claim 1, wherein the TLR7/8 agonist in the stable nanosuspension is adsorbed to the aluminum salt at 75 percent or more of the aluminum salt.

4. The composition of claim 1, wherein the aluminum salt is selected from the group consisting of aluminum hydroxide, aluminum trihydrate, aluminum oxyhydroxide, aluminum phosphate, aluminum hydroxyphosphate, aluminum hydroxyphosphate sulfate, and potassium aluminum sulfate.

5. The composition of claim 4, wherein the aluminum salt comprises an aluminum hydroxide gel.

6. The composition of claim 4, wherein the aluminum salt comprises an aluminum phosphate gel.

7. A composition comprising:
   (a) a TLR7/8 agonist, wherein the TLR7/8 agonist is 3M-052;
   (b) a helper lipid; and
   (c) an aluminum salt, wherein the aluminum salt is aluminum hydroxide gel and the helper lipid is DLPG, DMPG, DPPG, DSPG, or DOPG, wherein the composition is an aqueous formulation comprising a stable nanosuspension of the TLR7/8 agonist and the helper lipid adsorbed to the aluminum salt.

8. A composition comprising:
   (a) a TLR7/8 agonist, wherein the TLR7/8 agonist is 3M-052;
   (b) a helper lipid; and
   (c) an aluminum salt, wherein the aluminum salt is aluminum phosphate gel and the helper lipid is DSTAP, wherein the composition is an aqueous formulation comprising a stable nanosuspension of the TLR7/8 agonist and the helper lipid adsorbed to the aluminum salt.

9. The composition of claim 1, further comprising an antigen.

10. The composition of claim 9, wherein the antigen is selected from a tuberculosis-related antigen, influenza-related antigen, hemagglutinin-related antigen, cancer-related antigen, viral-related antigen and amebiasis-related antigen.

11. The composition of claim 10, wherein the tuberculosis-related antigen is selected from the group consisting of ID93, 1D91, and BCG.

12. The composition of claim 10, wherein the influenza-related antigen is selected from the group consisting of H5N1, influenza A, influenza B, and influenza C.

13. The composition of claim 10, wherein the amebiasis-related antigen is LecA.

14. The composition of claim 10, wherein the viral-related antigen is selected from the group consisting of hepatitis B and hepatitis C.

15. The composition of claim 1, wherein the composition is stable at 2-8° C. for at least 16 weeks.

16. The composition of claim 1, wherein the composition is a vaccine.

17. The composition of claim 2, wherein the stable nanosuspension has a particle size of 200 nm or less.

* * * * *